(12) United States Patent
Hofer et al.

(10) Patent No.: US 6,875,727 B2
(45) Date of Patent: Apr. 5, 2005

(54) USE OF MACROLIDES IN PEST CONTROL

(75) Inventors: Dieter Hofer, Liestal (CH); Marius Sutter, Binningen (CH); Franz Brandl, Schopfheim (DE); Bruce Lee, Bad Krozingen (DE); Roger Graham Hall, Pfeffingen (CH); Max Angst, Magden (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 10 days.

(21) Appl. No.: 10/256,365

(22) Filed: Sep. 27, 2002

(65) Prior Publication Data

US 2003/0148965 A1 Aug. 7, 2003

Related U.S. Application Data

(63) Continuation of application No. 09/581,980, filed as application No. PCT/EP98/08384 on Dec. 21, 1998, now abandoned.

(51) Int. Cl.$^7$ .......................... A01N 25/26; A01N 43/00; A01N 25/00; A61K 31/33

(52) U.S. Cl. ........................ 504/100; 514/183; 424/405

(58) Field of Search ................................. 504/100, 218, 504/219, 220; 514/183, 450; 424/405

(56) References Cited

U.S. PATENT DOCUMENTS

| 4,315,929 A | 2/1982 | Freedman et al. |
|---|---|---|
| 5,185,365 A | 2/1993 | Eisner et al. |
| 5,221,758 A | 6/1993 | Maynard |
| 6,387,388 B1 * | 5/2002 | Misselbrook et al. ........ 424/409 |

FOREIGN PATENT DOCUMENTS

| DE | 3602276 | 8/1987 |
|---|---|---|
| EP | 0110667 | 6/1984 |
| EP | 110667 | 6/1984 |
| EP | 0242502 | 10/1987 |
| EP | 0327270 | 8/1989 |
| GB | 2220856 | 1/1990 |
| WO | 9533380 | * 12/1995 |
| WO | WO96/28023 | 9/1996 |
| WO | WO97/40692 | 11/1997 |
| WO | WO97/45017 | 12/1997 |
| WO | WO 99/33343 | 7/1999 |
| WO | WO 99/60856 | 12/1999 |
| WO | WO 02/28186 | 4/2002 |
| WO | WO 02/30205 | 4/2002 |

OTHER PUBLICATIONS

Derwent AN 84–316303, XP002102217.
Arkans. Agricult. Exp. No. 188., pp. 211–213, Station XP002102210, 1998, Allen et al.
BT Cotton, Artrop. Mang. Tests, vol. 23, pp 229–230, XP2102211, 1998, Halcomb et al.
Artrop. Mang. Tests, vol. 23, pp. 228–229, 1998, Gore et al.
BT–Cotton; Proc. of the beltwide Cotton conf., vol. 2, p. 1220–1221, 1998, Roberts et al.
Proc. N.Z. Plant. Prot. Conf. pp. 228–232, 1998, Barker et al.
J. Nematol. vol. 28, pp. 687–694, XP002102214, 1996, Blackburn et al.
Avermectin Ann. Appl. Biol., vol. 114, suppl. pp. 18–19, XP002102215, 1989, Nwadinobi et al.
Residues of Avermectin vol. 35, pp. 859–864, 1988, Anson Moye.
Pesticide Manual 10th Edition, pp. 3–4, 1994, C. Tomlin (ED).
Brighton Crop Prot., Conf. 1, p. 57–64, 1988, Dybas.
Proc. Br. Crop Prot. Conf. 1, pp. 133–138, 1984, Scott et al.
J. of Agr. Food Chem. vol. 35, No. 6, 1988, pp. 859–864, H. Anson Moye.
Ann. Appl. Biol., vol. 114 Suppl., 1989, pp. 18–19, Nwadinobi.
Proc. N.Z. Plant. Prot. Conf. 1993, 228–232, Barker.
J. Nematol. vol. 28, (1996) pp. 687–694, Blackburn.
Proc. Belt. Cotton Conf. vol. 2, pp. 1177–1180, 1998, D.A. Herbert.
Arth. Manag. Tests, 25, p. 250, 2000, Burris.
Proc. Belt. Cotton Conf. vol. 2, 122, 1999, Gustafson (Riggs).

* cited by examiner

Primary Examiner—Alton N. Pryor
(74) Attorney, Agent, or Firm—William A. Teoli, Jr.

(57) ABSTRACT

There is now described a method of controlling pests with macrolide compounds; more specifically
A) a method of controlling pests in and on transgenic crops of useful plants, such as, for example, in crops of maize, cereals, soya beans, tomatoes, cotton, potatoes, rice and mustard, with a macrolide compound, characterized in that a pesticidal composition comprising a macrolide compound in free form or in agrochemically useful salt form and at least one auxiliary is applied to the pests or their environment, in particular to the crop plant itself;
B) A method of protecting plant propagation material and plant organs formed at a later point in time from attack by pests, characterized in that a pesticide comprising, as pesticidally active compound, at least one macrolide compound as active ingredient and at least one auxiliary in close spatial proximity to, or spatially together with, planting or applying the propagation material is employed to the site of planting or sowing;
C) a method of controlling wood pests and molluscs with a macrolide compound, wherein a pesticidally active amount of a pesticide comprising, as pesticidally active compound, at least one macrolide, in free form or agrochemically utilizable salt form, as active ingredient and at least one auxiliary is applied to the pests or their environment; the corresponding use of these compounds, corresponding pesticides whose active ingredient is selected from amongst these compounds, a method for the preparation and the use of these compositions, and plant propagation material which is protected in this manner from attack by pests.

15 Claims, No Drawings

USE OF MACROLIDES IN PEST CONTROL

This application is a continuation of U.S. Ser. No. 09/581,980, filed Jun. 20, 2000, and CPA Ser. No. 09/581,980, filed Feb. 27, 2002 (now abandoned), which is a 371 filing of International Application No. PCT/EP98/08384, filed Dec. 21, 1998, the contents being incorporated herein by reference.

The present invention relates to a method of controlling pests with macrolide compounds; more specifically to (A) a novel method of controlling pests in and on transgenic crops of useful plants with a macrolide compound;
(B) method of protecting plant propagation material and plant organs formed at a later point in time from attack by pests with such a macrolide compound; and
(C) a method of controlling wood pests and molluscs with a macrolide compound.

Certain pest control methods are proposed in the literature. However, these methods are not fully satisfactory in the field of pest control, which is why there is a demand for providing further methods for controlling and combating pests, in particular insects and representatives of the order Acarina, or for protecting plants, especially crop plants. This object is achieved according to the invention by providing the present method.

(A) A first aspect of the present invention therefore relates to a method of controlling pests in crops of transgenic useful plants, such as, for example, in crops of maize, cereals, soya beans, tomatoes, cotton, potatoes, rice and mustard, characterized in that a pesticidal composition comprising a macrolide compound, in particular abamectin, in free form or in agrochemically useful salt form and at least one auxiliary is applied to the pests or their environment, in particular to the crop plant itself; to the use of the composition in question and to propagation material of transgenic plants which has been treated with it.

Surprisingly, it has now emerged that the use of a macrolide compound for controlling pests on transgenic useful plants which contain—for instance—one or more genes expressing a pesticidally, particularly insecticidally, acaricidally, nematocidally or fugicidally active ingredient, or which are tolerant against herbicides, has a synergistic effect. It is highly surprising that the use of a macrolide compound in combination with a transgenic plant exceeds the additive effect, to be expected in principle, on the pests to be controlled and thus extends the range of action of the macrolide compound and of the active principle expressed by the transgenic plant in particular in two respects:

In particular, it has been found, surprisingly, that within the scope of invention (A) the pesticidal activity of a macrolide compound in combination with the effect expressed by the transgenic useful plant, is not only additive in comparison with the pesticidal activities of the macrolide compound alone and of the transgenic crop plant alone, as can generally be expected, but that a synergistic effect is present. The term "synergistic", however, is in no way to be understood in this connection as being restricted to the pesticidal activity, but the term also refers to other advantageous properties of the method according to the invention compared with the macrolide compound alone and the transgenic useful plant alone. Examples of such advantageous properties which may be mentioned are: extension of the pesticidal spectrum of action to other pests, for example to resistant strains; reduction in the application rate of the macrolide compound, or sufficient control of the pests with the aid of the compositions according to the invention even at an application rate of the macrolide compound alone and the transgenic useful plant alone are entirely ineffective; enhanced crop safety; improved quality of produce such as higher content of nutrient or oil, better fiber quality, enhanced shelf life, reduced content of toxic products such as mycotoxins, reduced content of residues or unfavorable constituents of any kind or better digestability; improved tolerance to unfavorable temperatures, draughts or salt content of water; enhanced assimilation rates such as nutrient uptake, water uptake and photosynthesis; favorable crop properties such as altered leaf aerea, reduced vegetative growth, increased yields, favorable seed shape/seed thickness or germination properties, altered colonialisation by saprophytes or epiphytes, reduction of senescense, improved phytoalexin production, improved of accelerated ripening, flower set increase, reduced boll fall and shattering, better attraction to beneficials and predators, increased pollination, reduced attraction to birds; or other advantages known to those skilled in the art.

The macrolide compounds used according to the inventions part (A), (B) and (C) are known to those skilled in the art. They are the classes of substances which are disclosed as milbemycins and avermectins, for example in U.S. Pat. Nos. 4,310,519, 5,077,298, German Offenlegungsschrift 2 717 040 or U.S. Pat. No. 4,427,663. These macrolides are also to be understood as meaning, in accordance with the invention, the derivatives of these substances, that is, for example, milbemycin oxime, moxidectin, ivermectin, abamectin, emamectin and doramectin, and also spinosyns of the formula

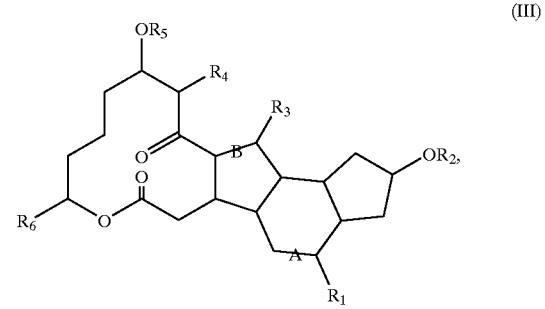

(III)

in which $R_1$, $R_2$, $R_3$, $R_4$, $R_5$ and $R_6$ independently of one another are hydrogen or a substituted or unsubstituted alkyl, alkenyl, alkynyl, cycloalkyl, aryl or heterocyclyl group and the substructures A and B independently of one another denote that the two carbon atoms, to which each of these substructures is bonded, are linked by a single bond, by a double bond or by a single bond and an epoxy bridge, in free form or, if appropriate, in agrochemically utilizable salt form.

Within the scope of invention (A) abamectin is preferred. Abamectin is a mixture of avermectin $B_{1a}$ and avermectin $B_{1b}$ and is described, for example, in The Pesticide Manual, 10$^{th}$ Ed. (1994), The British Crop Protection Council, London, page 3.

Also preferred within the scope of invention (A) is emamectin, which is 4"-De-oxy-4"-epi-N-methylamino avermectin $B_{1b}/B_{1a}$, known from U.S. Pat. No. 4,874,749 and as MK-244 described in Journal of Organic Chemistry, Vol. 59 (1994), pages 7704–7708. Agrochemically especially useful salts of emamectin are described in U.S. Pat. No. 5,288,710.

Also preferred within the scope of invention (A) is the group of compounds consisting of the spinosyns and their derivatives; the group of compounds consisting of the naturally occurring spinosyns; or the group of compounds consisting of the derivatives of the naturally occurring spinosyns. Preferably, the active ingredient may comprise, within the scope of the subject-matter of the invention (A), spinosyn A; spinosyn D; or a mixture composed of spinosyn A and spinosyn D; especially preferred is spinosad. Spinosad is known from the "The Pesticide Manual", 11$^{th}$ Ed. (1997), The British Crop Protection Council, London, United Kingdom, pages 1272–1273.

The agrochemically compatible salts of the macrolide compounds are, for example, acid addition salts of inorganic and organic acids, in particular of hydrochloric acid, hydrobromic acid, sulfuric acid, nitric acid, perchloric acid, phosphoric acid, formic acid, acetic acid, tri-fluoroacetic acid, oxalic acid, malonic acid, toluenesulfonic acid or benzoic acid. Preferred within the scope of the present invention is a composition known per se which comprises, as active ingredient, abamectin or spinosad in the free form, and emamectin as the benzoate salt.

The transgenic plants used according to the invention (A) are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The methods for generating such transgenic plants are widely known to those skilled in the art and described, for example, in the publications mentioned above.

The toxins which can be expressed by such transgenic plants include, for example, toxins, such as proteins which have insecticidal properties and which are expressed by transgenic plants, for example *Bacillus cereus* proteins or *Bacillus popliae* proteins; or *Bacillus thuringiensis* endotoxins (B.t.), such as CryIA(a), CryIA(b), CryIA(c), CryIIA, CryIIIA, CryIIIB2 or CytA; VIP1; VIP2; VIP3; or insecticidal proteins of bacteria colonising nematodes like *Photorhabdus* spp or *Xenorhabdus* spp such as *Photorhabdus luminescens, Xenorhabdus nematophilus* etc.; proteinase inhibitors, such as trypsin inhibitors, serine protease inhibitors, patatin, cystatin, papain inhibitors; ribosome-inactivating proteins (RIP), such as ricin, maize RIP, abrin, luffin, saporin or bryodin; plant lectins such as pea lectins, barley lectins or snowdrop lectins; or agglutinins; toxins produced by animals, such as scorpion toxins, spider venoms, wasp venoms and other insect-specific neurotoxins; steroid metabolism enzymes, such as 3-hydroxysteroid oxidase, ecdysteroid UDP-glycosyl transferase, cholesterol oxidases, ecdysone inhibitors, HMG-COAreductase, ion channel blockers such as sodium and calcium, juvenile hormone esterase, diuretic hormone receptors, stilbene synthase, bibenzyl synthase, chitinases and glucanases.

Examples of known transgenic plants which comprise one or more genes which encode insecticidal resistance and express one or more toxins are the following: KnockOut® (maize), YieldGard® (maize); NuCOTN 33B® (cotton), Boligard® (cotton), NewLeaf® (potatoes), NatureGard® and Protecta®.

The following table comprises further examples of targets and principles and crop phenotypes of transgenic crops which show tolerance against pests mainly insects, mites, nematodes, virus, bacteria and diseases or are tolerant to specific herbicides or classes of herbicides.

TABLE A1

| Crop: Maize | |
|---|---|
| Effected target or expressed principle(s) | Crop phenotype/Tolerance to |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Dimboa biosynthesis (Bx1 gene) | *Helminthosporium turcicum*, *Rhopalosiphum maydis*, *Diplodia maydis*, *Ostrinia nubilalis*, *lepidoptera* sp. |
| CMIII (small basic maize seed peptide | plant pathogenes eg. *fusarium*, *alternaria*, *sclerotina* |

TABLE A1-continued

Crop: Maize

| Effected target or expressed principle(s) | Crop phenotype/Tolerance to |
|---|---|
| Corn- SAFP (zeamatin) | plant pathogenes eg. *fusarium, alternaria, sclerotina, rhizoctonia, chaetomium, phycomyces* |
| Hm1 gene | Cochliobulus |
| Chitinases | plant pathogenes |
| Glucanases | plant pathogenes |
| Coat proteins | viruses such as maize dwarf mosaic virus, maize chlorotic dwarf virus |
| *Bacillus thuringiensis* toxins, VIP 3, *Bacillus cereus* toxins, Photorabdus and Xenorhabdus toxins | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer, weevils |
| 3- Hydroxysteroid oxidase | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer, weevils |
| Peroxidase | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer,[001b] weevils |
| Aminopeptidase inhibitors eg. Leucine aminopeptidase inhibitor (LAPI) | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer, weevils |
| Limonene synthase | corn rootworms |
| Lectines | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer, weevils |
| Protease Inhibitors eg. cystatin, patatin, virgiferin, CPTI | weevils, corn rootworm |
| ribosome inactivating protein | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer, weevils |
| maize 5C9 polypeptide | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer, weevils |
| HMG-CoA reductase | *lepidoptera, coleoptera, diptera,* nematodes, eg. *ostrinia nubilalis, heliothis zea*, armyworms eg. *spodoptera frugiperda*, corn rootworms, sesamia sp., black cutworm, asian corn borer, weevils |

TABLE A2

Crop Wheat

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |

TABLE A2-continued

Crop Wheat

| Effected target or expressed principle(s) | Crop phenotype/Tolerance to |
|---|---|
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes eg *septoria* and *fusarioum* |
| glucose oxidase | plant pathogenes eg. *fusarium*, *septoria* |
| pyrrolnitrin synthesis genes | plant pathogenes eg. *fusarium*, *septoria* |
| serine/threonine kinases | plant pathogenes eg. *fusarium*, *septoria* and other diseases |
| Hypersensitive response eliciting polypeptide | plant pathogenes eg. *fusarium*, *septoria* and other diseases |
| Systemic acquires resistance (SAR) genes | viral, bacterial, fungal, nematodal pathogens |
| Chitinases | plant pathogenes |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacillus cereus* toxins, Photorabdus and Xenorhabdus toxins | *lepidoptera, coleoptera, diptera, nematodes,* |
| 3- Hydroxysteroid oxidase | *lepidoptera, coleoptera, diptera, nematodes,* |
| Peroxidase | *lepidoptera, coleoptera, diptera, nematodes,* |
| Aminopeptidase inhibitors eg. Leucine aminopeptidase inhibitor | *lepidoptera, coleoptera, diptera, nematodes,* |
| Lectines | *lepidoptera, coleoptera, diptera, nematodes, aphids* |
| Protease Inhibitors eg. cystatin, patatin, virgiferin, CPTI | *lepidoptera, coleoptera, diptera, nematodes, aphids* |
| ribosome inactivating protein | *lepidoptera, coleoptera, diptera, nematodes, aphids* |
| HMG-CoA reductase | *lepidoptera, coleoptera, diptera,* nematodes, eg. *ostrinia nubilalis, heliothis zea,* armyworms eg. *spodoptera frugiperda,* corn rootworms, sesamia sp., black cutworm, asian corn borer, weevils |

TABLE A3

Crop Barley

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |

TABLE A3-continued

Crop Barley

| Effected target or expressed principle(s) | Crop phenotype/Tolerance to |
|---|---|
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes eg *septoria* and *fusarioum* |
| glucose oxidase | plant pathogenes eg. *fusarium*, *septoria* |
| pyrrolnitrin synthesis genes | plant pathogenes eg. *fusarium*, *septoria* |
| serine/threonine kinases | plant pathogenes eg. *fusarium*, *septoria* and other diseases |
| Hypersensitive response eliciting polypeptide | plant pathogenes eg. *fusarium*, *septoria* and other diseases |
| Systemic acquires resistance (SAR) genes | viral, bacterial, fungal, nematodal pathogens |
| Chitinases | plant pathogenes |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacillus cereus* toxins, Photorabdus and Xenorhabdus toxins | *lepidoptera, coleoptera, diptera,* nematodes, |
| 3-Hydroxysteroid oxidase | *lepidoptera, coleoptera, diptera,* nematodes, |
| Peroxidase | *lepidoptera, coleoptera, diptera,* nematodes, |
| Aminopeptidase inhibitors eg. Leucine aminopeptidase inhibitor | *lepidoptera, coleoptera, diptera,* nematodes, |
| Lectines | *lepidoptera, coleoptera, diptera,* nematodes, aphids |
| Protease Inhibitors eg. cystatin, patatin, virgiferin, CPTI | *lepidoptera, coleoptera, diptera,* nematodes, aphids |
| ribosome inactivating protein | *lepidoptera, coleoptera, diptera,* nematodes, aphids |
| HMG-CoA reductase | *lepidoptera, coleoptera, diptera,* nematodes, aphids |

TABLE A4

Crop Rice

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |

TABLE A4-continued

Crop Rice

| Effected target or expressed principle(s) | Crop phenotype/Tolerance to |
| --- | --- |
| Cytochrome P450 eg. P450 SU1 | Xenobiotics and herbicides such as Sulfonylureas |
| Antifungal polypeptide AlyAFP | plant pathogenes |
| glucose oxidase | plant pathogenes |
| pyrrolnitrin synthesis genes | plant pathogenes |
| serine/threonine kinases | plant pathogenes |
| Phenylalanine ammonia lyase (PAL) | plant pathogenes eg bacterial leaf blight and rice blast, inducible |
| phytoalexins | plant pathogenes eg bacterial leaf blight and rice blast |
| B-1,3-glucanase antisense | plant pathogenes eg bacterial leaf blight and rice blast |
| receptor kinase | plant pathogenes eg bacterial leaf blight and rice blast |
| Hypersensitive response eliciting polypeptide | plant pathogenes |
| Systemic acquires resistance (SAR) genes | viral, bacterial, fungal, nematodal pathogens |
| Chitinases | plant pathogenes eg bacterial leaf blight and rice blast |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacillus cereus* toxins, Photorabdus and Xenorhabdus toxins | *lepidoptera* eg. stemborer, *coleoptera* eg rice water weevil, *diptera*, rice hoppers eg brown rice hopper |
| 3- Hydroxysteroid oxidase | *lepidoptera* eg. stemborer, *coleoptera* eg rice water weevil, *diptera*, rice hoppers eg brown rice hopper |
| Peroxidase | *lepidoptera* eg. stemborer, *coleoptera* eg rice water weevil, *diptera*, rice hoppers eg brown rice hopper |
| Aminopeptidase inhibitors eg. Leucine aminopeptidase inhibitor | *lepidoptera* eg. stemborer, *coleoptera* eg rice water weevil, *diptera*, rice hoppers eg brown rice hopper |
| Lectines | *lepidoptera* eg. stemborer, *coleoptera* eg rice water weevil, *diptera*, rice hoppers eg brown rice hopper |
| Protease Inhibitors, | *lepidoptera* eg. stemborer, *coleoptera* eg rice water weevil, *diptera*, rice hoppers eg brown rice hopper |
| ribosome inactivating protein | *lepidoptera* eg. stemborer, *coleoptera* eg rice water weevil, *diptera*, rice hoppers eg brown rice hopper |
| HMG-CoA reductase | *lepidoptera* eg. stemborer, *coleoptera* eg rice water weevil, *diptera*, rice hoppers eg brown rice hopper |

TABLE A5

Crop Soya

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |

TABLE A5-continued

Crop Soya

| Effected target or expressed principle(s) | Crop phenotype/Tolerance to |
|---|---|
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Antifungal polypeptide AlyAFP | bacterial and fungal pathogens such as *fusarium, sclerotinia*, stemrot |
| oxalate oxidase | bacterial and fungal pathogens such as *fusarium, sclerotinia*, stemrot |
| glucose oxidase | bacterial and fungal pathogens such as *fusarium, sclerotinia*, stemrot |
| pyrrolnitrin synthesis genes | bacterial and fungal pathogens such as *fusarium, sclerotinia*, stemrot |
| serine/threonine kinases | bacterial and fungal pathogens such as *fusarium, sclerotinia*, stemrot |
| Phenylalanine ammonia lyase (PAL) | bacterial and fungal pathogens such as *fusarium, sclerotinia*, stemrot |
| phytoalexins | plant pathogenes eg bacterial leaf blight and rice blast |
| B-1,3-glucanase antisense | plant pathogenes eg bacterial leaf blight and rice blast |
| receptor kinase | bacterial and fungal pathogens such as *fusarium, sclerotinia*, stemrot |
| Hypersensitive response eliciting polypeptide | plant pathogenes |
| Systemic acquires resistance (SAR) genes | viral, bacterial, fungal, nematodal pathogens |
| Chitinases | bacterial and fungal pathogens such as *fusarium, sclerotinia*, stemrot |
| Glucanases | bacterial and fungal pathogens such as *fusarium, sclerotinia*, stemrot |
| double stranded ribonuclease | viruses such as BPMV and SbMV |
| Coat proteins | viruses such as BYDV and MSMV |
| *Bacillus thuringiensis* toxins, VIP 3, *Bacillus cereus* toxins, Photorabdus and Xenorhabdus toxins | *lepidoptera, coleoptera*, aphids |
| 3- Hydroxysteroid oxidase | *lepidoptera, coleoptera*, aphids |
| Peroxidase | *lepidoptera, coleoptera*, aphids |
| Aminopeptidase inhibitors eg. Leucine aminopeptidase inhibitor | *lepidoptera, coleoptera*, aphids |
| Lectines | *lepidoptera, coleoptera*, aphids |
| Protease Inhibitors eg virgiferin | *lepidoptera, coleoptera*, aphids |
| ribosome inactivating protein | *lepidoptera, coleoptera*, aphids |
| HMG-CoA reductase | *lepidoptera, coleoptera*, aphids |
| Barnase | nematodes eg root knot nematodes and cyst nematodes |
| Cyst nematode hatching stimulus | cyst nematodes |
| Antifeeding principles | nematodes eg root knot nematodes and cyst nematodes |

TABLE A6

Crop Potatoes

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |

TABLE A6-continued

Crop Potatoes

| Effected target or expressed principle(s) | Crop phenotype/Tolerance to |
|---|---|
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | blackspot bruise |
| Metallothionein | bacterial and fungal pathogens such as *phytophtora* |
| Ribonuclease | *Phytophtora, Verticillium, Rhizoctonia* |
| Antifungal polypeptide AlyAFP | bacterial and fungal pathogens such as *phytophtora* |
| oxalate oxidase | bacterial and fungal pathogens such as *Phytophtora, Verticillium, Rhizoctonia* |
| glucose oxidase | bacterial and fungal pathogens such as *Phytophtora, Verticillium, Rhizoctonia* |
| pyrrolnitrin synthesis genes | bacterial and fungal pathogens such as *Phytophtora, Verticillium, Rhizoctonia* |
| serine/threonine kinases | bacterial and fungal pathogens such as *Phytophtora, Verticillium, Rhizoctonia* |
| Cecropin B | bacteria such as corynebacterium sepedonicum, Erwinia carotovora |
| Phenylalanine ammonia lyase (PAL) | bacterial and fungal pathogens such as *Phytophtora, Verticillium, Rhizoctonia* |
| phytoalexins | bacterial and fungal pathogens such as *Phytophtora, Verticillium, Rhizoctonia* |
| B-1,3-glucanase antisense | bacterial and fungal pathogens such as *Phytophtora, Verticillium, Rhizoctonia* |
| receptor kinase | bacterial and fungal pathogens such as *Phytophtora, Verticillium, Rhizoctonia* |
| Hypersensitive response eliciting polypeptide | bacterial and fungal pathogens such as *Phytophtora, Verticillium, Rhizoctonia* |
| Systemic acquires resistance (SAR) genes | viral, bacterial, fungal, nematodal pathogens |
| Chitinases | bacterial and fungal pathogens such as *Phytophtora, Verticillium, Rhizoctonia* |
| Barnase | bacterial and fungal pathogens such as *Phytophtora, Verticillium, Rhizoctonia* |
| Disease resistance response gene 49 | bacterial and fungal pathogens such as *Phytophtora, Verticillium, Rhizoctonia* |
| trans aldolase antisense | blackspots |
| Glucanases | bacterial and fungal pathogens such as *Phytophtora, Verticillium, Rhizoctonia* |
| double stranded ribonuclease | viruses such as PLRV, PVY and TRV |
| Coat proteins | viruses such as PLRV, PVY and TRV |
| 17 kDa or 60 kDa protein | viruses such as PLRV, PVY and TRV |
| Nuclear inclusion proteins eg. a or b | viruses such as PLRV, PVY and TRV |
| Pseudoubiquitin | viruses such as PLRV, PVY and TRV |
| Replicase | viruses such as PLRV, PVY and TRV |
| *Bacillus thuringiensis* toxins, VIP 3, *Bacillus cereus* toxins, Photorabdus and Xenorhabdus toxins | *coleoptera* eg colorado potato beetle, aphids |
| 3-Hydroxysteroid oxidase | *coleoptera* eg colorado potato beetle, aphids |
| Peroxidase | *coleoptera* eg colorado potato beetle, aphids |
| Aminopeptidase inhibitors eg. Leucine aminopeptidase inhibitor | *coleoptera* eg colorado potato beetle, aphids |
| stilbene synthase | *coleoptera* eg colorado potato beetle, aphids |
| Lectines | *coleoptera* eg colorado potato beetle, aphids |
| Protease Inhibitors eg cystatin, patatin | *coleoptera* eg colorado potato beetle, aphids |

TABLE A6-continued

Crop Potatoes

| Effected target or expressed principle(s) | Crop phenotype/Tolerance to |
| --- | --- |
| ribosome inactivating protein | *coleoptera* eg colorado potato beetle, aphids |
| HMG-CoA reductase | *coleoptera* eg colorado potato beetle, aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A7

Crop Tomatoes

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | blackspot bruise |
| Metallothionein | bacterial and fungal pathogens such as *phytophtora* |
| Ribonuclease | *Phytophtora, Verticillium, Rhizoctonia* |
| Antifungal polypeptide AlyAFP | bacterial and fungal pathogens such as bacterial speck, *fusarium*, soft rot, powdery mildew, crown rot, leaf mould etc. |
| oxalate oxidase | bacterial and fungal pathogens such as bacterial speck, *fusarium*, soft rot, powdery mildew, crown rot, leaf mould etc. |
| glucose oxidase | bacterial and fungal pathogens such as bacterial speck, *fusarium*, soft rot, powdery mildew, crown rot, leaf mould etc. |
| pyrrolnitrin synthesis genes | bacterial and fungal pathogens such as bacterial speck, *fusarium*, soft rot, powdery mildew, crown rot, leaf mould etc. |
| serine/threonine kinases | bacterial and fungal pathogens such as bacterial speck, *fusarium*, soft rot, powdery mildew, crown rot, leaf mould etc. |
| Cecropin B | bacterial and fungal pathogens such as bacterial speck, *fusarium*, soft rot, powdery mildew, crown rot, leaf mould etc. |

TABLE A7-continued

Crop Tomatoes

| Effected target or expressed principle(s) | Crop phenotype/Tolerance to |
|---|---|
| Phenylalanine ammonia lyase (PAL) | bacterial and fungal pathogens such as bacterial speck, *fusarium*, soft rot, powdery mildew, crown rot, leaf mould etc. |
| Cf genes eg. Cf 9 Cf5 Cf4 Cf2 | leaf mould |
| Osmotin | alternaria solani |
| Alpha Hordothionin | bacteria |
| Systemin | bacterial and fungal pathogens such as bacterial speck, *fusarium*, soft rot, powdery mildew, crown rot, leaf mould etc. |
| Polygalacturonase inhibitors | bacterial and fungal pathogens such as bacterial speck, *fusarium*, soft rot, powdery mildew, crown rot, leaf mould etc. |
| Prf regulatory gene | bacterial and fungal pathogens such as bacterial speck, *fusarium*, soft rot, powdery mildew, crown rot, leaf mould etc. |
| 12 *Fusarium* resistance locus | *fusarium* |
| phytoalexins | bacterial and fungal pathogens such as bacterial speck, *fusarium*, soft rot, powdery mildew, crown rot, leaf mould etc. |
| B-1,3-glucanase antisense | bacterial and fungal pathogens such as bacterial speck, *fusarium*, soft rot, powdery mildew, crown rot, leaf mould etc. |
| receptor kinase | bacterial and fungal pathogens such as bacterial speck, *fusarium*, soft rot, powdery mildew, crown rot, leaf mould etc. |
| Hypersensitive response eliciting polypeptide | bacterial and fungal pathogens such as bacterial speck, *fusarium*, soft rot, powdery mildew, crown rot, leaf mould etc. |
| Systemic acquires resistance (SAR) genes | viral, bacterial, fungal, nematodal pathogens |
| Chitinases | bacterial and fungal pathogens such as bacterial speck, *fusarium*, soft rot, powdery mildew, crown rot, leaf mould etc. |
| Barnase | bacterial and fungal pathogens such as bacterial speck, *fusarium*, soft rot, powdery mildew, crown rot, leaf mould etc. |
| Glucanases | bacterial and fungal pathogens such as bacterial speck, *fusarium*, soft rot, powdery mildew, crown rot, leaf mould etc. |
| double stranded ribonuclease | viruses such as PLRV, PVY and ToMoV |
| Coat proteins | viruses such as PLRV, PVY and ToMoV |
| 17 kDa or 60 kDa protein | viruses such as PLRV, PVY and ToMoV |
| Nuclear inclusion proteins eg. a or b or | viruses such as PLRV, PVY and ToMoV |
| Nucleoprotein | TRV |
| Pseudoubiquitin | viruses such as PLRV, PVY and ToMoV |
| Replicase | viruses such as PLRV, PVY and ToMoV |
| *Bacillus thuringiensis* toxins, VIP 3, *Bacillus cereus* toxins, Photorabdus and Xenorhabdus toxins | lepidoptera eg *heliothis*, whiteflies aphids |
| 3- Hydroxysteroid oxidase | lepidoptera eg *heliothis*, whiteflies aphids |
| Peroxidase | lepidoptera eg *heliothis*, whiteflies aphids |
| Aminopeptidase inhibitors eg. Leucine aminopeptidase inhibitor | lepidoptera eg *heliothis*, whiteflies aphids |
| Lectines | lepidoptera eg *heliothis*, whiteflies aphids |
| Protease Inhibitors eg cystatin, patatin | lepidoptera eg *heliothis*, whiteflies aphids |
| ribosome inactivating protein | lepidoptera eg *heliothis*, whiteflies aphids |
| stilbene synthase | lepidoptera eg *heliothis*, whiteflies aphids |
| HMG-CoA reductase | lepidoptera eg *heliothis*, whiteflies aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A8

Crop Peppers

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens |
| Metallothionein | bacterial and fungal pathogens |
| Ribonuclease | bacterial and fungal pathogens |
| Antifungal polypeptide AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| Cecropin B | bacterial and fungal pathogens rot, leaf mould etc. |
| Phenylalanine ammonia lyase (PAL) | bacterial and fungal pathogens |
| Cf genes eg. Cf 9 Cf5 Cf4 Cf2 | bacterial and fungal pathogens |
| Osmotin | bacterial and fungal pathogens |
| Alpha Hordothionin | bacterial and fungal pathogens |
| Systemin | bacterial and fungal pathogens |
| Polygalacturonase inhibitors | bacterial and fungal pathogens |
| Prt regulatory gene | bacterial and fungal pathogens |
| 12 *Fusarium* resistance locus | *fusarium* |
| phytoalexins | bacterial and fungal pathogens |
| B-1,3-glucanase antisense | bacterial and fungal pathogens |
| receptor kinase | bacterial and fungal pathogens |
| Hypersensitive response eliciting polypeptide | bacterial and fungal pathogens |
| Systemic acquires resistance (SAR) genes | viral, bacterial, fungal, nematodal pathogens |
| Chitinases | bacterial and fungal pathogens |
| Barnase | bacterial and fungal pathogens |
| Glucanases | bacterial and fungal pathogens |
| double stranded ribonuclease | viruses such as CMV, TEV |
| Coat proteins | viruses such as CMV, TEV |
| 17 kDa or 60 kDa protein | viruses such as CMV, TEV |
| Nuclear inclusion proteins eg. a or b or Nucleoprotein | viruses such as CMV, TEV |
| Pseudoubiquitin | viruses such as CMV, TEV |
| Replicase | viruses such as CMV, TEV |
| *Bacillus thuringiensis* toxins, VIP 3, *Bacillus cereus* toxins, Photorabdus and Xenorhabdus toxins | *lepidoptera*, whiteflies aphids |
| 3- Hydroxysteroid oxidase | *lepidoptera*, whiteflies aphids |
| Peroxidase | *lepidoptera*, whiteflies aphids |
| Aminopeptidase inhibitors eg. Leucine aminopeptidase inhibitor | *lepidoptera*, whiteflies aphids |
| Lectines | *lepidoptera*, whiteflies aphids |
| Protease Inhibitors eg cystatin, patatin | *lepidoptera*, whiteflies aphids |
| ribosome inactivating protein | *lepidoptera*, whiteflies aphids |
| stilbene synthase | *lepidoptera*, whiteflies aphids |
| HMG-CoA reductase | *lepidoptera*, whiteflies aphids |
| Cyst nematode hatching stimulus | cyst nematodes |

TABLE A8-continued

Crop Peppers

| Effected target or expressed principle(s) | Crop phenotype/Tolerance to |
|---|---|
| Barnase | nematodes eg root knot nematodes and cyst nematodes |
| Antifeeding principles | nematodes eg root knot nematodes and cyst nematodes |

TABLE A9

Crop Grapes

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens like Botrytis and powdery mildew |
| Metallothionein | bacterial and fungal pathogens like Botrytis and powdery mildew |
| Ribonuclease | bacterial and fungal pathogens like Botrytis and powdery mildew |
| Antifungal polypeptide AlyAFP | bacterial and fungal pathogens like Botrytis and powdery mildew |
| oxalate oxidase | bacterial and fungal pathogens like Botrytis and powdery mildew |
| glucose oxidase | bacterial and fungal pathogens like Botrytis and powdery mildew |
| pyrrolnitrin synthesis genes | bacterial and fungal pathogens like Botrytis and powdery mildew |
| serine/threonine kinases | bacterial and fungal pathogens like Botrytis and powdery mildew |
| Cecropin B | bacterial and fungal pathogens like Botrytis and powdery mildew |
| Phenylalanine ammonia lyase (PAL) | bacterial and fungal pathogens like Botrytis and powdery mildew |
| Cf genes eg. Cf 9 Cf5 Cf4 Cf2 | bacterial and fungal pathogens like Botrytis and powdery mildew |
| Osmotin | bacterial and fungal pathogens like Botrytis and powdery mildew |
| Alpha Hordothionin | bacterial and fungal pathogens like Botrytis and powdery mildew |
| Systemin | bacterial and fungal pathogens like Botrytis and powdery mildew |
| Polygalacturonase inhibitors | bacterial and fungal pathogens like Botrytis and powdery mildew |
| Prf regulatory gene | bacterial and fungal pathogens like Botrytis and powdery mildew |
| phytoalexins | bacterial and fungal pathogens like Botrytis and powdery mildew |

TABLE A9-continued

Crop Grapes

| Effected target or expressed principle(s) | Crop phenotype/Tolerance to |
|---|---|
| B-1,3-glucanase antisense | bacterial and fungal pathogens like Botrytis and powdery mildew |
| receptor kinase | bacterial and fungal pathogens like Botrytis and powdery mildew |
| Hypersensitive response eliciting polypeptide | bacterial and fungal pathogens like Botrytis and powdery mildew |
| Systemic acquires resistance (SAR) genes | viral, bacterial, fungal, nematodal pathogens |
| Chitinases | bacterial and fungal pathogens like Botrytis and powdery mildew |
| Barnase | bacterial and fungal pathogens like Botrytis and powdery mildew |
| Glucanases | bacterial and fungal pathogens like Botrytis and powdery mildew |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| *Bacillus thuringiensis* toxins, VIP 3, *Bacillus cereus* toxins, Photorabdus and Xenorhabdus toxins | *lepidoptera*, aphids |
| 3- Hydroxysteroid oxidase | *lepidoptera*, aphids |
| Peroxidase | *lepidoptera*, aphids |
| Aminopeptidase inhibitors eg. Leucine aminopeptidase inhibitor | *lepidoptera*, aphids |
| Lectines | *lepidoptera*, aphids |
| Protease Inhibitors eg cystatin, patatin | *lepidoptera*, aphids |
| ribosome inactivating protein | *lepidoptera*, aphids |
| stilbene synthase | *lepidoptera*, aphids, diseases |
| HMG-CoA reductase | *lepidoptera*, aphids |
| Cyst nematode hatching stimulus | cyst nematodes |
| Barnase | nematodes eg root knot nematodes and cyst nematodes or general diseases |
| CBI | root knot nematodes |
| Antifeeding principles | nematodes eg root knot nematodes or root cyst nematodes |

TABLE A10 crop Oil Seed rape

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |

TABLE A10-continued crop Oil Seed rape

| Effected target or expressed principle(s) | Crop phenotype/Tolerance to |
|---|---|
| Polyphenol oxidase or Polyphenol oxidase antisense | bacterial and fungal pathogens like *Cylindrosporium, Phoma, Sclerotinia* |
| Metallothionein | bacterial and fungal pathogens like *Cylindrosporium, Phoma, Sclerotinia* |
| Ribonuclease | bacterial and fungal pathogens like *Cylindrosporium, Phoma, Sclerotinia* |
| Antifungal polypeptide AlyAFP | bacterial and fungal pathogens like *Cylindrosporium, Phoma, Sclerotinia* |
| oxalate oxidase | bacterial and fungal pathogens like *Cylindrosporium, Phoma, Sclerotinia* |
| glucose oxidase | bacterial and fungal pathogens like *Cylindrosporium, Phoma, Sclerotinia* |
| pyrrolnitrin synthesis genes | bacterial and fungal pathogens like *Cylindrosporium, Phoma, Sclerotinia* |
| serine/threonine kinases | bacterial and fungal pathogens like *Cylindrosporium, Phoma, Sclerotinia* |
| Cecropin B | bacterial and fungal pathogens like *Cylindrosporium, Phoma, Sclerotinia* |
| Phenylalanine ammonia lyase (PAL) | bacterial and fungal pathogens like *Cylindrosporium, Phoma, Sclerotinia* |
| Cf genes eg. Cf 9 Cf5 Cf4 Cf2 | bacterial and fungal pathogens like *Cylindrosporium, Phoma, Sclerotinia* |
| Osmotin | bacterial and fungal pathogens like *Cylindrosporium, Phoma, Sclerotinia* |
| Alpha Hordothionin | bacterial and fungal pathogens like *Cylindrosporium, Phoma, Sclerotinia* |
| Systemin | bacterial and fungal pathogens like *Cylindrosporium, Phoma, Sclerotinia* |
| Polygalacturonase inhibitors | bacterial and fungal pathogens like *Cylindrosporium, Phoma, Sclerotinia* |
| Prf regulatory gene | bacterial and fungal pathogens like *Cylindrosporium, Phoma, Sclerotinia* |
| phytoalexins | bacterial and fungal pathogens like *Cylindrosporium, Phoma, Sclerotinia* |
| B-1,3-glucanase antisense | bacterial and fungal pathogens like *Cylindrosporium, Phoma, Sclerotinia* |
| receptor kinase | bacterial and fungal pathogens like *Cylindrosporium, Phoma, Sclerotinia* |
| Hypersensitive response eliciting polypeptide | bacterial and fungal pathogens like *Cylindrosporium, Phoma, Sclerotinia* |
| Systemic acquires resistance (SAR) genes | viral, bacterial, fungal, nematodal pathogens |
| Chitinases | bacterial and fungal pathogens like *Cylindrosporium, Phoma, Sclerotinia* |
| Barnase | bacterial and fungal pathogens like *Cylindrosporium, Phoma, Sclerotinia*, nematodes |
| Glucanases | bacterial and fungal pathogens like *Cylindrosporium, Phoma, Sclerotinia* |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| *Bacillus thuringiensis* toxins, VIP 3, *Bacillus cereus* toxins, Photorabdus and Xenorhabdus toxins | lepidoptera, aphids |
| 3- Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease Inhibitors eg cystatin, patatin, CPTI | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes |
| CBI | root knot nematodes |

TABLE A10-continued crop Oil Seed rape

| Effected target or expressed principle(s) | Crop phenotype/Tolerance to |
|---|---|
| Antifeeding principles induced at a nematode feeding site | nematodes eg root knot nematodes, root cyst nematodes |

TABLE A11

Crop Brassica vegetable (cabbage, brussel sprouts, broccoli etc.)

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinil |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens |
| Metallothionein | bacterial and fungal pathogens |
| Ribonuclease | bacterial and fungal pathogens |
| Antifungal polypeptide AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| Cecropin B | bacterial and fungal pathogens |
| Phenylalanine ammonia lyase (PAL) | bacterial and fungal pathogens |
| Cf genes eg. Cf 9 Cf5 Cf4 Cf2 | bacterial and fungal pathogens |
| Osmotin | bacterial and fungal pathogens |
| Alpha Hordothionin | bacterial and fungal pathogens |
| Systemin | bacterial and fungal pathogens |
| Polygalacturonase inhibitors | bacterial and fungal pathogens |
| Prf regulatory gene | bacterial and fungal pathogens |
| phytoalexins | bacterial and fungal pathogens |
| B-1,3-glucanase antisense | bacterial and fungal pathogens |
| receptor kinase | bacterial and fungal pathogens |
| Hypersensitive response eliciting polypeptide | bacterial and fungal pathogens |
| Systemic acquires resistance (SAR) genes | viral, bacterial, fungal, nematodal pathogens |
| Chitinases | bacterial and fungal pathogens |
| Barnase | bacterial and fungal pathogens |
| Glucanases | bacterial and fungal pathogens |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| *Bacillus thuringiensis* toxins, VIP 3, *Bacillus cereus* toxins, Photorabdus and Xenorhabdus toxins | lepidoptera, aphids |
| 3-Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease Inhibitors eg cystatin, patatin, CPTI | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A12

Crop Pome fruits eg apples, pears

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |

TABLE A12-continued

Crop Pome fruits eg apples, pears

| Effected target or expressed principle(s) | Crop phenotype/Tolerance to |
|---|---|
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens like apple scab or fireblight |
| Metallothionein | bacterial and fungal pathogens like apple scab or fireblight |
| Ribonuclease | bacterial and fungal pathogens like apple scab or fireblight |
| Antifungal polypeptide AlyAFP | bacterial and fungal pathogens like apple scab or fireblight |
| oxalate oxidase | bacterial and fungal pathogens like apple scab or fireblight |
| glucose oxidase | bacterial and fungal pathogens like apple scab or fireblight |
| pyrrolnitrin synthesis genes | bacterial and fungal pathogens like apple scab or fireblight |
| serine/threonine kinases | bacterial and fungal pathogens like apple scab or fireblight |
| Cecropin B | bacterial and fungal pathogens like apple scab or fireblight |
| Phenylalanine ammonia lyase (PAL) | bacterial and fungal pathogens like apple scab or fireblight |
| Cf genes eg. Cf 9 Cf5 Cf4 Cf2 | bacterial and fungal pathogens like apple scab or fireblight |
| Osmotin | bacterial and fungal pathogens like apple scab or fireblight |
| Alpha Hordothionin | bacterial and fungal pathogens like apple scab or fireblight |
| Systemin | bacterial and fungal pathogens like apple scab or fireblight |
| Polygalacturonase inhibitors | bacterial and fungal pathogens like apple scab or fireblight |
| Prf regulatory gene | bacterial and fungal pathogens like apple scab or fireblight |
| phytoalexins | bacterial and fungal pathogens like apple scab or fireblight |
| B-1,3-glucanase antisense | bacterial and fungal pathogens like apple scab or fireblight |
| receptor kinase | bacterial and fungal pathogens like apple scab or fireblight |
| Hypersensitive response eliciting polypeptide | bacterial and fungal pathogens like apple scab or fireblight |
| Systemic acquires resistance (SAR) genes | viral, bacterial, fungal, nematodal pathogens |
| Lytic protein | bacterial and fungal pathogens like apple scab or fireblight |
| Lysozym | bacterial and fungal pathogens like apple scab or fireblight |
| Chitinases | bacterial and fungal pathogens like apple scab or fireblight |
| Barnase | bacterial and fungal pathogens like apple scab or fireblight |
| Glucanases | bacterial and fungal pathogens like apple scab or fireblight |
| double stranded ribonuclease | viruses |
| Coat proteins | viruses |
| 17 kDa or 60 kDa protein | viruses |
| Nuclear inclusion proteins eg. a or b or Nucleoprotein | viruses |

TABLE A12-continued

Crop Pome fruits eg apples, pears

| Effected target or expressed principle(s) | Crop phenotype/Tolerance to |
| --- | --- |
| Pseudoubiquitin | viruses |
| Replicase | viruses |
| *Bacillus thuringiensis* toxins, VIP 3, *Bacillus cereus* toxins, Photorabdus and Xenorhabdus toxins | lepidoptera, aphids, mites |
| 3-Hydroxysteroid oxidase | lepidoptera, aphids, mites |
| Peroxidase | lepidoptera, aphids, mites |
| Aminopeptidase inhibitors eg. Leucine aminopeptidase inhibitor | lepidoptera, aphids, mites |
| Lectines | lepidoptera, aphids, mites |
| Protease Inhibitors eg cystatin, patatin, CPTI | lepidoptera, aphids, mites |
| ribosome inactivating protein | lepidoptera, aphids, mites |
| stilbene synthase | lepidoptera, aphids, diseases, mites |
| HMG-CoA reductase | lepidoptera, aphids, mites |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A13

Crop Melons

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and loxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens like phytophtora |
| Metallothionein | bacterial or fungal pathogens like phytophtora |
| Ribonuclease | bacterial or fungal pathogens like phytophtora |
| Antifungal polypeptide AlyAFP | bacterial or fungal pathogens like phytophtora |
| oxalate oxidase | bacterial or fungal pathogens like phytophtora |
| glucose oxidase | bacterial or fungal pathogens like phytophtora |
| pyrrolnitrin synthesis genes | bacterial or fungal pathogens like phytophtora |
| serine/threonine kinases | bacterial or fungal pathogens like phytophtora |
| Cecropin B | bacterial or fungal pathogens like phytophtora |
| Phenylalanine ammonia lyase (PAL) | bacterial or fungal pathogens like phytophtora |
| Cf genes eg. Cf 9 Cf5 Cf4 Cf2 | bacterial or fungal pathogens like phytophtora |
| Osmotin | bacterial or fungal pathogens like phytophtora |
| Alpha Hordothionin | bacterial or fungal pathogens like phytophtora |
| Systemin | bacterial or fungal pathogens like phytophtora |
| Polygalacturonase inhibitors | bacterial or fungal pathogens like phytophtora |

TABLE A13-continued

Crop Melons

| Effected target or expressed principle(s) | Crop phenotype/Tolerance to |
| --- | --- |
| Prf regulatory gene | bacterial or fungal pathogens like phytophtora |
| phytoalexins | bacterial or fungal pathogens like phytophtora |
| B-1,3-glucanase antisense | bacterial or fungal pathogens like phytophtora |
| receptor kinase | bacterial or fungal pathogens like phytophtora |
| Hypersensitive response eliciting polypeptide | bacterial or fungal pathogens like phytophtora |
| Systemic acquires resistance (SAR) genes | viral, bacterial, fungal, nematodal pathogens |
| Lytic protein | bacterial or fungal pathogens like phytophtora |
| Lysozym | bacterial or fungal pathogens like phytophtora |
| Chitinases | bacterial or fungal pathogens like phytophtora |
| Barnase | bacterial or fungal pathogens like phytophtora |
| Glucanases | bacterial or fungal pathogens like phytophtora |
| double stranded ribonuclease | viruses as CMV,, PRSV, WMV2, SMV, ZYMV |
| Coat proteins | viruses as CMV,, PRSV, WMV2, SMV, ZYMV |
| 17 kDa or 60 kDa protein | viruses as CMV,, PRSV, WMV2, SMV, ZYMV |
| Nuclear inclusion proteins eg. a or b or Nucleoprotein | viruses as CMV,, PRSV, WMV2, SMV, ZYMV |
| Pseudoubiquitin | viruses as CMV,, PRSV, WMV2, SMV, ZYMV |
| Replicase | viruses as CMV,, PRSV, WMV2, SMV, ZYMV |
| *Bacillus thuringiensis* toxins, VIP 3, *Bacillus cereus* toxins, Photorabdus and Xenorhabdus toxins | lepidoptera, aphids, mites |
| 3-Hydroxysteroid oxidase | lepidoptera, aphids, mites, whitefly |
| Peroxidase | lepidoptera, aphids, mites, whitefly |
| Aminopeptidase inhibitors eg. Leucine aminopeptidase inhibitor | lepidoptera, aphids, mites, whitefly |
| Lectines | lepidoptera, aphids, mites, whitefly |
| Protease Inhibitors eg cystatin, patatin, CPTI, virgiferin | lepidoptera, aphids, mites, whitefly |
| ribosome inactivating protein | lepidoptera, aphids, mites, whitefly |
| stilbene synthase | lepidoptera, aphids, mites, whitefly |
| HMG-CoA reductase | lepidoptera, aphids, mites, whitefly |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A14

Crop Banana

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |

TABLE A14-continued

Crop Banana

| Effected target or expressed principle(s) | Crop phenotype/Tolerance to |
|---|---|
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as Banana bunchy top virus (BBTV) |
| Coat proteins | viruses as Banana bunchy top virus (BBTV) |
| 17 kDa or 60 kDa protein | viruses as Banana bunchy top virus (BBTV) |
| Nuclear inclusion proteins eg. a or b or Nucleoprotein | viruses as Banana bunchy top virus (BBTV) |
| Pseudoubiquitin | viruses as Banana bunchy top virus (BBTV) |
| Replicase | viruses as Banana bunchy top virus (BBTV) |
| *Bacillus thuringiensis* toxins, VIP 3, *Bacillus cereus* toxins, Photorabdus and Xenorhabdus toxins | lepidoptera, aphids, mites, nematodes |
| 3-Hydroxysteroid oxidase | lepidoptera, aphids, mites, nematodes |
| Peroxidase | lepidoptera, aphids, mites, nematodes |
| Aminopeptidase inhibitors eg. Leucine aminopeptidase inhibitor | lepidoptera, aphids, mites, nematodes |
| Lectines | lepidoptera, aphids, mites, nematodes |
| Protease Inhibitors eg cystatin, patatin, CPTI, virgiferin | lepidoptera, aphids, mites, nematodes |
| ribosome inactivating protein | lepidoptera, aphids, mites, nematodes |
| stilbene synthase | lepidoptera, aphids, mites, nematodes |
| HMG-CoA reductase | lepidoptera, aphids, mites, nematodes |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A15

Crop Cotton

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |

TABLE A15-continued

Crop Cotton

| Effected target or expressed principle(s) | Crop phenotype/Tolerance to |
| --- | --- |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as wound tumor virus (WTV) |
| Coat proteins | viruses as wound tumor virus (WTV) |
| 17 kDa or 60 kDa protein | viruses as wound tumor virus (WTV) |
| Nuclear inclusion proteins eg. a or b or Nucleoprotein | viruses as wound tumor virus (WTV) |
| Pseudoubiquitin | viruses as wound tumor virus (WTV) |
| Replicase | viruses as wound tumor virus (WTV) |
| Bacillus thuringiensis toxins, VIP 3, Bacillus cereus toxins, Photorabdus and Xenorhabdus toxins | lepidoptera, aphids, mites, nematodes, whitefly |
| 3-Hydroxysteroid oxidase | lepidoptera, aphids, mites, nematodes, whitefly |
| Peroxidase | lepidoptera, aphids, mites, nematodes, whitefly |
| Aminopeptidase inhibitors eg. Leucine aminopeptidase inhibitor | lepidoptera, aphids, mites, nematodes, whitefly |
| Lectines | lepidoptera, aphids, mites, nematodes, whitefly |
| Protease Inhibitors eg cystatin, patatin, CPTI, virgiferin | lepidoptera, aphids, mites, nematodes, whitefly |
| ribosome inactivating protein | lepidoptera, aphids, mites, nematodes, whitefly |
| stilbene synthase | lepidoptera, aphids, mites, nematodes, whitefly |
| HMG-CoA reductase | lepidoptera, aphids, mites, nematodes, whitefly |
| Cyst nematode hatching stimulus | cyst nematodes |
| Barnase | nematodes eg root knot nematodes and cyst nematodes |

TABLE A15-continued

Crop Cotton

| Effected target or expressed principle(s) | Crop phenotype/Tolerance to |
|---|---|
| CBI | root knot nematodes |
| Antifeeding principles induced at a nematode feeding site | nematodes eg root knot nematodes, root cyst nematodes |

TABLE A16

Crop Sugarcane

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens eg clavibacter |
| Chitinases | bacterial or fungal pathogens |
| Barnase | bacterial or fungal pathogens |
| Glucanases | bacterial or fungal pathogens |
| double stranded ribonuclease | viruses as SCMV, SrMV |
| Coat proteins | viruses as SCMV, SrMV |
| 17 kDa or 60 kDa protein | viruses as SCMV, SrMV |
| Nuclear inclusion proteins eg. a or b or Nucleoprotein | viruses as SCMV, SrMV |
| Pseudoubiquitin | viruses as SCMV, SrMV |
| Replicase | viruses as SCMV, SrMV |
| *Bacillus thuringiensis* toxins, VIP 3, *Bacillus cereus* toxins, Photorabdus and Xenorhabdus toxins | lepidoptera, aphids, mites, nematodes, whitefly, beetles eg mexican rice borer |

TABLE A16-continued

Crop Sugarcane

| Effected target or expressed principle(s) | Crop phenotype/Tolerance to |
| --- | --- |
| 3-Hydroxysteroid oxidase | lepidoptera, aphids, mites, nematodes, whitefly, beetles eg mexican rice borer |
| Peroxidase | lepidoptera, aphids, mites, nematodes, whitefly, beetles eg mexican rice borer |
| Aminopeptidase inhibitors eg. Leucine aminopeptidase inhibitor | lepidoptera, aphids, mites, nematodes, whitefly, beetles eg mexican rice borer |
| Lectines | lepidoptera, aphids, mites, nematodes, whitefly, beetles eg mexican rice borer |
| Protease Inhibitors eg cystatin, patatin, CPTI, virgiferin | lepidoptera, aphids, mites, nematodes, whitefly, beetles eg mexican rice borer |
| ribosome inactivating protein | lepidoptera, aphids, mites, nematodes, whitefly, beetles eg mexican rice borer |
| stilbene synthase | lepidoptera, aphids, mites, nematodes, whitefly, beetles eg mexican rice borer |
| HMG-CoA reductase | lepidoptera, aphids, mites, nematodes, whitefly, beetles eg mexican rice borer |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A17

Crop Sunflower

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens eg sclerotinia |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |

TABLE A17-continued

Crop Sunflower

| Effected target or expressed principle(s) | Crop phenotype/Tolerance to |
|---|---|
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as CMV, TMV |
| Coat proteins | viruses as CMV, TMV |
| 17 kDa or 60 kDa protein | viruses as CMV, TMV |
| Nuclear inclusion proteins eg. a or b or Nucleoprotein | viruses as CMV, TMV |
| Pseudoubiquitin | viruses as CMV, TMV |
| Replicase | viruses as CMV, TMV |
| Bacillus thuringiensis toxins, VIP 3, Bacillus cereus toxins, Photorabdus and Xenorhabdus toxins | lepidoptera, aphids, mites, nematodes, whitefly, beetles |
| 3-Hydroxysteroid oxidase | lepidoptera, aphids, mites, nematodes, whitefly, beetles |
| Peroxidase | lepidoptera, aphids, mites, nematodes, whitefly, beetles |
| Aminopeptidase inhibitors eg. Leucine aminopeptidase inhibitor | lepidoptera, aphids, mites, nematodes, whitefly, beetles |
| Lectines | lepidoptera, aphids, mites, nematodes, whitefly, beetles |
| Protease Inhibitors eg cystatin, patatin, CPTI, virgiferin | lepidoptera, aphids, mites, nematodes, whitefly, beetles |
| ribosome inactivating protein | lepidoptera, aphids, mites, nematodes, whitefly, beetles |
| stilbene synthase | lepidoptera, aphids, mites, nematodes, whitefly, beetles |
| HMG-CoA reductase | lepidoptera, aphids, mites, nematodes, whitefly, beetles |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A18

Crop Sugarbeet, Beet root

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens eg sclerotinia |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |

TABLE A18-continued

Crop Sugarbeet, Beet root

| Effected target or expressed principle(s) | Crop phenotype/Tolerance to |
|---|---|
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| AX + WIN proteins | bacterial or fungal pathogens like *Cercospora beticola* |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as BNYVV |
| Coat proteins | viruses as BNYVV |
| 17 kDa or 60 kDa protein | viruses as BNYVV |
| Nuclear inclusion proteins eg. a or b or Nucleoprotein | viruses as BNYVV |
| Pseudoubiquitin | viruses as BNYVV |
| Replicase | viruses as BNYVV |
| *Bacillus thuringiensis* toxins, VIP 3, *Bacillus cereus* toxins, Photorabdus and Xenorhabdus toxins | lepidoptera, aphids, mites, nematodes, whitefly, beetles, rootflies |
| 3-Hydroxysteroid oxidase | lepidoptera, aphids, mites, nematodes, whitefly, beetles, rootflies |
| Peroxidase | lepidoptera, aphids, mites, nematodes, whitefly, beetles, rootflies |
| Aminopeptidase inhibitors eg. Leucine aminopeptidase inhibitor | lepidoptera, aphids, mites, nematodes, whitefly, beetles, rootflies |
| Lectines | lepidoptera, aphids, mites, nematodes, whitefly, beetles, rootflies |
| Protease Inhibitors eg cystatin, patatin, CPTI, virgiferin | lepidoptera, aphids, mites, nematodes, whitefly, beetles, rootflies |
| ribosome inactivating protein | lepidoptera, aphids, mites, nematodes, whitefly, beetles, rootflies |
| stilbene synthase | lepidoptera, aphids, mites, nematodes, whitefly, beetles, rootflies |
| HMG-CoA reductase | lepidoptera, aphids, mites, nematodes, whitefly, beetles, rootflies |
| Cyst nematode hatching stimulus | cyst nematodes |
| Barnase | nematodes eg root knot nematodes and cyst nematodes |
| Beet cyst nematode resistance locus | cyst nematodes |
| CBI | root knot nematodes |
| Antifeeding principles induced at a nematode feeding site | nematodes eg root knot nematodes, root cyst nematodes |

The abovementioned animal pests which can be controlled by the method according to the invention (A) include, for example, insects, representatives of the order acarina and representatives of the class nematoda; especially from the order Lepidoptera *Acleris* spp., *Adoxophyes* spp., especially *Adoxophyes reticulana; Aegeria* spp., *Agrotis* spp., especially *Agrotis spinifera; Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., especially *Cydia pomonella; Diatraea* spp., *Diparopsis castanea, Earias* spp., *Ephestia* spp., especially *E. Khüniella; Eucosma* spp., *Eupoecilia ambiguella, Euproctis* spp., *Euxoa* spp., *Grapholita* spp., *Hedya nubiferana, Heliothis* spp., especially *H. virescens* and *H. zea; Hellula undalis, Hyphantria cunea, Keiferia lycopersicella, Leucoptera scitella, Lithocollethis* spp., *Lobesia* spp., *Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora* spp., *Phthorimaea operculella, Pieris rapae, Pieris* spp., *Plutella xylostella, Prays* spp., *Scirpophaga* spp., *Sesamia* spp., *Sparganothis* spp., *Spodopteralittoralis, Synanthedon* spp., *Thaumetopoea* spp., *Tortrix* spp., *Trichoplusia ni* and *Yponomeuta* spp.;

from the order Coleoptera, for example *Agriotes* spp., *Anthonomus* spp., *Atomaria linearis, Chaetocnema tibialis, Cosmopolites* spp., *Curculio* spp., *Dermestes* spp., *Diabrotica* spp.,

*Epilachna* spp., *Eremnus* spp., *Leptinotarsa decemlineata, Lissorhoptrus* spp., *Melolontha* spp., *Oryzaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

from the order Orthoptera, for example *Blatta* spp., *Blattella* spp., *Gryllotalpa* spp., *Leucophaea maderae, Locusta* spp., *Periplaneta* spp. and *Schistocerca* spp.;

from the order Isoptera, for example *Reticulitermes* spp.;

from the order Psocoptera, for example *Liposcelis* spp.;

from the order Anoplura, for example *Haematopinus* spp., *Linognathus* spp., *Pediculus* spp., *Pemphigus* spp. and *Phylloxera* spp.;

from the order Mallophaga, for example *Damalinea* spp. and *Trichodectes* spp.;

from the order Thysanoptera, for example *Frankliniella* spp., *Hercinothrips* spp., *Taeniothrips* spp., *Thrips palmi*, *Thrips tabaci* and *Scirtothrips aurantii*;

from the order Heteroptera, for example *Cimex* spp., *Distantiella theobroma*, *Dysdercus* spp., *Euchistus* spp. *Eurygaster* spp. *Leptocorisa* spp., *Nezara* spp., *Piesma* spp., *Rhodnius* spp., *Sahlbergella singularis*, *Scotinophara* spp. and *Triatoma* spp.;

from the order Homoptera, for example *Aleurothrixus floccosus*, *Aleyrodes brassicae*, *Aonidiella aurantii*, *Aphididae*, *Aphiscraccivora*, *A. fabae*, *A. gosypii*; *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma lanigerum*, *Erythroneura* spp., *Gascardia* spp., *Laodelphax* spp., *Lecanium corni*, *Lepidosaphes* spp., *Macrosiphus* spp., *Myzus* spp., especially *M.persicae*; *Nephotettix* spp., especially *N. cincticeps*; *Nilaparvata* spp., especially *N. lugens*; *Paratoria* spp., *Pemphigus* spp., *Planococcus* spp., *Pseudaulacaspis* spp., *Pseudococcus* spp., especially *P. Fragilis*, *P. citriculus* and *P. comstocki*; *Psylla* spp., especially *P. pyri*; *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*;

from the order Hymenoptera, for example *Acromyrmex*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.;

from the order Diptera, for example *Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp.;

from the order Siphonaptera, for example *Ceratophyllus* spp. and *Xenopsylla cheopis*;

from the order Thysanura, for example *Lepisma saccharina* and from the order Acarina, for example *Acarus siro*, *Aceria sheldoni*; *Aculus* spp., especially *A. schlechtendali*; *Amblyomma* spp., *Argas* spp., *Boophilus* spp., *Brevipalpus* spp., especially *B. californicus* and *B. phoenicis*; *Bryobia praetiosa*, *Calipitrimerus* spp., *Chorioptes* spp., *Dermanyssus gallinae*, *Eotetranychus* spp., especially *E.carpini* and *E. orientalis*; *Eriophyes* spp., especially *E. vitis*; *Hyalomma* spp., *Ixodes* spp., *Olygonychus pratensis*, *Ornithodoros* spp., *Panonychus* spp., especially *P. ulmi* and *P. citri*; *Phyllocoptruta* spp., especially *P. oleivora*; *Polyphagotarsonemus* spp., especially *P. latus*; *Psoroptes* spp., *Rhipicephalus* spp., *Rhizoglyphus* spp., *Sarcoptes* spp., *Tarsonemus* spp. and *Tetranychus* spp., in particular *T. urticae*, *T. cinnabarinus* and *T. Kanzawai*;

representatives of the class Nematoda;

(1) nematodes selected from the group consisting of root knot nematodes, cyst-forming nematodes, stem eelworms and foliar nematodes;

(2) nematodes selected from the group consisting of *Anguina* spp.; *Aphelenchoides* spp.; *Ditylenchus* spp.; *Globodera* spp., for example *Globodera rostochiensis*; *Heterodera* spp., for example *Heterodera avenae*, *Heterodera glycines*, *Heterodera schachtii* or *Heterodera trifolii*; *Longidorus* spp.; *Meloidogyne* spp., for example *Meloidogyne incognita* or *Meloidogyne javanica*; *Pratylenchus*, for example *Pratylenchus neglectans* or *Pratylenchus penetrans*; *Radopholus* spp., for example *Radopholus similis*; *Trichodorus* spp.; *Tylenchulus*, for example *Tylenchulus semipenetrans*; and *Xiphinema* spp.; or (3) nematodes selected from the group consisting of *Heterodera* spp., for example *Heterodera glycines*; and *Meloidogyne* spp., for example *Meloidogyne incognita*.

The method according to the invention (A) allows pests of the abovementioned type to be controlled, i.e. contained or destroyed, which occur, in particular, on transgenic plants, mainly useful plants and ornamentals in agriculture, in horticulture and in forests, or on parts, such as fruits, flowers, foliage, stalks, tubers or roots, of such plants, the protection against these pests in some cases even extending to plant parts which form at a later point in time.

The method according to the invention (A) can be employed advantageously for controlling pests in rice, cereals such as maize or sorghum; in fruit, for example stone fruit, pome fruit and soft fruit such as apples, pears, plums, peaches, almonds, cherries or berries, for example strawberries, raspberries and blackberries; in legumes such as beans, lentils, peas or soya beans; in oil crops such as oilseed rape, mustard, poppies, olives, sunflowers, coconuts, castor-oil plants, cacao or peanuts; in the marrow family such as pumpkins, cucumbers or melons; in fibre plants such as cotton, flax, hemp or jute; in citrus fruit such as oranges, lemons, grapefruit or tangerines; in vegetables such as spinach, lettuce, asparagus, cabbage species, carrots, onions, tomatoes, potatoes, beet or capsicum; in the laurel family such as avocado, Cinnamonium or camphor; or in tobacco, nuts, coffee, egg plants, sugar cane, tea, pepper, grapevines, hops, the banana family, latex plants or ornamentals, mainly in maize, rice, cereals, soya beans, tomatoes, cotton, potatoes, sugar beet, rice and mustard; in particular in cotton, rice, soya beans, potatoes and maize.

It has emerged that the method according to the invention (A) is valuable preventatively and/or curatively in the field of pest control even at low use concentrations of the pesticidal composition and that a very favourable biocidal spectrum is achieved thereby. Combined with a favourable compatibility of the composition employed with warm-blooded species, fish and plants, the method according to the invention can be employed against all or individual developmental stages of normally-sensitive, but also of normally-resistant, animal pests such as insects and representatives of the order Acarina, depending on the species of the transgenic crop plant to be protected from attack by pests. The insecticidal and/or acaricidal effect of the method according to the invention may become apparent directly, i.e. in a destruction of the pests which occurs immediately or only after some time has elapsed, for example, during ecdysis, or indirectly, for example as a reduced oviposition and/or hatching rate, the good action corresponding to a destruction rate (mortality) of at least 40 to 50%.

Depending on the intended aims and the prevailing circumstances, the pesticides within the scope of invention (A), which are known per se, are emulsifiable concentrates, suspension concentrates, directly sprayable or dilutable solutions, spreadable pastes, dilute emulsions, wettable powders, soluble powders, dispersible powders, wettable powders, dusts, granules or encapsulations in polymeric substances which comprise a macrolide compound.

The active ingredients are employed in these compositions together with at least one of the auxiliaries conventionally used in art of formulation, such as extenders, for example solvents or solid carriers, or such as surface-active compounds (surfactants).

Formulation auxiliaries which are used are, for example, solid carriers, solvents, stabilizers, "slow release" auxiliaries, colourants and, if appropriate, surface-active substances (surfactants). Suitable carriers and auxiliaries are all those substances which are conventionally used for crop protection products. Suitable auxiliaries such as solvents, solid carriers, surface-active compounds, non-ionic surfactants, cationic surfactants, anionic surfactants and other auxiliaries in the compositions employed according to the invention are, for example, those which have been described in EP-A-736 252.

These compositions for controlling pests can be formulated, for example, as wettable powders, dusts, granules, solutions, emulsifiable concentrates, emulsions, suspension concentrates or aerosols. For example, the compositions are of the type described in EP-A-736 252.

The action of the compositions within the scope of invention (A) which comprise a macrolide compound can be extended substantially and adapted to prevailing circumstances by adding other insecticidally, acaricidally and/or fungicidally active ingredients. Suitable examples of added active ingredients are representatives of the following classes of active ingredients: organophosphorous compounds, nitrophenols and derivatives, formamidines, ureas, carbamates, pyrethroids, chlorinated hydrocarbons; especially preferred components in mixtures are, for example, thiamethoxam, pymetrozine, fenoxycarb, imidacloprid, Ti-435, fipronil, pyriproxyfen, emamectin, diazinon or diafenthiuron.

As a rule, the compositions within the scope of invention (A) comprise 0.1 to 99%, in particular 0.1 to 95%, of a macrolide compound and 1 to 99.9%, in particular 5 to 99.9%, of—at least—one solid or liquid auxiliary, it being possible, as a rule, for 0 to 25%, in particular 0.1 to 20%, of the compositions to be surfactants (% in each case meaning percent by weight). While concentrated compositions are more preferred as commercial products, the end user will, as a rule, use dilute compositions which have considerably lower concentrations of active ingredient.

The compositions according to the invention (A) may also comprise other solid or liquid auxiliaries, such as stabilisers, for example epoxidized or unepoxidized vegetable oils (for example epoxidized coconut oil, rapeseed oil or soya bean oil), antifoams, for example silicone oil, preservatives, viscosity regulators, binders and/or tackifiers, and also fertilizers or other active ingredients for achieving specific effects, for example, bactericides, fungicides, nematicides, molluscicides or herbicides.

The compositions according to the invention (A) are produced in a known manner, for example prior to mixing with the auxiliary/auxiliaries by grinding, screening and/or compressing the active ingredient, for example to give a particular particle size, and by intimately mixing and/or grinding the active ingredient with the auxiliary/auxiliaries.

The method according to the invention for controlling pests of the abovementioned type is carried out in a manner known per se to those skilled in the art, depending on the intended aims and prevailing circumstances, that is to say by spraying, wetting, atomizing, dusting, brushing on, seed dressing, scattering or pouring of the composition. Typical use concentrations are between 0.1 and 1000 ppm, preferably between 0.1 and 500 ppm of active ingredient. The application rate may vary within wide ranges and depends on the soil constitution, the type of application (foliar application; seed dressing; application in the seed furrow), the transgenic crop plant, the pest to be controlled, the climatic circumstances prevailing in each case, and other factors determined by the type of application, timing of application and target crop. The application rates per hectare are generally 1 to 2000 g of macrolide compound per hectare, in particular 10 to 1000 g/ha, preferably 10 to 500 g/ha, especially preferably 10 to 200 g/ha.

A preferred type of application in the field of crop protection within the scope of invention (A) is application to the foliage of the plants (foliar application), it being possible to adapt frequency and rate of application to the risk of infestation with the pest in question. However, the active ingredient may also enter into the plants via the root system (systemic action), by drenching the site of the plants with a liquid composition or by incorporating the active ingredient in solid form into the site of the plants, for example into the soil, for example in the form of granules (soil application). In the case of paddy rice crops, such granules may be metered into the flooded paddy field.

The compositions according to invention (A) are also suitable for protecting propagation material of transgenic plants, for example seed, such as fruits, tubers or kernels, or plant cuttings, from animal pests, in particular insects and representatives of the order Acarina. The propagation material can be treated with the composition prior to application, for example, seed being dressed prior to sowing. The active ingredient may also be applied to seed kernels (coating), either by soaking the kernels in a liquid composition or by coating them with a solid composition. The composition may also be applied to the site of application when applying the propagation material, for example into the seed furrow during sowing. These treatment methods for plant propagation material and the plant propagation material treated thus are a further subject of the invention.

Examples of formulations of macrolide compounds which can be used in the method according to the invention (A), for instance solutions, granules, dusts, sprayable powders, emulsion concentrates, coated granules and suspension concentrates, are of the type as has been described in, for example, EP-A-580 553, Examples F1 to F10.

Table B

The following abreviations are used in the table:
Active Principle of transgenic plant: AP
*Photorhabdus luminescens:* PL
*Xenorhabdus nematophilus:* XN
Proteinase Inhibitors: PInh.
Plant lectins Plec
Agglutinins: Aggl.
3-Hydroxysteroid oxidase: HO
Cholesteroloxidase: CO
Chitinase: CH
Glucanase: GL
Stilbensynthase SS

TABLE B

|  | AP | Control of |
|---|---|---|
| B.1 | CryIA(a) | Adoxophyes spp. |
| B.2 | CryIA(a) | Agrotis spp. |
| B.3 | CryIA(a) | Alabama argillaceae |
| B.4 | CryIA(a) | Anticarsia gemmatalis |
| B.5 | CryIA(a) | Chilo spp. |

TABLE B-continued

| | AP | Control of |
|---|---|---|
| B.6 | CryIA(a) | *Clysia ambiguella* |
| B.7 | CryIA(a) | *Crocidolomia binotalis* |
| B.8 | CryIA(a) | Cydia spp. |
| B.9 | CryIA(a) | *Diparopsis castanea* |
| B.10 | CryIA(a) | Earias spp. |
| B.11 | CryIA(a) | Ephestia spp. |
| B.12 | CryIA(a) | Heliothis spp. |
| B.13 | CryIA(a) | *Hellula undalis* |
| B.14 | CryIA(a) | *Keiferia lycopersicella* |
| B.15 | CryIA(a) | *Leucoptera scitella* |
| B.16 | CryIA(a) | Lithocollethis spp. |
| B.17 | CryIA(a) | *Lobesia botrana* |
| B.18 | CryIA(a) | *Ostrinia nubilalis* |
| B.19 | CryIA(a) | Pandemis spp. |
| B.20 | CryIA(a) | *Pectinophora gossyp.* |
| B.21 | CryIA(a) | *Phyllocnistis citrella* |
| B.22 | CryIA(a) | Pieris spp. |
| B.23 | CryIA(a) | *Plutella xylostella* |
| B.24 | CryIA(a) | Scirpophaga spp. |
| B.25 | CryIA(a) | Sesamia spp. |
| B.26 | CryIA(a) | Sparganothis spp. |
| B.27 | CryIA(a) | Spodoptera spp. |
| B.28 | CryIA(a) | Tortrix spp. |
| B.29 | CryIA(a) | Trichoplusia ni |
| B.30 | CryIA(a) | Agriotes spp. |
| B.31 | CryIA(a) | *Anthonomus grandis* |
| B.32 | CryIA(a) | Curculio spp. |
| B.33 | CryIA(a) | *Diabrotica balteata* |
| B.34 | CryIA(a) | Leptinotarsa spp. |
| B.35 | CryIA(a) | Lissorhoptrus spp. |
| B.36 | CryIA(a) | Otiorhynchus spp. |
| B.37 | CryIA(a) | Aleurothrixus spp. |
| B.38 | CryIA(a) | Aleyrodes spp. |
| B.39 | CryIA(a) | Aonidiella spp. |
| B.40 | CryIA(a) | Aphididae spp. |
| B.41 | CryIA(a) | Aphis spp. |
| B.42 | CryIA(a) | *Bemisia tabaci* |
| B.43 | CryIA(a) | Empoasca spp. |
| B.44 | CryIA(a) | Mycus spp. |
| B.45 | CryIA(a) | Nephotettix spp. |
| B.46 | CryIA(a) | Nilaparvata spp. |
| B.47 | CryIA(a) | Pseudococcus spp. |
| B.48 | CryIA(a) | Psylla spp. |
| B.49 | CryIA(a) | Quadraspidiotus spp. |
| B.50 | CryIA(a) | Schizaphis spp. |
| B.51 | CryIA(a) | Trialeurodes spp. |
| B.52 | CryIA(a) | Lyriomyza spp. |
| B.53 | CryIA(a) | Oscinella spp. |
| B.54 | CryIA(a) | Phorbia spp. |
| B.55 | CryIA(a) | Frankliniella spp. |
| B.56 | CryIA(a) | Thrips spp. |
| B.57 | CryIA(a) | *Scirtothrips aurantii* |
| B.58 | CryIA(a) | Aceria spp. |
| B.59 | CryIA(a) | Aculus spp. |
| B.60 | CryIA(a) | Brevipalpus spp. |
| B.61 | CryIA(a) | Panonychus spp. |
| B.62 | CryIA(a) | Phyllocoptruta spp. |
| B.63 | CryIA(a) | Tetranychus spp. |
| B.64 | CryIA(a) | Heterodera spp. |
| B.65 | CryIA(a) | Meloidogyne spp. |
| B.66 | CryIA(b) | Adoxophyes spp. |
| B.67 | CryIA(b) | Agrotis spp. |
| B.68 | CryIA(b) | *Alabama argillaceae* |
| B.69 | CryIA(b) | *Anticarsia gemmatalis* |
| B.70 | CryIA(b) | Chilo spp. |
| B.71 | CryIA(b) | *Clysia ambiguella* |
| B.72 | CryIA(b) | *Crocidolomia binotalis* |
| B.73 | CryIA(b) | Cydia spp. |
| B.74 | CryIA(b) | *Diparopsis castanea* |
| B.75 | CryIA(b) | Earias spp. |
| B.76 | CryIA(b) | Ephestia spp. |
| B.77 | CryIA(b) | Heliothis spp. |
| B.78 | CryIA(b) | *Hellula undalis* |
| B.79 | CryIA(b) | *Keiferia lycopersicella* |
| B.80 | CryIA(b) | *Leucoptera scitella* |
| B.81 | CryIA(b) | Lithocollethis spp. |
| B.82 | CryIA(b) | *Lobesia botrana* |
| B.83 | CryIA(b) | *Ostrinia nubilalis* |
| B.84 | CryIA(b) | Pandemis spp. |
| B.85 | CryIA(b) | *Pectinophora gossyp.* |
| B.86 | CryIA(b) | *Phyllocnistis citrella* |
| B.87 | CryIA(b) | Pieris spp. |
| B.88 | CryIA(b) | *Plutella xylostella* |
| B.89 | CryIA(b) | Scirpophaga spp. |
| B.90 | CryIA(b) | Sesamia spp. |
| B.91 | CryIA(b) | Sparganothis spp. |
| B.92 | CryIA(b) | Spodoptera spp. |
| B.93 | CryIA(b) | Tortrix spp. |
| B.94 | CryIA(b) | Trichoplusia ni |
| B.95 | CryIA(b) | Agriotes spp. |
| B.96 | CryIA(b) | *Anthonomus grandis* |
| B.97 | CryIA(b) | Curculio spp. |
| B.98 | CryIA(b) | *Diabrotica balteata* |
| B.99 | CryIA(b) | Leptinotarsa spp. |
| B.100 | CryIA(b) | Lissorhoptrus spp. |
| B.101 | CryIA(b) | Otiorhynchus spp. |
| B.102 | CryIA(b) | Aleurothrixus spp. |
| B.103 | CryIA(b) | Aleyrodes spp. |
| B.104 | CryIA(b) | Aonidiella spp. |
| B.105 | CryIA(b) | Aphididae spp. |
| B.106 | CryIA(b) | Aphis spp. |
| B.107 | CryIA(b) | *Bemisia tabaci* |
| B.108 | CryIA(b) | Empoasca spp. |
| B.109 | CryIA(b) | Mycus spp. |
| B.110 | CryIA(b) | Nephotettix spp. |
| B.111 | CryIA(b) | Nilaparvata spp. |
| B.112 | CryIA(b) | Pseudococcus spp. |
| B.113 | CryIA(b) | Psylla spp. |
| B.114 | CryIA(b) | Quadraspidiotus spp. |
| B.115 | CryIA(b) | Schizaphis spp. |
| B.116 | CryIA(b) | Trialeurodes spp. |
| B.117 | CryIA(b) | Lyriomyza spp. |
| B.118 | CryIA(b) | Oscinella spp. |
| B.119 | CryIA(b) | Phorbia spp. |
| B.120 | CryIA(b) | Frankliniella spp. |
| B.121 | CryIA(b) | Thrips spp. |
| B.122 | CryIA(b) | *Scirtothrips aurantii* |
| B.123 | CryIA(b) | Aceria spp. |
| B.124 | CryIA(b) | Aculus spp. |
| B.125 | CryIA(b) | Brevipalpus spp. |
| B.126 | CryIA(b) | Panonychus spp. |
| B.127 | CryIA(b) | Phyllocoptruta spp. |
| B.128 | CryIA(b) | Tetranychus spp. |
| B.129 | CryIA(b) | Heterodera spp. |
| B.130 | CryIA(b) | Meloidogyne spp. |
| B.131 | CryIA(c) | Adoxophyes spp. |
| B.132 | CryIA(c) | Agrotis spp. |
| B.133 | CryIA(c) | *Alabama argillaceae* |
| B.134 | CryIA(c) | *Anticarsia gemmatalis* |
| B.135 | CryIA(c) | Chilo spp. |
| B.136 | CryIA(c) | *Clysia ambiguella* |
| B.137 | CryIA(c) | *Crocidolomia binotalis* |
| B.138 | CryIA(c) | Cydia spp. |
| B.139 | CryIA(c) | *Diparopsis castanea* |
| B.140 | CryIA(c) | Earias spp. |
| B.141 | CryIA(c) | Ephestia spp. |

TABLE B-continued

| AP | | Control of |
|---|---|---|
| B.142 | CryIA(c) | Heliothis spp. |
| B.143 | CryIA(c) | Hellula undalis |
| B.144 | CryIA(c) | *Keiferia lycopersicella* |
| B.145 | CryIA(c) | *Leucoptera scitella* |
| B.146 | CryIA(c) | Lithocollethis spp. |
| B.147 | CryIA(c) | *Lobesia botrana* |
| B.148 | CryIA(c) | *Ostrinia nubilalis* |
| B.149 | CryIA(c) | Pandemis spp. |
| B.150 | CryIA(c) | *Pectinophora gossypiella.* |
| B.151 | CryIA(c) | *Phyllocnistis citrella* |
| B.152 | CryIA(c) | Pieris spp. |
| B.153 | CryIA(c) | *Plutella xylostella* |
| B.154 | CryIA(c) | Scirpophaga spp. |
| B.155 | CryIA(c) | Sesamia spp. |
| B.156 | CryIA(c) | Sparganothis spp. |
| B.157 | CryIA(c) | Spodoptera spp. |
| B.158 | CryIA(c) | Tortrix spp. |
| B.159 | CryIA(c) | Trichoplusia ni |
| B.160 | CryIA(c) | Agriotes spp. |
| B.161 | CryIA(c) | Anthonomus grandis |
| B.162 | CryIA(c) | Curculio spp. |
| B.163 | CryIA(c) | *Diabrotica balteata* |
| B.164 | CryIA(c) | Leptinotarsa spp. |
| B.165 | CryIA(c) | Lissorhoptrus spp. |
| B.166 | CryIA(c) | Otiorhynchus spp. |
| B.167 | CryIA(c) | Aleurothrixus spp. |
| B.168 | CryIA(c) | Aleyrodes spp. |
| B.169 | CryIA(c) | Aonidiella spp. |
| B.170 | CryIA(c) | Aphididae spp. |
| B.171 | CryIA(c) | Aphis spp. |
| B.172 | CryIA(c) | *Bemisia tabaci* |
| B.173 | CryIA(c) | Empoasca spp. |
| B.174 | CryIA(c) | Mycus spp. |
| B.175 | CryIA(c) | Nephotettix spp. |
| B.176 | CryIA(c) | Nilaparvata spp. |
| B.177 | CryIA(c) | Pseudococcus spp. |
| B.178 | CryIA(c) | Psylla spp. |
| B.179 | CryIA(c) | Quadraspidiotus spp. |
| B.180 | CryIA(c) | Schizaphis spp. |
| B.181 | CryIA(c) | Trialeurodes spp. |
| B.182 | CryIA(c) | Lyriomyza spp. |
| B.183 | CryIA(c) | Oscinella spp. |
| B.184 | CryIA(c) | Phorbia spp. |
| B.185 | CryIA(c) | Frankliniella spp. |
| B.186 | CryIA(c) | Thrips spp. |
| B.187 | CryIA(c) | *Scirtothrips aurantii* |
| B.188 | CryIA(c) | Aceria spp. |
| B.189 | CryIA(c) | Aculus spp. |
| B.190 | CryIA(c) | Brevipalpus spp. |
| B.191 | CryIA(c) | Panonychus spp. |
| B.192 | CryIA(c) | Phyllocoptruta spp. |
| B.193 | CryIA(c) | Tetranychus spp. |
| B.194 | CryIA(c) | Heterodera spp. |
| B.195 | CryIA(c) | Meloidogyne spp. |
| B.196 | CryIIA | Adoxophyes spp. |
| B.197 | CryIIA | Agrotis spp. |
| B.198 | CryIIA | *Alabama argillaceae* |
| B.199 | CryIIA | *Anticarsia gemmatalis* |
| B.200 | CryIIA | Chilo spp. |
| B.201 | CryIIA | *Clysia ambiguella* |
| B.202 | CryIIA | *Crocidolomia binotalis* |
| B.203 | CryIIA | Cydia spp. |
| B.204 | CryIIA | *Diparopsis castanea* |
| B.205 | CryIIA | Earias spp. |
| B.206 | CryIIA | Ephestia spp. |
| B.207 | CryIIA | Heliothis spp. |
| B.208 | CryIIA | Hellula undalis |
| B.209 | CryIIA | *Keiferia lycopersicella* |
| B.210 | CryIIA | *Leucoptera scitella* |
| B.211 | CryIIA | Lithocollethis spp. |
| B.212 | CryIIA | *Lobesia botrana* |
| B.213 | CryIIA | *Ostrinia nubilalis* |
| B.214 | CryIIA | Pandemis spp. |
| B.215 | CryIIA | *Pectinophora gossyp.* |
| B.216 | CryIIA | *Phyllocnistis citrella* |
| B.217 | CryIIA | Pieris spp. |
| B.218 | CryIIA | *Plutella xylostella* |
| B.219 | CryIIA | Scirpophaga spp. |
| B.220 | CryIIA | Sesamia spp. |
| B.221 | CryIIA | Sparganothis spp. |
| B.222 | CryIIA | Spodoptera spp. |
| B.223 | CryIIA | Tortrix spp. |
| B.224 | CryIIA | Trichoplusia ni |
| B.225 | CryIIA | Agriotes spp. |
| B.226 | CryIIA | Anthonomus grandis |
| B.227 | CryIIA | Curculio spp. |
| B.228 | CryIIA | *Diabrotica balteata* |
| B.229 | CryIIA | Leptinotarsa spp. |
| B.230 | CryIIA | Lissorhoptrus spp. |
| B.231 | CryIIA | Otiorhynchus spp. |
| B.232 | CryIIA | Aleurothrixus spp. |
| B.233 | CryIIA | Aleyrodes spp. |
| B.234 | CryIIA | Aonidiella spp. |
| B.235 | CryIIA | Aphididae spp. |
| B.236 | CryIIA | Aphis spp. |
| B.237 | CryIIA | *Bemisia tabaci* |
| B.238 | CryIIA | Empoasca spp. |
| B.239 | CryIIA | Mycus spp. |
| B.240 | CryIIA | Nephotettix spp. |
| B.241 | CryIIA | Nilaparvata spp. |
| B.242 | CryIIA | Pseudococcus spp. |
| B.243 | CryIIA | Psylla spp. |
| B.244 | CryIIA | Quadraspidiotus spp. |
| B.245 | CryIIA | Schizaphis spp. |
| B.246 | CryIIA | Trialeurodes spp. |
| B.247 | CryIIA | Lyriomyza spp. |
| B.248 | CryIIA | Oscinella spp. |
| B.249 | CryIIA | Phorbia spp. |
| B.250 | CryIIA | Frankliniella spp. |
| B.251 | CryIIA | Thrips spp. |
| B.252 | CryIIA | *Scirtothrips aurantii* |
| B.253 | CryIIA | Aceria spp. |
| B.254 | CryIIA | Aculus spp. |
| B.255 | CryIIA | Brevipalpus spp. |
| B.256 | CryIIA | Panonychus spp. |
| B.257 | CryIIA | Phyllocoptruta spp. |
| B.258 | CryIIA | Tetranychus spp. |
| B.259 | CryIIA | Heterodera spp. |
| B.260 | CryIIA | Meloidogyne spp. |
| B.261 | CryIIIA | Adoxophyes spp. |
| B.262 | CryIIIA | Agrotis spp. |
| B.263 | CryIIIA | *Alabama argillaceae* |
| B.264 | CryIIIA | *Anticarsia gemmatalis* |
| B.265 | CryIIIA | Chilo spp. |
| B.266 | CryIIIA | *Clysia ambiguella* |
| B.267 | CryIIIA | *Crocidolomia binotalis* |
| B.268 | CryIIIA | Cydia spp. |
| B.269 | CryIIIA | *Diparopsis castanea* |
| B.270 | CryIIIA | Earias spp. |
| B.271 | CryIIIA | Ephestia spp. |
| B.272 | CryIIIA | Heliothis spp. |
| B.273 | CryIIIA | Hellula undalis |
| B.274 | CryIIIA | *Keiferia lycopersicella* |
| B.275 | CryIIIA | *Leucoptera scitella* |
| B.276 | CryIIIA | Lithocollethis spp. |
| B.277 | CryIIIA | *Lobesia botrana* |
| B.278 | CryIIIA | *Ostrinia nubilalis* |

TABLE B-continued

| | AP | Control of |
|---|---|---|
| B.279 | CryIIIA | Pandemis spp. |
| B.280 | CryIIIA | Pectinophora gossyp. |
| B.281 | CryIIIA | Phyllocnistis citrella |
| B.282 | CryIIIA | Pieris spp. |
| B.283 | CryIIIA | Plutella xylostella |
| B.284 | CryIIIA | Scirpophaga spp. |
| B.285 | CryIIIA | Sesamia spp. |
| B.286 | CryIIIA | Sparganothis spp. |
| B.287 | CryIIIA | Spodoptera spp. |
| B.288 | CryIIIA | Tortrix spp. |
| B.289 | CryIIIA | Trichoplusia ni |
| B.290 | CryIIIA | Agriotes spp. |
| B.291 | CryIIIA | Anthonomus grandis |
| B.292 | CryIIIA | Curculio spp. |
| B.293 | CryIIIA | Diabrotica balteata |
| B.294 | CryIIIA | Leptinotarsa spp. |
| B.295 | CryIIIA | Lissorhoptrus spp. |
| B.296 | CryIIIA | Otiorhynchus spp. |
| B.297 | CryIIIA | Aleurothrixus spp. |
| B.298 | CryIIIA | Aleyrodes spp. |
| B.299 | CryIIIA | Aonidiella spp. |
| B.300 | CryIIIA | Aphididae spp. |
| B.301 | CryIIIA | Aphis spp. |
| B.302 | CryIIIA | Bemisia tabaci |
| B.303 | CryIIIA | Empoasca spp. |
| B.304 | CryIIIA | Mycus spp. |
| B.305 | CryIIIA | Nephotettix spp. |
| B.306 | CryIIIA | Nilaparvata spp. |
| B.307 | CryIIIA | Pseudococcus spp. |
| B.308 | CryIIIA | Psylla spp. |
| B.309 | CryIIIA | Quadraspidiotus spp. |
| B.310 | CryIIIA | Schizaphis spp. |
| B.311 | CryIIIA | Trialeurodes spp. |
| B.312 | CryIIIA | Lyriomyza spp. |
| B.313 | CryIIIA | Oscinella spp. |
| B.314 | CryIIIA | Phorbia spp. |
| B.315 | CryIIIA | Frankliniella spp. |
| B.316 | CryIIIA | Thrips spp. |
| B.317 | CryIIIA | Scirtothrips aurantii |
| B.318 | CryIIIA | Aceria spp. |
| B.319 | CryIIIA | Aculus spp. |
| B.320 | CryIIIA | Brevipalpus spp. |
| B.321 | CryIIIA | Panonychus spp. |
| B.322 | CryIIIA | Phyllocoptruta spp. |
| B.323 | CryIIIA | Tetranychus spp. |
| B.324 | CryIIIA | Heterodera spp. |
| B.325 | CryIIIA | Meloidogyne spp. |
| B.326 | CryIIIB2 | Adoxophyes spp. |
| B.327 | CryIIIB2 | Agrotis spp. |
| B.328 | CryIIIB2 | Alabama argillaceae |
| B.329 | CryIIIB2 | Anticarsia gemmatalis |
| B.330 | CryIIIB2 | Chilo spp. |
| B.331 | CryIIIB2 | Clysia ambiguella |
| B.332 | CryIIIB2 | Crocidolomia binotalis |
| B.333 | CryIIIB2 | Cydia spp. |
| B.334 | CryIIIB2 | Diparopsis castanea |
| B.335 | CryIIIB2 | Earias spp. |
| B.336 | CryIIIB2 | Ephestia spp. |
| B.337 | CryIIIB2 | Heliothis spp. |
| B.338 | CryIIIB2 | Hellula undalis |
| B.339 | CryIIIB2 | Keiferia lycopersicella |
| B.340 | CryIIIB2 | Leucoptera scitella |
| B.341 | CryIIIB2 | Lithocollethis spp. |
| B.342 | CryIIIB2 | Lobesia botrana |
| B.343 | CryIIIB2 | Ostrinia nubilalis |
| B.344 | CryIIIB2 | Pandemis spp. |
| B.345 | CryIIIB2 | Pectinophora gossyp. |
| B.346 | CryIIIB2 | Phyllocnistis citrella |
| B.347 | CryIIIB2 | Pieris spp. |
| B.348 | CryIIIB2 | Plutella xylostella |
| B.349 | CryIIIB2 | Scirpophaga spp. |
| B.350 | CryIIIB2 | Sesamia spp. |
| B.351 | CryIIIB2 | Sparganothis spp. |
| B.352 | CryIIIB2 | Spodoptera spp. |
| B.353 | CryIIIB2 | Tortrix spp. |
| B.354 | CryIIIB2 | Trichoplusia ni |
| B.355 | CryIIIB2 | Agriotes spp. |
| B.356 | CryIIIB2 | Anthonomus grandis |
| B.357 | CryIIIB2 | Curculio spp. |
| B.358 | CryIIIB2 | Diabrotica balteata |
| B.359 | CryIIIB2 | Leptinotarsa spp. |
| B.360 | CryIIIB2 | Lissorhoptrus spp. |
| B.361 | CryIIIB2 | Otiorhynchus spp. |
| B.362 | CryIIIB2 | Aleurothrixus spp. |
| B.363 | CryIIIB2 | Aleyrodes spp. |
| B.364 | CryIIIB2 | Aonidiella spp. |
| B.365 | CryIIIB2 | Aphididae spp. |
| B.366 | CryIIIB2 | Aphis spp. |
| B.367 | CryIIIB2 | Bemisia tabaci |
| B.368 | CryIIIB2 | Empoasca spp. |
| B.369 | CryIIIB2 | Mycus spp. |
| B.370 | CryIIIB2 | Nephotettix spp. |
| B.371 | CryIIIB2 | Nilaparvata spp. |
| B.372 | CryIIIB2 | Pseudococcus spp. |
| B.373 | CryIIIB2 | Psylla spp. |
| B.374 | CryIIIB2 | Quadraspidiotus spp. |
| B.375 | CryIIIB2 | Schizaphis spp. |
| B.376 | CryIIIB2 | Trialeurodes spp. |
| B.377 | CryIIIB2 | Lyriomyza spp. |
| B.378 | CryIIIB2 | Oscinella spp. |
| B.379 | CryIIIB2 | Phorbia spp. |
| B.380 | CryIIIB2 | Frankliniella spp. |
| B.381 | CryIIIB2 | Thrips spp. |
| B.382 | CryIIIB2 | Scirtothrips aurantii |
| B.383 | CryIIIB2 | Aceria spp. |
| B.384 | CryIIIB2 | Aculus spp. |
| B.385 | CryIIIB2 | Brevipalpus spp. |
| B.386 | CryIIIB2 | Panonychus spp. |
| B.387 | CryIIIB2 | Phyllocoptruta spp. |
| B.388 | CryIIIB2 | Tetranychus spp. |
| B.389 | CryIIIB2 | Heterodera spp. |
| B.390 | CryIIIB2 | Meloidogyne spp. |
| B.391 | CytA | Adoxophyes spp. |
| B.392 | CytA | Agrotis spp. |
| B.393 | | Alabama argillaceae |
| B.394 | CytA | Anticarsia gemmatalis |
| B.395 | CytA | Chilo spp. |
| B.396 | CytA | Clysia ambiguella |
| B.397 | CytA | Crocidolomia binotalis |
| B.398 | CytA | Cydia spp. |
| B.399 | CytA | Diparopsis castanea |
| B.400 | CytA | Earias spp. |
| B.401 | CytA | Ephestia spp. |
| B.402 | CytA | Heliothis spp. |
| B.403 | CytA | Hellula undalis |
| B.404 | CytA | Keiferia lycopersicella |
| B.405 | CytA | Leucoptera scitella |
| B.406 | CytA | Lithocollethis spp. |
| B.407 | CytA | Lobesia botrana |
| B.408 | CytA | Ostrinia nubilalis |
| B.409 | CytA | Pandemis spp. |
| B.410 | CytA | Pectinophora gossyp. |
| B.411 | CytA | Phyllocnistis citrella |
| B.412 | CytA | Pieris spp. |
| B.413 | CytA | Plutella xylostella |
| B.414 | CytA | Scirpophaga spp. |
| B.415 | CytA | Sesamia spp. |

TABLE B-continued

| | AP | Control of |
|---|---|---|
| B.416 | CytA | Sparganothis spp. |
| B.417 | CytA | Spodoptera spp. |
| B.418 | CytA | Tortrix spp. |
| B.419 | CytA | Trichoplusia ni |
| B.420 | CytA | Agriotes spp. |
| B.421 | CytA | Anthonomus grandis |
| B.422 | CytA | Curculio spp. |
| B.423 | CytA | Diabrotica balteata |
| B.424 | CytA | Leptinotarsa spp. |
| B.425 | CytA | Lissorhoptrus spp. |
| B.426 | CytA | Otiorhynchus spp. |
| B.427 | CytA | Aleurothrixus spp. |
| B.428 | CytA | Aleyrodes spp. |
| B.429 | CytA | Aonidiella spp. |
| B.430 | CytA | Aphididae spp. |
| B.431 | CytA | Aphis spp. |
| B.432 | CytA | Bemisia tabaci |
| B.433 | CytA | Empoasca spp. |
| B.434 | CytA | Mycus spp. |
| B.435 | CytA | Nephotettix spp. |
| B.436 | CytA | Nilaparvata spp. |
| B.437 | CytA | Pseudococcus spp. |
| B.438 | CytA | Psylla spp. |
| B.439 | CytA | Quadraspidiotus spp. |
| B.440 | CytA | Schizaphis spp. |
| B.441 | CytA | Trialeurodes spp. |
| B.442 | CytA | Lyriomyza spp. |
| B.443 | CytA | Oscinella spp. |
| B.444 | CytA | Phorbia spp. |
| B.445 | CytA | Frankliniella spp. |
| B.446 | CytA | Thrips spp. |
| B.447 | CytA | Scirtothrips aurantii |
| B.448 | CytA | Aceria spp. |
| B.449 | CytA | Aculus spp. |
| B.450 | CytA | Brevipalpus spp. |
| B.451 | CytA | Panonychus spp. |
| B.452 | CytA | Phyllocoptruta spp. |
| B.453 | CytA | Tetranychus spp. |
| B.454 | CytA | Heterodera spp. |
| B.455 | CytA | Meloidogyne spp. |
| B.456 | VIP3 | Adoxophyes spp. |
| B.457 | VIP3 | Agrotis spp. |
| B.458 | VIP3 | Alabama argillaceae |
| B.459 | VIP3 | Anticarsia gemmatalis |
| B.460 | VIP3 | Chilo spp. |
| B.461 | VIP3 | Clysia ambiguella |
| B.462 | VIP3 | Crocidolomia binotalis |
| B.463 | VIP3 | Cydia spp. |
| B.464 | VIP3 | Diparopsis castanea |
| B.465 | VIP3 | Earias spp. |
| B.466 | VIP3 | Ephestia spp. |
| B.467 | VIP3 | Heliothis spp. |
| B.468 | VIP3 | Hellula undalis |
| B.469 | VIP3 | Keiferia lycopersicella |
| B.470 | VIP3 | Leucoptera scitella |
| B.471 | VIP3 | Lithocollethis spp. |
| B.472 | VIP3 | Lobesia botrana |
| B.473 | VIP3 | Ostrinia nubilalis |
| B.474 | VIP3 | Pandemis spp. |
| B.475 | VIP3 | Pectinophora gossyp. |
| B.476 | VIP3 | Phyllocnistis citrella |
| B.477 | VIP3 | Pieris spp. |
| B.478 | VIP3 | Plutella xylostella |
| B.479 | VIP3 | Scirpophaga spp. |
| B.480 | VIP3 | Sesamia spp. |
| B.481 | VIP3 | Sparganothis spp. |
| B.482 | VIP3 | Spodoptera spp. |
| B.483 | VIP3 | Tortrix spp. |
| B.484 | VIP3 | Trichoplusia ni |
| B.485 | VIP3 | Agriotes spp. |
| B.486 | VIP3 | Anthonomus grandis |
| B.487 | VIP3 | Curculio spp. |
| B.488 | VIP3 | Diabrotica balteata |
| B.489 | VIP3 | Leptinotarsa spp. |
| B.490 | VIP3 | Lissorhoptrus spp. |
| B.491 | VIP3 | Otiorhynchus spp. |
| B.492 | VIP3 | Aleurothrixus spp. |
| B.493 | VIP3 | Aleyrodes spp. |
| B.494 | VIP3 | Aonidiella spp. |
| B.495 | VIP3 | Aphididae spp. |
| B.496 | VIP3 | Aphis spp. |
| B.497 | VIP3 | Bemisia tabaci |
| B.498 | VIP3 | Empoasca spp. |
| B.499 | VIP3 | Mycus spp. |
| B.500 | VIP3 | Nephotettix spp. |
| B.501 | VIP3 | Nilaparvata spp. |
| B.502 | VIP3 | Pseudococcus spp. |
| B.503 | VIP3 | Psylla spp. |
| B.504 | VIP3 | Quadraspidiotus spp. |
| B.505 | VIP3 | Schizaphis spp. |
| B.506 | VIP3 | Trialeurodes spp. |
| B.507 | VIP3 | Lyriomyza spp. |
| B.508 | VIP3 | Oscinella spp. |
| B.509 | VIP3 | Phorbia spp. |
| B.510 | VIP3 | Frankliniella spp. |
| B.511 | VIP3 | Thrips spp. |
| B.512 | VIP3 | Scirtothrips aurantii |
| B.513 | VIP3 | Aceria spp. |
| B.514 | VIP3 | Aculus spp. |
| B.515 | VIP3 | Brevipalpus spp. |
| B.516 | VIP3 | Panonychus spp. |
| B.517 | VIP3 | Phyllocoptruta spp. |
| B.518 | VIP3 | Tetranychus spp. |
| B.519 | VIP3 | Heterodera spp. |
| B.520 | VIP3 | Meloidogyne spp. |
| B.521 | GL | Adoxophyes spp. |
| B.522 | GL | Agrotis spp. |
| B.523 | GL | Alabama argillaceae |
| B.524 | GL | Anticarsia gemmatalis |
| B.525 | GL | Chilo spp. |
| B.526 | GL | Clysia ambiguella |
| B.527 | GL | Crocidolomia binotalis |
| B.528 | GL | Cydia spp. |
| B.529 | GL | Diparopsis castanea |
| B.530 | GL | Earias spp. |
| B.531 | GL | Ephestia spp. |
| B.532 | GL | Heliothis spp. |
| B.533 | GL | Hellula undalis |
| B.534 | GL | Keiferia lycopersicella |
| B.535 | GL | Leucoptera scitella |
| B.536 | GL | Lithocollethis spp. |
| B.537 | GL | Lobesia botrana |
| B.538 | GL | Ostrinia nubilalis |
| B.539 | GL | Pandemis spp. |
| B.540 | GL | Pectinophora gossyp. |
| B.541 | GL | Phyllocnistis citrella |
| B.542 | GL | Pieris spp. |
| B.543 | GL | Plutella xylostella |
| B.544 | GL | Scirpophaga spp. |
| B.545 | GL | Sesamia spp. |
| B.546 | GL | Sparganothis spp. |
| B.547 | GL | Spodoptera spp. |
| B.548 | GL | Tortrix spp. |
| B.549 | GL | Trichoplusia ni |
| B.550 | GL | Agriotes spp. |
| B.551 | GL | Anthonomus grandis |
| B.552 | GL | Curculio spp. |

TABLE B-continued

| | AP | Control of |
|---|---|---|
| B.553 | GL | *Diabrotica balteata* |
| B.554 | GL | Leptinotarsa spp. |
| B.555 | GL | Lissorhoptrus spp. |
| B.556 | GL | Otiorhynchus spp. |
| B.557 | GL | Aleurothrixus spp. |
| B.558 | GL | Aleyrodes spp. |
| B.559 | GL | Aonidiella spp. |
| B.560 | GL | Aphididae spp. |
| B.561 | GL | Aphis spp. |
| B.562 | GL | *Bemisia tabaci* |
| B.563 | GL | Empoasca spp. |
| B.564 | GL | Mycus spp. |
| B.565 | GL | Nephotettix spp. |
| B.566 | GL | Nilaparvata spp. |
| B.567 | GL | Pseudococcus spp. |
| B.568 | GL | Psylla spp. |
| B.569 | GL | Quadraspidiotus spp. |
| B.570 | GL | Schizaphis spp. |
| B.571 | GL | Trialeurodes spp. |
| B.572 | GL | Lyriomyza spp. |
| B.573 | GL | Oscinella spp. |
| B.574 | GL | Phorbia spp. |
| B.575 | GL | Frankliniella spp. |
| B.576 | GL | Thrips spp. |
| B.577 | GL | *Scirtothrips aurantii* |
| B.578 | GL | Aceria spp. |
| B.579 | GL | Aculus spp. |
| B.580 | GL | Brevipalpus spp. |
| B.581 | GL | Panonychus spp. |
| B.582 | GL | Phyllocoptruta spp. |
| B.583 | GL | Tetranychus spp. |
| B.584 | GL | Heterodera spp. |
| B.585 | GL | Meloidogyne spp. |
| B.586 | PL | Adoxophyes spp. |
| B.587 | PL | Agrotis spp. |
| B.588 | PL | *Alabama argillaceae* |
| B.589 | PL | *Anticarsia gemmatalis* |
| B.590 | PL | Chilo spp. |
| B.591 | PL | *Clysia ambiguella* |
| B.592 | PL | *Crocidolomia binotalis* |
| B.593 | PL | Cydia spp. |
| B.594 | PL | *Diparopsis castanea* |
| B.595 | PL | Earias spp. |
| B.596 | PL | Ephestia spp. |
| B.597 | PL | Heliothis spp. |
| B.598 | PL | *Hellula undalis* |
| B.599 | PL | *Keiferia lycopersicella* |
| B.600 | PL | *Leucoptera scitella* |
| B.601 | PL | Lithocollethis spp. |
| B.602 | PL | *Lobesia botrana* |
| B.603 | PL | *Ostrinia nubilalis* |
| B.604 | PL | Pandemis spp. |
| B.605 | PL | *Pectinophora gossyp.* |
| B.606 | PL | *Phyllocnistis citrella* |
| B.607 | PL | Pieris spp. |
| B.608 | PL | *Plutella xylostella* |
| B.609 | PL | Scirpophaga spp. |
| B.610 | PL | Sesamia spp. |
| B.611 | PL | Sparganothis spp. |
| B.612 | PL | Spodoptera spp. |
| B.613 | PL | Tortrix spp. |
| B.614 | PL | Trichoplusia ni |
| B.615 | PL | Agriotes spp. |
| B.616 | PL | *Anthonomus grandis* |
| B.617 | PL | Curculio spp. |
| B.618 | PL | *Diabrotica balteata* |
| B.619 | PL | Leptinotarsa spp. |
| B.620 | PL | Lissorhoptrus spp. |
| B.621 | PL | Otiorhynchus spp. |
| B.622 | PL | Aleurothrixus spp. |
| B.623 | PL | Aleyrodes spp. |
| B.624 | PL | Aonidiella spp. |
| B.625 | PL | Aphididae spp. |
| B.626 | PL | Aphis spp. |
| B.627 | PL | *Bemisia tabaci* |
| B.628 | PL | Empoasca spp. |
| B.629 | PL | Mycus spp. |
| B.630 | PL | Nephotettix spp. |
| B.631 | PL | Nilaparvata spp. |
| B.632 | PL | Pseudococcus spp. |
| B.633 | PL | Psylla spp. |
| B.634 | PL | Quadraspidiotus spp. |
| B.635 | PL | Schizaphis spp. |
| B.636 | PL | Trialeurodes spp. |
| B.637 | PL | Lyriomyza spp. |
| B.638 | PL | Oscinella spp. |
| B.639 | PL | Phorbia spp. |
| B.640 | PL | Frankliniella spp. |
| B.641 | PL | Thrips spp. |
| B.642 | PL | *Scirtothrips aurantii* |
| B.643 | PL | Aceria spp. |
| B.644 | PL | Aculus spp. |
| B.645 | PL | Brevipalpus spp. |
| B.646 | PL | Panonychus spp. |
| B.647 | PL | Phyllocoptruta spp. |
| B.648 | PL | Tetranychus spp. |
| B.649 | PL | Heterodera spp. |
| B.650 | PL | Meloidogyne spp. |
| B.651 | XN | Adoxophyes spp. |
| B.652 | XN | Agrotis spp. |
| B.653 | XN | *Alabama argillaceae* |
| B.654 | XN | *Anticarsia gemmatalis* |
| B.655 | XN | Chilo spp. |
| B.656 | XN | *Clysia ambiguella* |
| B.657 | XN | *Crocidolomia binotalis* |
| B.658 | XN | Cydia spp. |
| B.659 | XN | *Diparopsis castanea* |
| B.660 | XN | Earias spp. |
| B.661 | XN | Ephestia spp. |
| B.662 | XN | Heliothis spp. |
| B.663 | XN | *Hellula undalis* |
| B.664 | XN | *Keiferia lycopersicella* |
| B.665 | XN | *Leucoptera scitella* |
| B.666 | XN | Lithocollethis spp. |
| B.667 | XN | *Lobesia botrana* |
| B.668 | XN | *Ostrinia nubilalis* |
| B.669 | XN | Pandemis spp. |
| B.670 | XN | *Pectinophora gossyp.* |
| B.671 | XN | *Phyllocnistis citrella* |
| B.672 | XN | Pieris spp. |
| B.673 | XN | *Plutella xylostella* |
| B.674 | XN | Scirpophaga spp. |
| B.675 | XN | Sesamia spp. |
| B.676 | XN | Sparganothis spp. |
| B.677 | XN | Spodoptera spp. |
| B.678 | XN | Tortrix spp. |
| B.679 | XN | Trichoplusia ni |
| B.680 | XN | Agriotes spp. |
| B.681 | XN | *Anthonomus grandis* |
| B.682 | XN | Curculio spp. |
| B.683 | XN | *Diabrotica balteata* |
| B.684 | XN | Leptinotarsa spp. |
| B.685 | XN | Lissorhoptrus spp. |
| B.686 | XN | Otiorhynchus spp. |
| B.687 | XN | Aleurothrixus spp. |
| B.688 | XN | Aleyrodes spp. |
| B.689 | XN | Aonidiella spp. |
| B.690 | XN | Aphididae spp. |

TABLE B-continued

| | AP | Control of |
|---|---|---|
| B.691 | XN | Aphis spp. |
| B.692 | XN | *Bemisia tabaci* |
| B.693 | XN | Empoasca spp. |
| B.694 | XN | Mycus spp. |
| B.695 | XN | Nephotettix spp. |
| B.696 | XN | Nilaparvata spp. |
| B.697 | XN | Pseudococcus spp. |
| B.698 | XN | Psylla spp. |
| B.699 | XN | Quadraspidiotus spp. |
| B.700 | XN | Schizaphis spp. |
| B.701 | XN | Trialeurodes spp. |
| B.702 | XN | Lyriomyza spp. |
| B.703 | XN | Oscinella spp. |
| B.704 | XN | Phorbia spp. |
| B.705 | XN | Frankliniella spp. |
| B.706 | XN | Thrips spp. |
| B.707 | XN | *Scirtothrips aurantii* |
| B.708 | XN | Aceria spp. |
| B.709 | XN | Aculus spp. |
| B.710 | XN | Brevipalpus spp. |
| B.711 | XN | Panonychus spp. |
| B.712 | XN | Phyllocoptruta spp. |
| B.713 | XN | Tetranychus spp. |
| B.714 | XN | Heterodera spp. |
| B.715 | XN | Meloidogyne spp. |
| B.716 | Plnh. | Adoxophyes spp. |
| B.717 | Plnh. | Agrotis spp. |
| B.718 | Plnh. | *Alabama argillaceae* |
| B.719 | Plnh. | *Anticarsia gemmatalis* |
| B.720 | Plnh. | Chilo spp. |
| B.721 | Plnh. | *Clysia ambiguella* |
| B.722 | Plnh. | *Crocidolomia binotalis* |
| B.723 | Plnh. | Cydia spp. |
| B.724 | Plnh. | *Diparopsis castanea* |
| B.725 | Plnh. | Earias spp. |
| B.726 | Plnh. | Ephestia spp. |
| B.727 | Plnh. | Heliothis spp. |
| B.728 | Plnh. | *Hellula undalis* |
| B.729 | Plnh. | *Keiferia lycopersicella* |
| B.730 | Plnh. | *Leucoptera scitella* |
| B.731 | Plnh. | Lithocollethis spp. |
| B.732 | Plnh. | *Lobesia botrana* |
| B.733 | Plnh. | *Ostrinia nubilalis* |
| B.734 | Plnh. | Pandemis spp. |
| B.735 | Plnh. | *Pectinophora gossyp.* |
| B.736 | Plnh. | *Phyllocnistis citrella* |
| B.737 | Plnh. | Pieris spp. |
| B.738 | Plnh. | *Plutella xylostella* |
| B.739 | Plnh. | Scirpophaga spp. |
| B.740 | Plnh. | Sesamia spp. |
| B.741 | Plnh. | Sparganothis spp. |
| B.742 | Plnh. | Spodoptera spp. |
| B.743 | Plnh. | Tortrix spp. |
| B.744 | Plnh. | Trichoplusia ni |
| B.745 | Plnh. | Agriotes spp. |
| B.746 | Plnh. | *Anthonomus grandis* |
| B.747 | Plnh. | Curculio spp. |
| B.748 | Plnh. | *Diabrotica balteata* |
| B.749 | Plnh. | Leptinotarsa spp. |
| B.750 | Plnh. | Lissorhoptrus spp. |
| B.751 | Plnh. | Otiorhynchus spp. |
| B.752 | Plnh. | Aleurothrixus spp. |
| B.753 | Plnh. | Aleyrodes spp. |
| B.754 | Plnh. | Aonidiella spp. |
| B.755 | Plnh. | Aphididae spp. |
| B.756 | Plnh. | Aphis spp. |
| B.757 | Plnh. | *Bemisia tabaci* |
| B.758 | Plnh. | Empoasca spp. |
| B.759 | Plnh. | Mycus spp. |
| B.760 | Plnh. | Nephotettix spp. |
| B.761 | Plnh. | Nilaparvata spp. |
| B.762 | Plnh. | Pseudococcus spp. |
| B.763 | Plnh. | Psylla spp. |
| B.764 | Plnh. | Quadraspidiotus spp. |
| B.765 | Plnh. | Schizaphis spp. |
| B.766 | Plnh. | Trialeurodes spp. |
| B.767 | Plnh. | Lyriomyza spp. |
| B.768 | Plnh. | Oscinella spp. |
| B.769 | Plnh. | Phorbia spp. |
| B.770 | Plnh. | Frankliniella spp. |
| B.771 | Plnh. | Thrips spp. |
| B.772 | Plnh. | *Scirtothrips aurantii* |
| B.773 | Plnh. | Aceria spp. |
| B.774 | Plnh. | Aculus spp. |
| B.775 | Plnh. | Brevipalpus spp. |
| B.776 | Plnh. | Panonychus spp. |
| B.777 | Plnh. | Phyllocoptruta spp. |
| B.778 | Plnh. | Tetranychus spp. |
| B.779 | Plnh. | Heterodera spp. |
| B.780 | Plnh. | Meloidogyne spp. |
| B.781 | PLec. | Adoxophyes spp. |
| B.782 | PLec. | Agrotis spp. |
| B.783 | PLec. | *Alabama argillaceae* |
| B.784 | PLec. | *Anticarsia gemmatalis* |
| B.785 | PLec. | Chilo spp. |
| B.786 | PLec. | *Clysia ambiguella* |
| B.787 | PLec. | *Crocidolomia binotalis* |
| B.788 | PLec. | Cydia spp. |
| B.789 | PLec. | *Diparopsis castanea* |
| B.790 | PLec. | Earias spp. |
| B.791 | PLec. | Ephestia spp. |
| B.792 | PLec. | Heliothis spp. |
| B.793 | PLec. | *Hellula undalis* |
| B.794 | PLec. | *Keiferia lycopersicella* |
| B.795 | PLec. | *Leucoptera scitella* |
| B.796 | PLec. | Lithocollethis spp. |
| B.797 | PLec. | *Lobesia botrana* |
| B.798 | PLec. | *Ostrinia nubilalis* |
| B.799 | PLec. | Pandemis spp. |
| B.800 | PLec. | *Pectinophora gossyp.* |
| B.801 | PLec. | *Phyllocnistis citrella* |
| B.802 | PLec. | Pieris spp. |
| B.803 | PLec. | *Plutella xylostella* |
| B.804 | PLec. | Scirpophaga spp. |
| B.805 | PLec. | Sesamia spp. |
| B.806 | PLec. | Sparganothis spp. |
| B.807 | PLec. | Spodoptera spp. |
| B.808 | PLec. | Tortrix spp. |
| B.809 | PLec. | Trichoplusia ni |
| B.810 | PLec. | Agriotes spp. |
| B.811 | PLec. | *Anthonomus grandis* |
| B.812 | PLec. | Curculio spp. |
| B.813 | PLec. | *Diabrotica balteata* |
| B.814 | PLec. | Leptinotarsa spp. |
| B.815 | PLec. | Lissorhoptrus spp. |
| B.816 | PLec. | Otiorhynchus spp. |
| B.817 | PLec. | Aleurothrixus spp. |
| B.818 | PLec. | Aleyrodes spp. |
| B.819 | PLec. | Aonidiella spp. |
| B.820 | PLec. | Aphididae spp. |
| B.821 | PLec. | Aphis spp. |
| B.822 | PLec. | *Bemisia tabaci* |
| B.823 | PLec. | Empoasca spp. |
| B.824 | PLec. | Mycus spp. |
| B.825 | PLec. | Nephotettix spp. |
| B.826 | PLec. | Nilaparvata spp. |
| B.827 | PLec. | Pseudococcus spp. |
| B.828 | PLec. | Psylla spp. |

TABLE B-continued

| | AP | Control of |
|---|---|---|
| B.829 | PLec. | Quadraspidiotus spp. |
| B.830 | PLec. | Schizaphis spp. |
| B.831 | PLec. | Trialeurodes spp. |
| B.832 | PLec. | Lyriomyza spp. |
| B.833 | PLec. | Oscinella spp. |
| B.834 | PLec. | Phorbia spp. |
| B.835 | PLec. | Frankliniella spp. |
| B.836 | PLec. | Thrips spp. |
| B.837 | PLec. | Scirtothrips aurantii |
| B.838 | PLec. | Aceria spp. |
| B.839 | PLec. | Aculus spp. |
| B.840 | PLec. | Brevipalpus spp. |
| B.841 | PLec. | Panonychus spp. |
| B.842 | PLec. | Phyllocoptruta spp. |
| B.843 | PLec. | Tetranychus spp. |
| B.844 | PLec. | Heterodera spp. |
| B.845 | PLec. | Meloidogyne spp. |
| B.846 | Aggl. | Adoxophyes spp. |
| B.847 | Aggl. | Agrotis spp. |
| B.848 | Aggl. | Alabama argillaceae |
| B.849 | Aggl. | Anticarsia gemmatalis |
| B.850 | Aggl. | Chilo spp. |
| B.851 | Aggl. | Clysia ambiguella |
| B.852 | Aggl. | Crocidolomia binotalis |
| B.853 | Aggl. | Cydia spp. |
| B.854 | Aggl. | Diparopsis castanea |
| B.855 | Aggl. | Earias spp. |
| B.856 | Aggl. | Ephestia spp. |
| B.857 | Aggl. | Heliothis spp. |
| B.858 | Aggl. | Hellula undalis |
| B.859 | Aggl. | Keiferia lycopersicella |
| B.860 | Aggl. | Leucoptera scitella |
| B.861 | Aggl. | Lithocollethis spp. |
| B.862 | Aggl. | Lobesia botrana |
| B.863 | Aggl. | Ostrinia nubilalis |
| B.864 | Aggl. | Pandemis spp. |
| B.865 | Aggl. | Pectinophora gossyp. |
| B.866 | Aggl. | Phyllocnistis citrella |
| B.867 | Aggl. | Pieris spp. |
| B.868 | Aggl. | Plutella xylostella |
| B.869 | Aggl. | Scirpophaga spp. |
| B.870 | Aggl. | Sesamia spp. |
| B.871 | Aggl. | Sparganothis spp. |
| B.872 | Aggl. | Spodoptera spp. |
| B.873 | Aggl. | Tortrix spp. |
| B.874 | Aggl. | Trichoplusia ni |
| B.875 | Aggl. | Agriotes spp. |
| B.876 | Aggl. | Anthonomus grandis |
| B.877 | Aggl. | Curculio spp. |
| B.878 | Aggl. | Diabrotica balteata |
| B.879 | Aggl. | Leptinotarsa spp. |
| B.880 | Aggl. | Lissorhoptrus spp. |
| B.881 | Aggl. | Otiorhynchus spp. |
| B.882 | Aggl. | Aleurothrixus spp. |
| B.883 | Aggl. | Aleyrodes spp. |
| B.884 | Aggl. | Aonidiella spp. |
| B.885 | Aggl. | Aphididae spp. |
| B.886 | Aggl. | Aphis spp. |
| B.887 | Aggl. | Bemisia tabaci |
| B.888 | Aggl. | Empoasca spp. |
| B.889 | Aggl. | Mycus spp. |
| B.890 | Aggl. | Nephotettix spp. |
| B.891 | Aggl. | Nilaparvata spp. |
| B.892 | Aggl. | Pseudococcus spp. |
| B.893 | Aggl. | Psylla spp. |
| B.894 | Aggl. | Quadraspidiotus spp. |
| B.895 | Aggl. | Schizaphis spp. |
| B.896 | Aggl. | Trialeurodes spp. |
| B.897 | Aggl. | Lyriomyza spp. |
| B.898 | Aggl. | Oscinella spp. |
| B.899 | Aggl. | Phorbia spp. |
| B.900 | Aggl. | Frankliniella spp. |
| B.901 | Aggl. | Thrips spp. |
| B.902 | Aggl. | Scirtothrips aurantii |
| B.903 | Aggl. | Aceria spp. |
| B.904 | Aggl. | Aculus spp. |
| B.905 | Aggl. | Brevipalpus spp. |
| B.906 | Aggl. | Panonychus spp. |
| B.907 | Aggl. | Phyllocoptruta spp. |
| B.908 | Aggl. | Tetranychus spp. |
| B.909 | Aggl. | Heterodera spp. |
| B.910 | Aggl. | Meloidogyne spp. |
| B.911 | CO | Adoxophyes spp. |
| B.912 | CO | Agrotis spp. |
| B.913 | CO | Alabama argillaceae |
| B.914 | CO | Anticarsia gemmatalis |
| B.915 | CO | Chilo spp. |
| B.916 | CO | Clysia ambiguella |
| B.917 | CO | Crocidolomia binotalis |
| B.918 | CO | Cydia spp. |
| B.919 | CO | Diparopsis castanea |
| B.920 | CO | Earias spp. |
| B.921 | CO | Ephestia spp. |
| B.922 | CO | Heliothis spp. |
| B.923 | CO | Hellula undalis |
| B.924 | CO | Keiferia lycopersicella |
| B.925 | CO | Leucoptera scitella |
| B.926 | CO | Lithocollethis spp. |
| B.927 | CO | Lobesia botrana |
| B.928 | CO | Ostrinia nubilalis |
| B.929 | CO | Pandemis spp. |
| B.930 | CO | Pectinophora gossyp. |
| B.931 | CO | Phyllocnistis citrella |
| B.932 | CO | Pieris spp. |
| B.933 | CO | Plutella xylostella |
| B.934 | CO | Scirpophaga spp. |
| B.935 | CO | Sesamia spp. |
| B.936 | CO | Sparganothis spp. |
| B.937 | CO | Spodoptera spp. |
| B.938 | CO | Tortrix spp. |
| B.939 | CO | Trichoplusia ni |
| B.940 | CO | Agriotes spp. |
| B.941 | CO | Anthonomus grandis |
| B.942 | CO | Curculio spp. |
| B.943 | CO | Diabrotica balteata |
| B.944 | CO | Leptinotarsa spp. |
| B.945 | CO | Lissorhoptrus spp. |
| B.946 | CO | Otiorhynchus spp. |
| B.947 | CO | Aleurothrixus spp. |
| B.948 | CO | Aleyrodes spp. |
| B.949 | CO | Aonidiella spp. |
| B.950 | CO | Aphididae spp. |
| B.951 | CO | Aphis spp. |
| B.952 | CO | Bemisia tabaci |
| B.953 | CO | Empoasca spp. |
| B.954 | CO | Mycus spp. |
| B.955 | CO | Nephotettix spp. |
| B.956 | CO | Nilaparvata spp. |
| B.957 | CO | Pseudococcus spp. |
| B.958 | CO | Psylla spp. |
| B.959 | CO | Quadraspidiotus spp. |
| B.960 | CO | Schizaphis spp. |
| B.961 | CO | Trialeurodes spp. |
| B.962 | CO | Lyriomyza spp. |
| B.963 | CO | Oscinella spp. |
| B.964 | CO | Phorbia spp. |
| B.965 | CO | Frankliniella spp. |

TABLE B-continued

| | AP | Control of |
|---|---|---|
| B.966 | CO | Thrips spp. |
| B.967 | CO | *Scirtothrips aurantii* |
| B.968 | CO | Aceria spp. |
| B.969 | CO | Aculus spp. |
| B.970 | CO | Brevipalpus spp. |
| B.971 | CO | Panonychus spp. |
| B.972 | CO | Phyllocoptruta spp. |
| B.973 | CO | Tetranychus spp. |
| B.974 | CO | Heterodera spp. |
| B.975 | CO | Meloidogyne spp. |
| B.976 | CH | Adoxophyes spp. |
| B.977 | CH | Agrotis spp. |
| B.978 | CH | *Alabama argillaceae* |
| B.979 | CH | *Anticarsia gemmatalis* |
| B.980 | CH | Chilo spp. |
| B.981 | CH | *Clysia ambiguella* |
| B.982 | CH | *Crocidolomia binotalis* |
| B.983 | CH | Cydia spp. |
| B.984 | CH | *Diparopsis castanea* |
| B.985 | CH | Earias spp. |
| B.986 | CH | Ephestia spp. |
| B.987 | CH | Heliothis spp. |
| B.988 | CH | *Hellula undalis* |
| B.989 | CH | *Keiferia lycopersicella* |
| B.990 | CH | *Leucoptera scitella* |
| B.991 | CH | Lithocollethis spp. |
| B.992 | CH | *Lobesia botrana* |
| B.993 | CH | *Ostrinia nubilalis* |
| B.994 | CH | Pandemis spp. |
| B.995 | CH | *Pectinophora gossyp.* |
| B.996 | CH | *Phyllocnistis citrella* |
| B.997 | CH | Pieris spp. |
| B.998 | CH | *Plutella xylostella* |
| B.999 | CH | Scirpophaga spp. |
| B.1000 | CH | Sesamia spp. |
| B.1001 | CH | Sparganothis spp. |
| B.1002 | CH | Spodoptera spp. |
| B.1003 | CH | Tortrix spp. |
| B.1004 | CH | Trichoplusia ni |
| B.1005 | CH | Agriotes spp. |
| B.1006 | CH | *Anthonomus grandis* |
| B.1007 | CH | Curculio spp. |
| B.1008 | CH | *Diabrotica balteata* |
| B.1009 | CH | Leptinotarsa spp. |
| B.1010 | CH | Lissorhoptrus spp. |
| B.1011 | CH | Otiorhynchus spp. |
| B.1012 | CH | Aleurothrixus spp. |
| B.1013 | CH | Aleyrodes spp. |
| B.1014 | CH | Aonidiella spp. |
| B.1015 | CH | Aphididae spp. |
| B.1016 | CH | Aphis spp. |
| B.1017 | CH | *Bemisia tabaci* |
| B.1018 | CH | Empoasca spp. |
| B.1019 | CH | Mycus spp. |
| B.1020 | CH | Nephotettix spp. |
| B.1021 | CH | Nilaparvata spp. |
| B.1022 | CH | Pseudococcus spp. |
| B.1023 | CH | Psylla spp. |
| B.1024 | CH | Quadraspidiotus spp. |
| B.1025 | CH | Schizaphis spp. |
| B.1026 | CH | Trialeurodes spp. |
| B.1027 | CH | Lyriomyza spp. |
| B.1028 | CH | Oscinella spp. |
| B.1029 | CH | Phorbia spp. |
| B.1030 | CH | Frankliniella spp. |
| B.1031 | CH | Thrips spp. |
| B.1032 | CH | *Scirtothrips aurantii* |
| B.1033 | CH | Aceria spp. |
| B.1034 | CH | Aculus spp. |
| B.1035 | CH | Brevipalpus spp. |
| B.1036 | CH | Panonychus spp. |
| B.1037 | CH | Phyllocoptruta spp. |
| B.1038 | CH | Tetranychus spp. |
| B.1039 | CH | Heterodera spp. |
| B.1040 | CH | Meloidogyne spp. |
| B.1041 | SS | Adoxophyes spp. |
| B.1042 | SS | Agrotis spp. |
| B.1043 | SS | *Alabama argillaceae* |
| B.1044 | SS | *Anticarsia gemmatalis* |
| B.1045 | SS | Chilo spp. |
| B.1046 | SS | *Clysia ambiguella* |
| B.1047 | SS | *Crocidolomia binotalis* |
| B.1048 | SS | Cydia spp. |
| B.1049 | SS | *Diparopsis castanea* |
| B.1050 | SS | Earias spp. |
| B.1051 | SS | Ephestia spp. |
| B.1052 | SS | Heliothis spp. |
| B.1053 | SS | *Hellula undalis* |
| B.1054 | SS | *Keiferia lycopersicella* |
| B.1055 | SS | *Leucoptera scitella* |
| B.1056 | SS | Lithocollethis spp. |
| B.1057 | SS | *Lobesia botrana* |
| B.1058 | SS | *Ostrinia nubilalis* |
| B.1059 | SS | Pandemis spp. |
| B.1060 | SS | *Pectinophora gossyp.* |
| B.1061 | SS | *Phyllocnistis citrella* |
| B.1062 | SS | Pieris spp. |
| B.1063 | SS | *Plutella xylostella* |
| B.1064 | SS | Scirpophaga spp. |
| B.1065 | SS | Sesamia spp. |
| B.1066 | SS | Sparganothis spp. |
| B.1067 | SS | Spodoptera spp. |
| B.1068 | SS | Tortrix spp. |
| B.1069 | SS | Trichoplusia ni |
| B.1070 | SS | Agriotes spp. |
| B.1071 | SS | *Anthonomus grandis* |
| B.1072 | SS | Curculio spp. |
| B.1073 | SS | *Diabrotica balteata* |
| B.1074 | SS | Leptinotarsa spp. |
| B.1075 | SS | Lissorhoptrus spp. |
| B.1076 | SS | Otiorhynchus spp. |
| B.1077 | SS | Aleurothrixus spp. |
| B.1078 | SS | Aleyrodes spp. |
| B.1079 | SS | Aonidiella spp. |
| B.1080 | SS | Aphididae spp. |
| B.1081 | SS | Aphis spp. |
| B.1082 | SS | *Bemisia tabaci* |
| B.1083 | SS | Empoasca spp. |
| B.1084 | SS | Mycus spp. |
| B.1085 | SS | Nephotettix spp. |
| B.1086 | SS | Nilaparvata spp. |
| B.1087 | SS | Pseudococcus spp. |
| B.1088 | SS | Psylla spp. |
| B.1089 | SS | Quadraspidiotus spp. |
| B.1090 | SS | Schizaphis spp. |
| B.1091 | SS | Trialeurodes spp. |
| B.1092 | SS | Lyriomyza spp. |
| B.1093 | SS | Oscinella spp. |
| B.1094 | SS | Phorbia spp. |
| B.1095 | SS | Frankliniella spp. |
| B.1096 | SS | Thrips spp. |
| B.1097 | SS | *Scirtothrips aurantii* |
| B.1098 | SS | Aceria spp. |
| B.1099 | SS | Aculus spp. |
| B.1100 | SS | Brevipalpus spp. |
| B.1101 | SS | Panonychus spp. |
| B.1102 | SS | Phyllocoptruta spp. |
| B.1103 | SS | Tetranychus spp. |

TABLE B-continued

| | AP | Control of |
|---|---|---|
| B.1104 | SS | Heterodera spp. |
| B.1105 | SS | Meloidogyne spp. |
| B.1106 | HO | Adoxophyes spp. |
| B.1107 | HO | Agrotis spp. |
| B.1108 | HO | *Alabama argillaceae* |
| B.1109 | HO | *Anticarsia gemmatalis* |
| B.1110 | HO | Chilo spp. |
| B.1111 | HO | *Clysia ambiguella* |
| B.1112 | HO | *Crocidolomia binotalis* |
| B.1113 | HO | Cydia spp. |
| B.1114 | HO | *Diparopsis castanea* |
| B.1115 | HO | Earias spp. |
| B.1116 | HO | Ephestia spp. |
| B.1117 | HO | Heliothis spp. |
| B.1118 | HO | *Hellula undalis* |
| B.1119 | HO | *Keiferia lycopersicella* |
| B.1120 | HO | Leucoptera scitella |
| B.1121 | HO | Lithocollethis spp. |
| B.1122 | HO | *Lobesia botrana* |
| B.1123 | HO | *Ostrinia nubilalis* |
| B.1124 | HO | Pandemis spp. |
| B.1125 | HO | *Pectinophora gossypiella* |
| B.1126 | HO | *Phyllocnistis citrella* |
| B.1127 | HO | Pieris spp. |
| B.1128 | HO | *Plutella xylostella* |
| B.1129 | HO | Scirpophaga spp. |
| B.1130 | HO | Sesamia spp. |
| B.1131 | HO | Sparganothis spp. |
| B.1132 | HO | Spodoptera spp. |
| B.1133 | HO | Tortrix spp. |
| B.1134 | HO | Trichoplusia ni |
| B.1135 | HO | Agriotes spp. |
| B.1136 | HO | *Anthonomus grandis* |
| B.1137 | HO | Curculio spp. |
| B.1138 | HO | *Diabrotica balteata* |
| B.1139 | HO | Leptinotarsa spp. |
| B.1140 | HO | Lissorhoptrus spp. |
| B.1141 | HO | Otiorhynchus spp. |
| B.1142 | HO | Aleurothrixus spp. |
| B.1143 | HO | Aleyrodes spp. |
| B.1144 | HO | Aonidiella spp. |
| B.1145 | HO | Aphididae spp. |
| B.1146 | HO | Aphis spp. |
| B.1147 | HO | *Bemisia tabaci* |
| B.1148 | HO | Empoasca spp. |
| B.1149 | HO | Mycus spp. |
| B.1150 | HO | Nephotettix spp. |
| B.1151 | HO | Nilaparvata spp. |
| B.1152 | HO | Pseudococcus spp. |
| B.1153 | HO | Psylla spp. |
| B.1154 | HO | Quadraspidiotus spp. |
| B.1155 | HO | Schizaphis spp. |
| B.1156 | HO | Trialeurodes spp. |
| B.1157 | HO | Lyriomyza spp. |
| B.1158 | HO | Oscinella spp. |
| B.1159 | HO | Phorbia spp. |
| B.1160 | HO | Frankliniella spp. |
| B.1161 | HO | Thrips spp. |
| B.1162 | HO | *Scirtothrips aurantii* |
| B.1163 | HO | Aceria spp. |
| B.1164 | HO | Aculus spp. |
| B.1165 | HO | Brevipalpus spp. |
| B.1166 | HO | Panonychus spp. |
| B.1167 | HO | Phyllocoptruta spp. |
| B.1168 | HO | Tetranychus spp. |
| B.1169 | HO | Heterodera spp. |
| B.1170 | HO | Meloidogyne spp. |

BIOLOGICAL EXAMPLES

TABLE 1

A method of controlling pests comprising the application of Abamectin to transgenic cotton, wherein the combination of the active principle expressed by the transgenic plant and the pest to be controlled correspond to a line of the table B.

TABLE 2

A method of controlling pests comprising the application of Abamectin to transgenic rice, wherein the combination of the active principle expressed by the transgenic plant and the pest to be controlled correspond to a line of the table B.

TABLE 3

A method of controlling pests comprising the application of Abamectin to transgenic potatoes, wherein the combination of the active principle expressed by the transgenic plant and the pest to be controlled correspond to a line of the table B.

TABLE 4

A method of controlling pests comprising the application of Abamectin to transgenic brassica, wherein the combination of the active principle expressed by the transgenic plant and the pest to be controlled correspond to a line of the table B.

TABLE 5

A method of controlling pests comprising the application of Abamectin to transgenic tomatoes, wherein the combination of the active principle expressed by the transgenic plant and the pest to be controlled correspond to a line of the table B.

TABLE 6

A method of controlling pests comprising the application of Abamectin to transgenic cucurbits, wherein the combination of the active principle expressed by the transgenic plant and the pest to be controlled correspond to a line of the table B.

TABLE 7

A method of controlling pests comprising the application of Abamectin to transgenic soybeans, wherein the combination of the active principle expressed by the transgenic plant and the pest to be controlled correspond to a line of the table B.

TABLE 8

A method of controlling pests comprising the application of Abamectin to transgenic maize, wherein the combination of the active principle expressed by the transgenic plant and the pest to be controlled correspond to a line of the table B.

TABLE 9

A method of controlling pests comprising the application of Abamectin to transgenic wheat, wherein the combination of the active principle expressed by the transgenic plant and the pest to be controlled correspond to a line of the table B.

TABLE 10

A method of controlling pests comprising the application of Abamectin to transgenic bannanas, wherein the combination of the active principle expressed by the transgenic plant and the pest to be controlled correspond to a line of the table B.

TABLE 11

A method of controlling pests comprising the application of Abamectin to transgenic citrus trees, wherein the combination of the active principle expressed by the transgenic plant and the pest to be controlled correspond to a line of the table B.

TABLE 12

A method of controlling pests comprising the application of Abamectin to transgenic pome fruit trees, wherein the combination of the active principle expressed by the transgenic plant and the pest to be controlled correspond to a line of the table B.

TABLE 13

A method of controlling pests comprising the application of Emamectin-Benzoate to transgenic cotton, wherein the combination of the active principle expressed by the transgenic plant and the pest to be controlled correspond to a line of the table B.

TABLE 14

A method of controlling pests comprising the application of Emamectin-Benzoate to transgenic rice, wherein the combination of the active principle expressed by the transgenic plant and the pest to be controlled correspond to a line of the table B.

TABLE 15

A method of controlling pests comprising the application of Emamectin-Benzoate to transgenic potatoes, wherein the combination of the active principle expressed by the transgenic plant and the pest to be controlled correspond to a line of the table B.

TABLE 16

A method of controlling pests comprising the application of Emamectin-Benzoate to transgenic tomatoes, wherein the combination of the active principle expressed by the transgenic plant and the pest to be controlled correspond to a line of the table B.

TABLE 17

A method of controlling pests comprising the application of Emamectin-Benzoate to transgenic cucurbits, wherein the combination of the active principle expressed by the transgenic plant and the pest to be controlled correspond to a line of the table B.

TABLE 18

A method of controlling pests comprising the application of Emamectin-Benzoate to transgenic soybeans, wherein the combination of the active principle expressed by the transgenic plant and the pest to be controlled correspond to a line of the table B.

TABLE 19

A method of controlling pests comprising the application of Emamectin-Benzoate to transgenic maize, wherein the combination of the active principle expressed by the transgenic plant and the pest to be controlled correspond to a line of the table B.

TABLE 20

A method of controlling pests comprising the application of Emamectin-Benzoate to transgenic wheat, wherein the combination of the active principle expressed by the transgenic plant and the pest to be controlled correspond to a line of the table B.

TABLE 21

A method of controlling pests comprising the application of Emamectin-Benzoate to transgenic bananas, wherein the combination of the active principle expressed by the transgenic plant and the pest to be controlled correspond to a line of the table B.

TABLE 22

A method of controlling pests comprising the application of Emamectin-Benzoate to transgenic orange trees, wherein the combination of the active principle expressed by the transgenic plant and the pest to be controlled correspond to a line of the table B.

TABLE 23

A method of controlling pests comprising the application of Emamectin-Benzoate to transgenic pome fruit, wherein the combination of the active principle expressed by the transgenic plant and the pest to be controlled correspond to a line of the table B.

TABLE 24

A method of controlling pests comprising the application of Emamectin-Benzoate to transgenic cucurbits, wherein the combination of the active principle expressed by the transgenic plant and the pest to be controlled correspond to a line of the table B.

TABLE 25

A method of controlling pests comprising the application of Spinosad to transgenic cotton, wherein the combination of the active principle expressed by the transgenic plant and the pest to be controlled correspond to a line of the table B.

TABLE 26

A method of controlling pests comprising the application of Spinosad to transgenic rice, wherein the combination of the active principle expressed by the transgenic plant and the pest to be controlled correspond to a line of the table B.

TABLE 27

A method of controlling pests comprising the application of Spinosad to transgenic potatoes, wherein the combination of the active principle expressed by the transgenic plant and the pest to be controlled correspond to a line of the table B.

TABLE 28

A method of controlling pests comprising the application of Spinosad to transgenic brassica, wherein the combination of the active principle expressed by the transgenic plant and the pest to be controlled correspond to a line of the table B.

TABLE 29

A method of controlling pests comprising the application of Spinosad to transgenic tomatoes, wherein the combination of the active principle expressed by the transgenic plant and the pest to be controlled correspond to a line of the table B.

TABLE 30

A method of controlling pests comprising the application of Spinosad to transgenic cucurbits, wherein the combination of the active principle expressed by the transgenic plant and the pest to be controlled correspond to a line of the table B.

TABLE 31

A method of controlling pests comprising the application of Spinosad to transgenic soybeans, wherein the combination of the active principle expressed by the transgenic plant and the pest to be controlled correspond to a line of the table B.

TABLE 32

A method of controlling pests comprising the application of Spinosad to transgenic maize, wherein the combination of the active principle expressed by the transgenic plant and the pest to be controlled correspond to a line of the table B.

TABLE 33

A method of controlling pests comprising the application of Spinosad to transgenic wheat, wherein the combination of the active principle expressed by the transgenic plant and the pest to be controlled correspond to a line of the table B.

TABLE 34

A method of controlling pests comprising the application of Spinosad to transgenic bananas, wherein the combination of the active principle expressed by the transgenic plant and the pest to be controlled correspond to a line of the table B.

TABLE 35

A method of controlling pests comprising the application of Spinosad to transgenic citrus trees, wherein the combination of the active principle expressed by the transgenic plant and the pest to be controlled correspond to a line of the table B.

TABLE 36

A method of controlling pests comprising the application of Spinosad to transgenic pome fruit trees, wherein the combination of the active principle expressed by the transgenic plant and the pest to be controlled correspond to a line of the table B.

TABLE C

Abbreviations:
Acetyl-COA Carboxylase: ACCCase
Acetolactate Synthase: ALS
Hydroxyphenylpyruvat dioxygenase: HPPD
Inhibition of protein synthesis: IPS
Hormone mimic: HO
Glutamine Synthetase: GS
Protoporphyrinogen oxidase: PROTOX
5-Enolpyruvyl-3-Phosphoshikimate Synthase: EPSPS

| | Principle | Tolerant to | Crop |
|---|---|---|---|
| C.1 | ALS | Sulfonylureas etc.*** | Cotton |
| C.2 | ALS | Sulfonylureas etc.*** | Rice |
| C.3 | ALS | Sulfonylureas etc.*** | Brassica |
| C.4 | ALS | Sulfonylureas etc.*** | Potatoes |
| C.5 | ALS | Sulfonylureas etc.*** | Tomatoes |
| C.6 | ALS | Sulfonylureas etc.*** | Cucurbits |
| C.7 | ALS | Sulfonylureas etc.*** | Soybeans |
| C.8 | ALS | Sulfonylureas etc.*** | Maize |
| C.9 | ALS | Sulfonylureas etc.*** | Wheat |
| C.10 | ALS | Sulfonylureas etc.*** | pome fruit |
| C.11 | ALS | Sulfonylureas etc.*** | stone fruit |
| C.12 | ALS | Sulfonylureas etc.*** | citrus |
| C.13 | ACCase | +++ | Cotton |
| C.14 | ACCase | +++ | Rice |
| C.15 | ACCase | +++ | Brassica |
| C.16 | ACCase | +++ | Potatoes |
| C.17 | ACCase | +++ | Tomatoes |
| C.18 | ACCase | +++ | Cucurbits |
| C.19 | ACCase | +++ | Soybeans |
| C.20 | ACCase | +++ | Maize |
| C.21 | ACCase | +++ | Wheat |
| C.22 | ACCase | +++ | pome fruit |
| C.23 | ACCase | +++ | stone fruit |
| C.24 | ACCase | +++ | citrus |
| C.25 | HPPD | Isoxaflutol, Isoxachlotol, Sulcotrion, Mesotrion | Cotton |

TABLE C-continued

Abbreviations:
Acetyl-COA Carboxylase: ACCCase
Acetolactate Synthase: ALS
Hydroxyphenylpyruvat dioxygenase: HPPD
Inhibition of protein synthesis: IPS
Hormone mimic: HO
Glutamine Synthetase: GS
Protoporphyrinogen oxidase: PROTOX
5-Enolpyruvyl-3-Phosphoshikimate Synthase: EPSPS

| | Principle | Tolerant to | Crop |
|---|---|---|---|
| C.26 | HPPD | Isoxaflutol, Isoxachlotol, Sulcotrion, Mesotrion | Rice |
| C.27 | HPPD | Isoxaflutol, Isoxachlotol, Sulcotrion, Mesotrion | Brassica |
| C.28 | HPPD | Isoxaflutol, Isoxachlotol, Sulcotrion, Mesotrion | Potatoes |
| C.29 | HPPD | Isoxaflutol, Isoxachlotol, Sulcotrion, Mesotrion | Tomatoes |
| C.30 | HPPD | Isoxaflutol, Isoxachlotol, Sulcotrion, Mesotrion | Cucurbits |
| C.31 | HPPD | Isoxaflutol, Isoxachlotol, Sulcotrion, Mesotrion | Soybeans |
| C.32 | HPPD | Isoxaflutol, Isoxachlotol, Sulcotrion, Mesotrion | Maize |
| C.33 | HPPD | Isoxaflutol, Isoxachlotol, Sulcotrion, Mesotrion | Wheat |
| C.34 | HPPD | Isoxaflutol, Isoxachlotol, Sulcotrion, Mesotrion | pome fruit |
| C.35 | HPPD | Isoxaflutol, Isoxachlotol, Sulcotrion, Mesotrion | stone fruit |
| C.36 | HPPD | Isoxaflutol, Isoxachlotol, Sulcotrion, Mesotrion | citrus |
| C.37 | Nitrilase | Bromoxynil, Ioxynil | Cotton |
| C.38 | Nitrilase | Bromoxynil, Ioxynil | Rice |
| C.39 | Nitrilase | Bromoxynil, Ioxynil | Brassica |
| C.40 | Nitrilase | Bromoxynil, Ioxynil | Potatoes |
| C.41 | Nitrilase | Bromoxynil, Ioxynil | Tomatoes |
| C.42 | Nitrilase | Bromoxynil, Ioxynil | Cucurbits |
| C.43 | Nitrilase | Bromoxynil, Ioxynil | Soybeans |
| C.44 | Nitrilase | Bromoxynil, Ioxynil | Maize |
| C.45 | Nitrilase | Bromoxynil, Ioxynil | Wheat |
| C.46 | Nitrilase | Bromoxynil, Ioxynil | pome fruit |
| C.47 | Nitrilase | Bromoxynil, Ioxynil | stone fruit |
| C.48 | Nitrilase | Bromoxynil, Ioxynil | citrus |
| C.49 | IPS | Chloroactanilides &&& | Cotton |
| C.50 | IPS | Chloroactanilides &&& | Rice |
| C.51 | IPS | Chloroactanilides &&&s | Brassica |
| C.52 | IPS | Chloroactanilides &&& | Potatoes |
| C.53 | IPS | Chloroactanilides &&& | Tomatoes |
| C.54 | IPS | Chloroactanilides &&& | Cucurbits |
| C.55 | IPS | Chloroactanilides &&& | Soybeans |
| C.56 | IPS | Chloroactanilides &&& | Maize |
| C.57 | IPS | Chloroactanilides &&& | Wheat |
| C.58 | IPS | Chloroactanilides &&& | pome fruit |
| C.59 | IPS | Chloroactanilides &&& | stone fruit |
| C.60 | IPS | Chloroactanilides &&& | citrus |
| C.61 | HOM | 2,4-D, Mecoprop-P | Cotton |
| C.62 | HOM | 2,4-D, Mecoprop-P | Rice |
| C.63 | HOM | 2,4-D, Mecoprop-P | Brassica |
| C.64 | HOM | 2,4-D, Mecoprop-P | Potatoes |
| C.65 | HOM | 2,4-D, Mecoprop-P | Tomatoes |
| C.66 | HOM | 2,4-D, Mecoprop-P | Cucurbits |
| C.67 | HOM | 2,4-D, Mecoprop-P | Soybeans |
| C.68 | HOM | 2,4-D, Mecoprop-P | Maize |
| C.69 | HOM | 2,4-D, Mecoprop-P | Wheat |
| C.70 | HOM | 2,4-D, Mecoprop-P | pome fruit |
| C.71 | HOM | 2,4-D, Mecoprop-P | stone fruit |
| C.72 | HOM | 2,4-D, Mecoprop-P | citrus |
| C.73 | PROTOX | Protox inhibitors /// | Cotton |
| C.74 | PROTOX | Protox inhibitors /// | Rice |
| C.75 | PROTOX | Protox inhibitors /// | Brassica |
| C.76 | PROTOX | Protox inhibitors /// | Potatoes |
| C.77 | PROTOX | Protox inhibitors /// | Tomatoes |
| C.78 | PROTOX | Protox inhibitors /// | Cucurbits |
| C.79 | PROTOX | Protox inhibitors /// | Soybeans |
| C.80 | PROTOX | Protox inhibitors /// | Maize |
| C.81 | PROTOX | Protox inhibitors /// | Wheat |
| C.82 | PROTOX | Protox inhibitors /// | pome fruit |
| C.83 | PROTOX | Protox inhibitors /// | stone fruit |
| C.84 | PROTOX | Protox inhibitors /// | citrus |
| C.85 | EPSPS | Glyphosate and/or Sulphosate | Cotton |
| C.86 | EPSPS | Glyphosate and/or Sulphosate | Rice |
| C.87 | EPSPS | Glyphosate and/or Sulphosate | Brassica |
| C.88 | EPSPS | Glyphosate and/or Sulphosate | Potatoes |
| C.89 | EPSPS | Glyphosate and/or Sulphosate | Tomatoes |
| C.90 | EPSPS | Glyphosate and/or Sulphosate | Cucurbits |
| C.91 | EPSPS | Glyphosate and/or Sulphosate | Soybeans |
| C.92 | EPSPS | Glyphosate and/or Sulphosate | Maize |
| C.93 | EPSPS | Glyphosate and/or Sulphosate | Wheat |
| C.94 | EPSPS | Glyphosate and/or Sulphosate | pome fruit |
| C.95 | EPSPS | Glyphosate and/or Sulphosate | stone fruit |
| C.96 | EPSPS | Glyphosate and/or Sulphosate | citrus |
| C.97 | GS | Gluphosinate and/or Bialaphos | Cotton |
| C.98 | GS | Gluphosinate and/or Bialaphos | Rice |
| C.99 | GS | Gluphosinate and/or Bialaphos | Brassica |
| C.100 | GS | Gluphosinate and/or Bialaphos | Potatoes |
| C.101 | GS | Gluphosinate and/or Bialaphos | Tomatoes |
| C.102 | GS | Gluphosinate and/or Bialaphos | Cucurbits |
| C.103 | GS | Gluphosinate and/or Bialaphos | Soybeans |
| C.104 | GS | Gluphosinate and/or Bialaphos | Maize |
| C.105 | GS | Gluphosinate and/or Bialaphos | Wheat |
| C.106 | GS | Gluphosinate and/or Bialaphos | pome fruit |
| C.107 | GS | Gluphosinate and/or Bialaphos | stone fruit |
| C.108 | GS | Gluphosinate and/or Bialaphos | citrus |

\*\*\*Included are Sulfonylureas, Imidazolinones, Triazolopyrimidines, Dimethoxypyrimidines and N-Acylsulfonamides: Sulfonylureas such as Chlorsulfuron, Chlorimuron, Ethametsulfuron, Metsulfuron, Primisulfuron, Prosulfuron, Triasulfuron, Cinosulfuron, Trifusulfuron, Oxasulfuron, Bensulfuron, Tribenuron, ACC 322140, Fluzasulfuron, Ethoxysulfuron, Fluzasdulfuron, Nicosulfuron, Rimsulfuron, Thifensulfuron, Pyrazosulfuron, Clopyrasulfuron, NC 330,Azimsulfuron, Imazosulfuron, Sulfosulfuron, Amidosulfuron, Flupyrsulfuron, CGA 362622 Imidazolinones such as lmazamethabenz, Imazaquin, Imazamethypyr, Imazethapyr, Imazapyr and Imazamox; Triazolopyrimidines such as DE 511, Flumetsulam and Chloransulam; Dimethoxypyrimidines such as Pyrithiobac, Pyriminobac, Bispyribac and Pyribenzoxim.

+++ Tolerant to Diclofop-methyl, Fluazifop-P-butyl, Haloxyfop-P-methyl, Haloxyfop-P-ethyl, Quizalafop-P-ethyl, clodinafop propargyl, fenoxaprop-ethyl, - Tepraloxydim, Alloxydim, Sethoxydim, Cycloxydim, Cloproxydim, Tralkoxydim, Butoxydim, Caloxydim, Clefoxydim, Clethodim.

&&& Chloroacetanilides such as Alachlor Acetochlor, Dimethenamid

/// Protox inhibitors: For instance diphenyethers such as Acifluorfen, Aclonifen, Bifenox, Chlornitrofen, Ethoxyfen, Fluoroglycofen, Fomesafen, Lactofen, Oxyfluorfen; Imides such as Azafenidin, Carfentrazone-ethyl, Cinidon-ethyl, Flumiclorac-pentyl, Flumioxazin, Fluthiacet-methyl, Oxadiargyl, Oxadiazon, Pentoxazone, Sulfentrazone, Imides and others, such as Flumipropyn, Flupropacil, Nipyraclofen and Thidiazimin; and further Fluazolate and Pyraflufen-ethyl

BIOLOGICAL EXAMPLES

TABLE 39

A method of controlling representatives of the genus *Adoxophyes* comprising the application of Abamectin to a herbicidally resistant transgenic crop, wherein the combination of the active principle expressed by the transgenic plant and the crop to be protected against the pest correspond to a line of the table C.

TABLE 40

A method of controlling representatives of the genus *Argotis* comprising the application of Abamectin to a herbicidally resistant transgenic crop, wherein the combination of the active principle expressed by the transgenic plant and the crop to be protected against the pest correspond to a line of the table C.

TABLE 41

A method of controlling *Alabama argillaceae* comprising the application of Abamectin to a herbicidally transgenic resistant crop, wherein the combination of the active principle expressed by the transgenic plant and the crop to be protected against the pest correspond to a line of the table C.

TABLE 42

A method of controlling *Anticarsia gemmatalis* comprising the application application of Abamectin to a herbicidally transgenic resistant crop, wherein the combination of the active principle expressed by the transgenic plant and the crop to be protected against the pest correspond to a line of the table C.

TABLE 43

A method of controlling representatives of the genus *Chilo* comprising the application of Abamectin to a herbicidally resistant transgenic crop, wherein the combination of the active principle expressed by the transgenic plant and the crop to be protected against the pest correspond to a line of the table C.

TABLE 44

A method of controlling *Clysia ambiguella* comprising the application of Abamectin to a herbicidally resistant transgenic crop, wherein the combination of the active principle expressed by the transgenic plant and the crop to be protected against the pest correspond to a line of the table C.

TABLE 45

A method of controlling representatives of the genus *Cnephalocrocis* comprising the application of Abamectin to a herbicidally resistant transgenic crop, wherein the combination of the active principle expressed by the transgenic plant and the crop to be protected aagainst the pest correspond to a line of the table C.

TABLE 46

A method of controlling *Crocidolomia binotalis* comprising the application of Abamectin to a herbicidally resistant transgenic crop, wherein the combination of the active principle expressed by the transgenic plant and the crop to be protected against the pest correspond to a line of the table C.

TABLE 47

A method of controlling representatives of the genus *Cydia* comprising the application of Abamectin to a herbicidally resistant transgenic crop, wherein the combination of the active principle expressed by the transgenic plant and the crop to be protected aagainst the pest correspond to a line of the table C.

TABLE 48

A method of controlling *Diparopsis castanea* comprising the application of Abamectin to a herbicidally resistant transgenic crop, wherein the combination of the active principle expressed by the transgenic plant and the crop to be protected against the pest correspond to a line of the table C.

TABLE 49

A method of controlling representatives of the genus *Earias* comprising the application of Abamectin to a herbicidally resistant transgenic crop, wherein the combination of the active principle expressed by the transgenic plant and the crop to be protected aagainst the pest correspond to a line of the table C.

TABLE 50

A method of controlling representatives of the genus *Ephestia* comprising the application of Abamectin to a herbicidally resistant transgenic crop, wherein the combination of the active principle expressed by the transgenic plant and the crop to be protected aagainst the pest correspond to a line of the table C.

TABLE 51

A method of controlling representatives of the genus *Heliothis* comprising the application of Abamectin to a herbicidally resistant transgenic crop, wherein the combination of the active principle expressed by the transgenic plant and the crop to be protected aagainst the pest correspond to a line of the table C.

TABLE 52

A method of controlling *Hellula undalis* comprising the application of Abamectin to a herbicidally resistant transgenic crop, wherein the combination of the active principle expressed by the transgenic plant and the crop to be protected against the pest correspond to a line of the table C.

TABLE 53

A method of controlling *Keiferia lycopersicella* comprising the application of Abamectin to a herbicidally resistant transgenic crop, wherein the combination of the active principle expressed by the transgenic plant and the crop to be protected against the pest correspond to a line of the table C.

TABLE 54

A method of controlling *Leucoptera scitella* comprising the application of Abamectin to a herbicidally resistant transgenic crop, wherein the combination of the active principle expressed by the transgenic plant and the crop to be protected against the pest correspond to a line of the table C.

TABLE 55

A method of controlling representatives of the genus *Lithocollethis* comprising the application of Abamectin to a herbicidally resistant transgenic crop, wherein the combination of the active principle expressed by the transgenic plant and the crop to be protected aagainst the pest correspond to a line of the table C.

TABLE 56

A method of controlling *Lobesia botrana* comprising the application of Abamectin to a herbicidally resistant transgenic crop, wherein the combination of the active principle expressed by the transgenic plant and the crop to be protected against the pest correspond to a line of the table C.

TABLE 57

A method of controlling *Ostrinia nubilalis* comprising the application of Abamectin to a herbicidally resistant transgenic crop, wherein the combination of the active principle expressed by the transgenic plant and the crop to be protected against the pest correspond to a line of the table C.

TABLE 58

A method of controlling representatives of the genus *Pandemis* comprising the application of Abamectin to a herbicidally resistant transgenic crop, wherein the combination of the active principle expressed by the transgenic plant and the crop to be protected aagainst the pest correspond to a line of the table C.

TABLE 59

A method of controlling *Pectinophora gossypiella* comprising the application of Abamectin to a herbicidally resistant transgenic crop, wherein the combination of the active principle expressed by the transgenic plant and the crop to be protected against the pest correspond to a line of the table C.

TABLE 60

A method of controlling *Phyllocnistis citrella* comprising the application of Abamectin to a herbicidally resistant transgenic crop, wherein the combination of the active principle expressed by the transgenic plant and the crop to be protected against the pest correspond to a line of the table C.

TABLE 61

A method of controlling representatives of the genus *Pieris* comprising the application of Abamectin to a herbicidally resistant transgenic crop, wherein the combination of the active principle expressed by the transgenic plant and the crop to be protected aagainst the pest correspond to a line of the table C.

TABLE 62

A method of controlling *Plutella xylostella* comprising the application of Abamectin to a herbicidally resistant transgenic crop, wherein the combination of the active principle expressed by the transgenic plant and the crop to be protected against the pest correspond to a line of the table C.

TABLE 63

A method of controlling representatives of the genus *Scirpophaga* comprising the application of Abamectin to a herbicidally resistant transgenic crop, wherein the combination of the active principle expressed by the transgenic plant and the crop to be protected against the pest correspond to a line in the table C.

TABLE 64

A method of controlling representatives of the genus *Sesamia* comprising the application of Abamectin to a herbicidally resistant transgenic crop, wherein the combination of the active principle expressed by the transgenic plant and the crop to be protected against the pest correspond to a line in the table C.

TABLE 65

A method of controlling representatives of the genus *Sparganothis* comprising the application of Abamectin to a herbicidally resistant transgenic crop, wherein the combination of the active principle expressed by the transgenic plant and the crop to be protected against the pest correspond to a line in the table C.

TABLE 66

A method of controlling representatives of the genus *Spodoptera* comprising the application of Abamectin to a herbicidally resistant transgenic crop, wherein the combination of the active principle expressed by the transgenic plant and the crop to be protected against the pest correspond to a line in the table C.

TABLE 67

A method of controlling representatives of the genus *Tortrix* comprising the application of Abamectin to a herbicidally resistant transgenic crop, wherein the combination of the active principle expressed by the transgenic plant and the crop to be protected against the pest correspond to a line in the table C.

TABLE 68

A method of controlling *Trichoplusia ni* comprising the application of Abamectin to a herbicidally resistant transgenic crop, wherein the combination of the active principle expressed by the transgenic plant and the crop to be protected against the pest correspond to a line in the table C.

TABLE 69

A method of controlling representatives of the genus *Agriotes* comprising the application of Abamectin to a herbicidally resistant transgenic crop, wherein the combination of the active principle expressed by the transgenic plant and the crop to be protected against the pest correspond to a line in the table C.

TABLE 70

A method of controlling *Anthonomus grandis* comprising the application of Abamectin to a herbicidally resistant transgenic crop, wherein the combination of the active principle expressed by the transgenic plant and the crop to be protected against the pest correspond to a line in the table C.

TABLE 71

A method of controlling representatives of the genus *Curculio* comprising the application of Abamectin to a herbicidally resistant transgenic crop, wherein the combination of the active principle expressed by the transgenic plant and the crop to be protected against the pest correspond to a line in the table C.

TABLE 72

A method of controlling *Diabrotica balteata* comprising the application of Abamectin to a herbicidally resistant transgenic crop, wherein the combination of the active principle expressed by the transgenic plant and the crop to be protected against the pest correspond to a line in the table C.

TABLE 73

A method of controlling representatives of the genus *Leptinotarsa* comprising the application of Abamectin to a herbicidally resistant transgenic crop, wherein the combination of the active principle expressed by the transgenic plant and the crop to be protected against the pest correspond to a line in the table C.

TABLE 74

A method of controlling representatives of the genus *Lissorhoptrus* comprising the application of Abamectin to a herbicidally resistant transgenic crop, wherein the combination of the active principle expressed by the transgenic plant and the crop to be protected against the pest correspond to a line in the table C.

TABLE 75

A method of controlling representatives of the genus *Otiorhynchus* comprising the application of Abamectin to a herbicidally resistant transgenic crop, wherein the combination of the active principle expressed by the transgenic plant and the crop to be protected against the pest correspond to a line in the table C.

TABLE 76

A method of controlling representatives of the genus *Aleurothrixus* comprising the application of Abamectin to a herbicidally resistant transgenic crop, wherein the combination of the active principle expressed by the transgenic plant and the crop to be protected against the pest correspond to a line in the table C.

TABLE 77

A method of controlling representatives of the genus *Aleyrodes* comprising the application of Abamectin to a herbicidally resistant transgenic crop, wherein the combination of the active principle expressed by the transgenic plant and the crop to be protected against the pest correspond to a line in the table C.

TABLE 78

A method of controlling representatives of the genus *Aonidiella* comprising the application of Abamectin to a herbicidally resistant transgenic crop, wherein the combination of the active principle expressed by the transgenic plant and the crop to be protected against the pest correspond to a line in the table C.

TABLE 79

A method of controlling representatives of the family Aphididae comprising the application of Abamectin to a herbicidally resistant transgenic crop, wherein the combination of the active principle expressed by the transgenic plant and the crop to be protected against the pest correspond to a line in the table C.

TABLE 80

A method of controlling representatives of the genus *Aphis* comprising the application of Abamectin to a herbicidally resistant transgenic crop, wherein the combination of the active principle expressed by the transgenic plant and the crop to be protected against the pest correspond to a line in the table C.

TABLE 81

A method of controlling *Bemisia tabaci* comprising the application of Abamectin to a herbicidally resistant transgenic crop, wherein the combination of the active principle expressed by the transgenic plant and the crop to be protected against the pest correspond to a line in the table C.

TABLE 82

A method of controlling representatives of the genus *Empoasca* comprising the application of Abamectin to a herbicidally resistant transgenic crop, wherein the combination of the active principle expressed by the transgenic plant and the crop to be protected against the pest correspond to a line in the table C.

TABLE 83

A method of controlling representatives of the genus *Mycus* comprising the application of Abamectin to a herbicidally resistant transgenic crop, wherein the combination of the active principle expressed by the transgenic plant and the crop to be protected against the pest correspond to a line of the table C.

TABLE 84

A method of controlling representatives of the genus *Nephotettix* comprising the application of Abamectin to a herbicidally resistant transgenic crop, wherein the combination of the active principle expressed by the transgenic plant and the crop to be protected against the pest correspond to a line of the table C.

TABLE 85

A method of controlling representatives of the genus *Nilaparvata* comprising the application of Abamectin to a herbicidally resistant transgenic crop, wherein the combination of the active principle expressed by the transgenic plant and the crop to be protected against the pest correspond to a line of the table C.

TABLE 86

A method of controlling representatives of the genus *Pseudoccocus* comprising the application of Abamectin to a herbicidally resistant transgenic crop, wherein the combination of the active principle expressed by the transgenic plant and the crop to be protected against the pest correspond to a line of the table C.

TABLE 87

A method of controlling representatives of the genus *Psylla* comprising the application of Abamectin to a herbicidally resistant transgenic crop, wherein the combination of the active principle expressed by the transgenic plant and the crop to be protected against the pest correspond to a line of the table C.

TABLE 88

A method of controlling representatives of the genus *Quadraspidiotus* comprising the application of Abamectin to a herbicidally resistant transgenic crop, wherein the combination of the active principle expressed by the transgenic plant and the crop to be protected against the pest correspond to a line of the table C.

TABLE 89

A method of controlling representatives of the genus *Schizaphis* comprising the application of Abamectin to a herbicidally resistant transgenic crop, wherein the combination of the active principle expressed by the transgenic plant and the crop to be protected against the pest correspond to a line of the table C.

TABLE 90

A method of controlling representatives of the genus *Trialeurodes* comprising the application of Abamectin to a herbicidally resistant transgenic crop, wherein the combination of the active principle expressed by the transgenic plant and the crop to be protected against the pest correspond to a line of the table C.

TABLE 91

A method of controlling representatives of the genus *Lyriomyza* comprising the application of Abamectin to a herbicidally resistant transgenic crop, wherein the combination of the active principle expressed by the transgenic plant and the crop to be protected against the pest correspond to a line of the table C.

TABLE 92

A method of controlling representatives of the genus *Oscinella* comprising the application of Abamectin to a herbicidally resistant transgenic crop, wherein the combination of the active principle expressed by the transgenic plant and the crop to be protected against the pest correspond to a line of the table C.

TABLE 93

A method of controlling representatives of the genus *Phorbia* comprising the application of Abamectin to a herbicidally resistant transgenic crop, wherein the combination of the active principle expressed by the transgenic plant and the crop to be protected against the pest correspond to a line of the table C.

TABLE 94

A method of controlling representatives of the genus *Frankliniella* comprising the application of Abamectin to a herbicidally resistant transgenic crop, wherein the combination of the active principle expressed by the transgenic plant and the crop to be protected against the pest correspond to a line of the table C.

TABLE 95

A method of controlling representatives of the genus *Thrips* comprising the application of Abamectin to a herbicidally resistant transgenic crop, wherein the combination of the active principle expressed by the transgenic plant and the crop to be protected against the pest correspond to a line of the table C.

TABLE 96

| |
|---|
| A method of controlling *Scirtothrips aurantii* comprising the application of Abamectin to a herbicidally resistant transgenic crop, wherein the combination of the active principle expressed by the transgenic plant and the crop to be protected against the pest correspond to a line of the table C. |

TABLE 97

| |
|---|
| A method of controlling representatives of the genus *Aceria* comprising the application of Abamectin to a herbicidally resistant transgenic crop, wherein the combination of the active principle expressed by the transgenic plant and the crop to be protected against the pest correspond to a line of the table C. |

TABLE 98

| |
|---|
| A method of controlling representatives of the genus *Aculus* comprising the application of Abamectin to a herbicidally resistant transgenic crop, wherein the combination of the active principle expressed by the transgenic plant and the crop to be protected against the pest correspond to a line of the table C. |

TABLE 99

| |
|---|
| A method of controlling representatives of the genus *Brevipalpus* comprising the application of Abamectin to a herbicidally resistant transgenic crop, wherein the combination of the active principle expressed by the transgenic plant and the crop to be protected against the pest correspond to a line of the table C. |

TABLE 100

| |
|---|
| A method of controlling representatives of the genus *Panonychus* comprising the application of Abamectin to a herbicidally resistant transgenic crop, wherein the combination of the active principle expressed by the transgenic plant and the crop to be protected against the pest correspond to a line of the table C. |

TABLE 101

| |
|---|
| A method of controlling representatives of the genus *Phyllocoptruta* comprising the application of Abamectin to a herbicidally resistant transgenic crop, wherein the combination of the active principle expressed by the transgenic plant and the crop to be protected against the pest correspond to a line of the table C. |

TABLE 102

| |
|---|
| A method of controlling representatives of the genus *Tetranychus* comprising the application of Abamectin to a herbicidally resistant transgenic crop, wherein the combination of the active principle expressed by the transgenic plant and the crop to be protected against the pest correspond to a line of the table C. |

TABLE 103

| |
|---|
| A method of controlling representatives of the genus *Heterodera* comprising the application of Abamectin to a hebicidally resistant transgenic crop, wherein the combination of the active principle expressed by the transgenic plant and the crop to be protected against the pest correspond to a line of the table C. |

TABLE 104

| |
|---|
| A method of controlling representatives of the genus *Meloidogyne* comprising the application of Abamectin to a hebicidally resistant transgenic crop, wherein the combination of the active principle expressed by the transgenic plant and the crop to be protected against the pest correspond to a line of the table C. |

TABLE 105

| |
|---|
| A method of controlling *Memestra brassica* comprising the application of Abamectin to a hebicidally resistant transgenic crop, wherein the combination of the active principle expressed by the transgenic plant and the crop to be protected against the pest correspond to a line of the table C. |

TABLE 106

| |
|---|
| A method of controlling representatives of the genus *Adoxophyes* comprising the application of Emamectin-Benzoate to a hebicidally resistant transgenic crop, wherein the combination of the active principle expressed by the transgenic plant and the crop to be protected against the pest correspond to a line of the table C. |

TABLE 107

| |
|---|
| A method of controlling representatives of the genus *Argotis* comprising the application of Emamectin-benzoate to a hebicidally resistant transgenic crop, wherein the combination of the active principle expressed by the transgenic plant and the crop to be protected against the pest correspond to a line of the table C. |

TABLE 108

| |
|---|
| A method of controlling *Alabama argillaceae* comprising the application of Emamectin-benzoate to a hebicidally resistant transgenic crop, wherein the combination of the active principle expressed by the transgenic plant and the crop to be protected against the pest correspond to a line of the table C. |

TABLE 109

| |
|---|
| A method of controlling *Anticarsia gemmatalis* comprising the application of Emamectin-benzoate to a hebicidally resistant transgenic crop, wherein the combination of the active principle expressed by the transgenic plant and the crop to be protected against the pest correspond to a line of the table C. |

TABLE 110

A method of controlling representatives of the genus *Chilo* comprising the application of Emamectin-benzoate to a hebicidally resistant transgenic crop, wherein the combination of the active principle expressed by the transgenic plant and the crop to be protected against the pest correspond to a line of the table C.

TABLE 111

A method of controlling *Clysia ambiguella* comprising the application of Emamectin-benzoate to a hebicidally resistant transgenic crop, wherein the combination of the active principle expressed by the transgenic plant and the crop to be protected against the pest correspond to a line of the table C.

TABLE 112

A method of controlling representatives of the genus *Cnephalocrocis* comprising the application of Emamectin-benzoate to a hebicidally resistant transgenic crop, wherein the combination of the active principle expressed by the transgenic plant and the crop to be protected against the pest correspond to a line of the table C.

TABLE 113

A method of controlling *Crocidolomia binotalis* comprising the application of Emamectin-benzoate to a hebicidally resistant transgenic crop, wherein the combination of the active principle expressed by the transgenic plant and the crop to be protected against the pest correspond to a line of the table C.

TABLE 114

A method of controlling representatives of the genus *Cydia* comprising the application of Emamectin-benzoate to a hebicidally resistant transgenic crop, wherein the combination of the active principle expressed by the transgenic plant and the crop to be protected against the pest correspond to a line of the table C.

TABLE 115

A method of controlling *Diparopsis castanea* comprising the application of Emamectin-benzoate to a hebicidally resistant transgenic crop, wherein the combination of the active principle expressed by the transgenic plant and the crop to be protected against the pest correspond to a line of the table C.

TABLE 116

A method of controlling representatives of the genus *Earias* comprising the application of Emamectin-benzoate to a hebicidally resistant transgenic crop, wherein the combination of the active principle expressed by the transgenic plant and the crop to be protected against the pest correspond to a line of the table C.

TABLE 117

A method of controlling representatives of the genus *Ephestia* comprising the application of Emamectin-benzoate to a hebicidally resistant transgenic crop, wherein the combination of the active principle expressed by the transgenic plant and the crop to be protected against the pest correspond to a line of the table C.

TABLE 118

A method of controlling representatives of the genus *Heliothis* comprising the application of Emamectin-benzoate to a hebicidally resistant transgenic crop, wherein the combination of the active principle expressed by the transgenic plant and the crop to be protected against the pest correspond to a line of the table C.

TABLE 119

A method of controlling *Hellula undalis* comprising the application of Emamectin-benzoate to a hebicidally resistant transgenic crop, wherein the combination of the active principle expressed by the transgenic plant and the crop to be protected against the pest correspond to a line of the table C.

TABLE 120

A method of controlling *Keiferia lycopersicella* comprising the application of Emamectin-benzoate to a hebicidally resistant transgenic crop, wherein the combination of the active principle expressed by the transgenic plant and the crop to be protected against the pest correspond to a line of the table C.

TABLE 121

A method of controlling *Leucoptera scitella* comprising the application of Emamectin-benzoate to a hebicidally resistant transgenic crop, wherein the combination of the active principle expressed by the transgenic plant and the crop to be protected against the pest correspond to a line of the table C.

TABLE 122

A method of controlling representatives of the genus *Lithocollethis* comprising the application of Emamectin-benzoate to a hebicidally resistant transgenic crop, wherein the combination of the active principle expressed by the transgenic plant and the crop to be protected against the pest correspond to a line of the table C.

TABLE 123

A method of controlling *Lobesia botrana* comprising the application of Emamectin-benzoate to a hebicidally resistant transgenic crop, wherein the combination of the active principle expressed by the transgenic plant and the crop to be protected against the pest correspond to a line of the table C.

TABLE 124

| |
|---|
| A method of controlling *Ostrinia nubalis* comprising the application of Emamectin-benzoate to a hebicidally resistant transgenic crop, wherein the combination of the active principle expressed by the transgenic plant and the crop to be protected against the pest correspond to a line of the table C. |

TABLE 125

| |
|---|
| A method of controlling representatives of the genus *Pandemis* comprising the application of Emamectin-benzoate to a hebicidally resistant transgenic crop, wherein the combination of the active principle expressed by the transgenic plant and the crop to be protected against the pest correspond to a line of the table C. |

TABLE 126

| |
|---|
| A method of controlling *Pectinophora gossypiella* comprising the application of Emamectin-benzoate to a hebicidally resistant transgenic crop, wherein the combination of the active principle expressed by the transgenic plant and the crop to be protected against the pest correspond to a line of the table C. |

TABLE 127

| |
|---|
| A method of controlling *Phyllocnistis citrella* comprising the application of Emamectin-benzoate to a hebicidally resistant transgenic crop, wherein the combination of the active principle expressed by the transgenic plant and the crop to be protected against the pest correspond to a line of the table C. |

TABLE 128

| |
|---|
| A method of controlling representatives of the genus *Pieris* comprising the application of Emamectin-benzoate to a hebicidally resistant transgenic crop, wherein the combination of the active principle expressed by the transgenic plant and the crop to be protected against the pest correspond to a line of the table C. |

TABLE 129

| |
|---|
| A method of controlling *Plutella xylostella* comprising the application of Emamectin-benzoate to a hebicidally resistant transgenic crop, wherein the combination of the active principle expressed by the transgenic plant and the crop to be protected against the pest correspond to a line of the table C. |

TABLE 130

| |
|---|
| A method of controlling representatives of the genus *Scirpophaga* comprising the application of Emamectin-benzoate to a hebicidally resistant transgenic crop, wherein the combination of the active principle expressed by the transgenic plant and the crop to be protected against the pest correspond to a line of the table C. |

TABLE 131

| |
|---|
| A method of controlling representatives of the genus *Sesamia* comprising the application of Emamectin-benzoate to a hebicidally resistant transgenic crop, wherein the combination of the active principle expressed by the transgenic plant and the crop to be protected against the pest correspond to a line of the table C. |

TABLE 132

| |
|---|
| A method of controlling representatives of the genus *Sparganothis* comprising the application of Emamectin-benzoate to a hebicidally resistant transgenic crop, wherein the combination of the active principle expressed by the transgenic plant and the crop to be protected against the pest correspond to a line of the table C. |

TABLE 133

| |
|---|
| A method of controlling representatives of the genus *Spodoptera* comprising the application of Emamectin-benzoate to a hebicidally resistant transgenic crop, wherein the combination of the active principle expressed by the transgenic plant and the crop to be protected against the pest correspond to a line of the table C. |

TABLE 134

| |
|---|
| A method of controlling representatives of the genus *Tortrix* comprising the application of Emamectin-benzoate to a hebicidally resistant transgenic crop, wherein the combination of the active principle expressed by the transgenic plant and the crop to be protected against the pest correspond to a line of the table C. |

TABLE 135

| |
|---|
| A method of controlling *Trichoplusia ni* comprising the application of Emamectin-benzoate to a hebicidally resistant transgenic crop, wherein the combination of the active principle expressed by the transgenic plant and the crop to be protected against the pest correspond to a line of the table C. |

TABLE 136

| |
|---|
| A method of controlling representatives of the genus *Agriotes* comprising the application of Emamectin-benzoate to a hebicidally resistant transgenic crop, wherein the combination of the active principle expressed by the transgenic plant and the crop to be protected against the pest correspond to a line of the table C. |

TABLE 137

| |
|---|
| A method of controlling *Anthonomus grandis* comprising the application of Emamectin-benzoate to a hebicidally resistant transgenic crop, wherein the combination of the active principle expressed by the transgenic plant and the crop to be protected against the pest correspond to a line of the table C. |

TABLE 138

A method of controlling representatives of the genus *Curculio* comprising the application of Emamectin-benzoate to a hebicidally resistant transgenic crop, wherein the combination of the active principle expressed by the transgenic plant and the crop to be protected against the pest correspond to a line of the table C.

TABLE 139

A method of controlling *Diabrotica balteata* comprising the application of Emamectin-benzoate to a hebicidally resistant transgenic crop, wherein the combination of the active principle expressed by the transgenic plant and the crop to be protected against the pest correspond to a line of the table C.

TABLE 140

A method of controlling representatives of the genus *Leptinotarsa* comprising the application of Emamectin-benzoate to a hebicidally resistant transgenic crop, wherein the combination of the active principle expressed by the transgenic plant and the crop to be protected against the pest correspond to a line of the table C.

TABLE 141

A method of controlling representatives of the genus *Lissorhoptrus* comprising the application of Emamectin-benzoate to a hebicidally resistant transgenic crop, wherein the combination of the active principle expressed by the transgenic plant and the crop to be protected against the pest correspond to a line of the table C.

TABLE 142

A method of controlling representatives of the genus *Otiorhynchus* comprising the application of Emamectin-benzoate to a hebicidally resistant transgenic crop, wherein the combination of the active principle expressed by the transgenic plant and the crop to be protected against the pest correspond to a line of the table C.

TABLE 143

A method of controlling representatives of the genus *Aleurothrixus* comprising the application of Emamectin-benzoate to a herbicidally resistant transgenic crop, wherein the combination of the active principle expressed by the transgenic plant and the crop to be protected against the pest correspond to a line of the table C.

TABLE 144

A method of controlling representatives of the genus *Aleyrodes* comprising the application of Emamectin-benzoate to a herbicidally resistant transgenic crop, wherein the combination of the active principle expressed by the transgenic plant and the crop to be protected against the pest correspond to a line of the table C.

TABLE 145

A method of controlling representatives of the genus *Aonidiella* comprising the application of Emamectin-benzoate to a herbicidally resistant transgenic crop, wherein the combination of the active principle expressed by the transgenic plant and the crop to be protected against the pest correspond to a line of the table C.

TABLE 146

A method of controlling representatives of the family Aphididae comprising the application of Emamectin-benzoate to a herbicidally resistant transgenic crop, wherein the combination of the active principle expressed by the transgenic plant and the crop to be protected against the pest correspond to a line of the table C.

TABLE 147

A method of controlling representatives of the genus *Aphis* comprising the application of Emamectin-benzoate to a herbicidally resistant transgenic crop, wherein the combination of the active principle expressed by the transgenic plant and the crop to be protected against the pest correspond to a line of the table C.

TABLE 148

A method of controlling *Bemisia tabaci* comprising the application of Emamectin-benzoate to a herbicidally resistant transgenic crop, wherein the combination of the active principle expressed by the transgenic plant and the crop to be protected against the pest correspond to a line of the table C.

TABLE 149

A method of controlling representatives of the genus *Empoasca* comprising the application of Emamectin-benzoate to a herbicidally resistant transgenic crop, wherein the combination of the active principle expressed by the transgenic plant and the crop to be protected against the pest correspond to a line of the table C.

TABLE 150

A method of controlling representatives of the genus *Mycus* comprising the application of Emamectin-benzoate to a herbicidally resistant transgenic crop, wherein the combination of the active principle expressed by the transgenic plant and the crop to be protected against the pest correspond to a line of the table C.

TABLE 151

A method of controlling representatives of the genus *Nephotettix* comprising the application of Emamectin-benzoate to a herbicidally resistant transgenic crop, wherein the combination of the active principle expressed by the transgenic plant and the crop to be protected against the pest correspond to a line of the table C.

TABLE 152

A method of controlling representatives of the genus *Nilaparvata* comprising the application of Emamectin-benzoate to a herbicidally resistant transgenic crop, wherein the combination of the active principle expressed by the transgenic plant and the crop to be protected against the pest correspond to a line of the table C.

TABLE 153

A method of controlling representatives of the genus *Pseudococcus* comprising the application of Emamectin-benzoate to a herbicidally resistant transgenic crop, wherein the combination of the active principle expressed by the transgenic plant and the crop to be protected against the pest correspond to a line of the table C.

TABLE 154

A method of controlling representatives of the genus *Psylla* comprising the application of Emamectin-benzoate to a herbicidally resistant transgenic crop, wherein the combination of the active principle expressed by the transgenic plant and the crop to be protected against the pest correspond to a line of the table C.

TABLE 155

A method of controlling representatives of the genus *Quadraspidiotus* comprising the application of Emamectin-benzoate to a herbicidally resistant transgenic crop, wherein the combination of the active principle expressed by the transgenic plant and the crop to be protected against the pest correspond to a line of the table C.

TABLE 156

A method of controlling representatives of the genus *Schizaphis* comprising the application of Emamectin-benzoate to a herbicidally resistant transgenic crop, wherein the combination of the active principle expressed by the transgenic plant and the crop to be protected against the pest correspond to a line of the table C.

TABLE 157

A method of controlling representatives of the genus *Trialeurodes* comprising the application of Emamectin-benzoate to a herbicidally resistant transgenic crop, wherein the combination of the active principle expressed by the transgenic plant and the crop to be protected against the pest correspond to a line of the table C.

TABLE 158

A method of controlling representatives of the genus *Lyriomyza* comprising the application of Emamectin-benzoate to a herbicidally resistant transgenic crop, wherein the combination of the active principle expressed by the transgenic plant and the crop to be protected against the pest correspond to a line of the table C.

TABLE 159

A method of controlling representatives of the genus *Oscinella* comprising the application of Emamectin-benzoate to a herbicidally resistant transgenic crop, wherein the combination of the active principle expressed by the transgenic plant and the crop to be protected against the pest correspond to a line of the table C.

TABLE 160

A method of controlling representatives of the genus *Phorbia* comprising the application of Emamectin-benzoate to a herbicidally resistant transgenic crop, wherein the combination of the active principle expressed by the transgenic plant and the crop to be protected against the pest correspond to a line of the table C.

TABLE 161

A method of controlling representatives of the genus *Frankliniella* comprising the application of Emamectin-benzoate to a herbicidally resistant transgenic crop, wherein the combination of the active principle expressed by the transgenic plant and the crop to be protected against the pest correspond to a line of the table C.

TABLE 162

A method of controlling representatives of the genus *Thrips* comprising the application of Emamectin-benzoate to a herbicidally resistant transgenic crop, wherein the combination of the active principle expressed by the transgenic plant and the crop to be protected against the pest correspond to a line of the table C.

TABLE 163

A method of controlling *Scirtothrips aurantii* comprising the application of Emamectin-benzoate to a herbicidally resistant transgenic crop, wherein the combination of the active principle expressed by the transgenic plant and the crop to be protected against the pest correspond to a line of the table C.

TABLE 164

A method of controlling representatives of the genus *Aceria* comprising the application of Emamectin-benzoate to a herbicidally resistant transgenic crop, wherein the combination of the active principle expressed by the transgenic plant and the crop to be protected against the pest correspond to a line of the table C.

TABLE 165

A method of controlling representatives of the genus *Aculus* comprising the application of Emamectin-benzoate to a herbicidally resistant transgenic crop, wherein the combination of the active principle expressed by the transgenic plant and the crop to be protected against the pest correspond to a line of the table C.

TABLE 166

A method of controlling representatives of the genus *Brevipalpus* comprising the application of Emamectin-benzoate to a herbicidally resistant transgenic crop, wherein the combination of the active principle expressed by the transgenic plant and the crop to be protected against the pest correspond to a line of the table C.

TABLE 167

A method of controlling representatives of the genus *Panonychus* comprising the application of Emamectin-benzoate to a herbicidally resistant transgenic crop, wherein the combination of the active principle expressed by the transgenic plant and the crop to be protected against the pest correspond to a line of the table C.

TABLE 168

A method of controlling representatives of the genus *Phyllocoptruta* comprising the application of Emamectin-benzoate to a herbicidally resistant transgenic crop, wherein the combination of the active principle expressed by the transgenic plant and the crop to be protected against the pest correspond to a line of the table C.

TABLE 169

A method of controlling representatives of the genus *Tetranychus* comprising the application of Emamectin-benzoate to a herbicidally resistant transgenic crop, wherein the combination of the active principle expressed by the transgenic plant and the crop to be protected against the pest correspond to a line of the table C.

TABLE 170

A method of controlling representatives of the genus *Heterodera* comprising the application of Emamectin-benzoate to a herbicidally resistant transgenic crop, wherein the combination of the active principle expressed by the transgenic plant and the crop to be protected against the pest correspond to a line of the table C.

TABLE 171

A method of controlling representatives of the genus *Meloidogyne* comprising the application of Emamectin-benzoate to a herbicidally resistant transgenic crop, wherein the combination of the active principle expressed by the transgenic plant and the crop to be protected against the pest correspond to a line of the table C.

TABLE 172

A method of controlling representatives of the genus *Adoxophyes* comprising the application of Spinosad to a herbicidally resistant transgenic crop, wherein the combination of the active principle expressed by the transgenic plant and the crop to be protected against the pest correspond to a line of the table C.

TABLE 173

A method of controlling representatives of the genus *Argotis* comprising the application of Spinosad to a herbicidally resistant transgenic crop, wherein the combination of the active principle expressed by the transgenic plant and the crop to be protected against the pest correspond to a line of the table C.

TABLE 174

A method of controlling *Alabama argillaceae* comprising the application of Spinosad to a herbicidally resistant transgenic crop, wherein the combination of the active principle expressed by the transgenic plant and the crop to be protected against the pest correspond to a line of the table C.

TABLE 175

A method of controlling *Anticarsia gemmatalis* comprising the application of Spinosad to a herbicidally resistant transgenic crop, wherein the combination of the active principle expressed by the transgenic plant and the crop to be protected against the pest correspond to a line of the table C.

TABLE 176

A method of controlling representatives of the genus *Chilo* comprising the application of Spinosad to a herbicidally resistant transgenic crop, wherein the combination of the active principle expressed by the transgenic plant and the crop to be protected against the pest correspond to a line of the table C.

TABLE 177

A method of controlling *Clysia ambiguella* comprising the application of Spinosad to a herbicidally resistant transgenic crop, wherein the combination of the active principle expressed by the transgenic plant and the crop to be protected against the pest correspond to a line of the table C.

TABLE 178

A method of controlling *Crocidolomia binotalis* comprising the application of Spinosad to a herbicidally resistant transgenic crop, wherein the combination of the active principle expressed by the transgenic plant and the crop to be protected against the pest correspond to a line of the table C.

TABLE 179

A method of controlling representatives of the genus *Cydia* comprising the application of Spinosad to a herbicidally resistant transgenic crop, wherein the combination of the active principle expressed by the transgenic plant and the crop to be protected against the pest correspond to a line of the table C.

TABLE 180

A method of controlling *Diparopsis castanea* comprising the application of Spinosad to a herbicidally resistant transgenic crop, wherein the combination of the active principle expressed by the transgenic plant and the crop to be protected against the pest correspond to a line of the table C.

TABLE 181

A method of controlling representatives of the genus *Earias* comprising the application of Spinosad to a herbicidally resistant transgenic crop, wherein the combination of the active principle expressed by the transgenic plant and the crop to be protected against the pest correspond to a line of the table C.

TABLE 182

A method of controlling representatives of the genus *Ephestia* comprising the application of Spinosad to a herbicidally resistant transgenic crop, wherein the combination of the active principle expressed by the transgenic plant and the crop to be protected against the pest correspond to a line of the table C.

TABLE 183

A method of controlling representatives of the genus *Heliothis* comprising the application of Spinosad to a herbicidally resistant transgenic crop, wherein the combination of the active principle expressed by the transgenic plant and the crop to be protected against the pest correspond to a line of the table C.

TABLE 184

A method of controlling *Hellula undalis* comprising the application of Spinosad to a hebicidally resistant transgenic crop, wherein the combination of the active principle expressed by the transgenic plant and the crop to be protected against the pest correspond to a line of the table C.

TABLE 185

A method of controlling *Keiferia lycopersicella* comprising the application of Spinosad to a hebicidally resistant transgenic crop, wherein the combination of the active principle expressed by the transgenic plant and the crop to be protected against the pest correspond to a line of the table C.

TABLE 186

A method of controlling *Leucoptera scitella* comprising the application of Spinosad to a hebicidally resistant transgenic crop, wherein the combination of the active principle expressed by the transgenic plant and the crop to be protected against the pest correspond to a line of the table C.

TABLE 187

A method of controlling representatives of the genus *Lithocollethis* comprising the application of Spinosad to a hebicidally resistant transgenic crop, wherein the combination of the active principle expressed by the transgenic plant and the crop to be protected against the pest correspond to a line of the table C.

TABLE 188

A method of controlling *Lobesia botrana* comprising the application of Spinosad to a hebicidally resistant transgenic crop, wherein the combination of the active principle expressed by the transgenic plant and the crop to be protected against the pest correspond to a line of the table C.

TABLE 189

A method of controlling *Ostrinia nubilalis* comprising the application of Spinosad to a hebicidally resistant transgenic crop, wherein the combination of the active principle expressed by the transgenic plant and the crop to be protected against the pest correspond to a line of the table C.

TABLE 190

A method of controlling representatives of the genus *Pandemis* comprising the application of Spinosad to a hebicidally resistant transgenic crop, wherein the combination of the active principle expressed by the transgenic plant and the crop to be protected against the pest correspond to a line of the table C.

TABLE 191

A method of controlling *Pectinophora gossypiella* comprising the application of Spinosad to a hebicidally resistant transgenic crop, wherein the combination of the active principle expressed by the transgenic plant and the crop to be protected against the pest correspond to a line of the table C.

TABLE 192

A method of controlling *Phyllocnistis citrella* comprising the application of Spinosad to a hebicidally resistant transgenic crop, wherein the combination of the active principle expressed by the transgenic plant and the crop to be protected against the pest correspond to a line of the table C.

TABLE 193

A method of controlling representatives of the genus *Pieris* comprising the application of Spinosad to a hebicidally resistant transgenic crop, wherein the combination of the active principle expressed by the transgenic plant and the crop to be protected against the pest correspond to a line of the table C.

TABLE 194

A method of controlling *Plutella xylostella* comprising the application of Spinosad to a hebicidally resistant transgenic crop, wherein the combination of the active principle expressed by the transgenic plant and the crop to be protected against the pest correspond to a line of the table C.

TABLE 195

A method of controlling representatives of the genus *Scirpophaga* comprising the application of Spinosad to a hebicidally resistant transgenic crop, wherein the combination of the active principle expressed by the transgenic plant and the crop to be protected against the pest correspond to a line of the table C.

TABLE 196

A method of controlling representatives of the genus *Sesamia* comprising the application of Spinosad to a hebicidally resistant transgenic crop, wherein the combination of the active principle expressed by the transgenic plant and the crop to be protected against the pest correspond to a line of the table C.

TABLE 197

A method of controlling representatives of the genus *Sparganothis* comprising the application of Spinosad to a hebicidally resistant transgenic crop, wherein the combination of the active principle expressed by the transgenic plant and the crop to be protected against the pest correspond to a line of the table C.

TABLE 198

A method of controlling representatives of the genus *Spodoptera* comprising the application of Spinosad to a hebicidally resistant transgenic crop, wherein the combination of the active principle expressed by the transgenic plant and the crop to be protected against the pest correspond to a line of the table C.

TABLE 199

A method of controlling representatives of the genus *Tortrix* comprising the application of Spinosad to a hebicidally resistant transgenic crop, wherein the combination of the active principle expressed by the transgenic plant and the crop to be protected against the pest correspond to a line of the table C.

TABLE 200

A method of controlling *Trichoplusia ni* comprising the application of Spinosad to a hebicidally resistant transgenic crop, wherein the combination of the active principle expressed by the transgenic plant and the crop to be protected against the pest correspond to a line of the table C.

TABLE 201

A method of controlling representatives of the genus *Agriotes* comprising the application of Spinosad to a hebicidally resistant transgenic crop, wherein the combination of the active principle expressed by the transgenic plant and the crop to be protected against the pest correspond to a line of the table C.

TABLE 202

A method of controlling *Anthonomus grandis* comprising the application of Spinosad to a hebicidally resistant transgenic crop, wherein the combination of the active principle expressed by the transgenic plant and the crop to be protected against the pest correspond to a line of the table C.

TABLE 203

A method of controlling representatives of the genus *Curculio* comprising the application of Spinosad to a herbicidally resistant transgenic crop, wherein the combination of the active principle expressed by the transgenic plant and the crop to be protected against the pest correspond to a line of the table C.

TABLE 204

A method of controlling *Diabrotica balteata* comprising the application of Spinosad to a herbicidally resistant transgenic crop, wherein the combination of the active principle expressed by the transgenic plant and the crop to be protected against the pest correspond to a line of the table C.

TABLE 205

A method of controlling representatives of the genus *Leptinotarsa* comprising the application of Spinosad to a herbicidally resistant transgenic crop, wherein the combination of the active principle expressed by the transgenic plant and the crop to be protected against the pest correspond to a line of the table C.

TABLE 206

A method of controlling representatives of the genus *Lissorhoptrus* comprising the application of Spinosad to a herbicidally resistant transgenic crop, wherein the combination of the active principle expressed by the transgenic plant and the crop to be protected against the pest correspond to a line of the table C.

TABLE 207

A method of controlling representatives of the genus *Otiorhynchus* comprising the application of Spinosad to a herbicidally resistant transgenic crop, wherein the combination of the active principle expressed by the transgenic plant and the crop to be protected against the pest correspond to a line of the table C.

TABLE 208

A method of controlling representatives of the genus *Aleurothrixus* comprising the application of Spinosad to a herbicidally resistant transgenic crop, wherein the combination of the active principle expressed by the transgenic plant and the crop to be protected against the pest correspond to a line of the table C.

TABLE 209

A method of controlling representatives of the genus *Aleyrodes* comprising the application of Spinosad to a herbicidally resistant transgenic crop, wherein the combination of the active principle expressed by the transgenic plant and the crop to be protected against the pest correspond to a line of the table C.

TABLE 210

A method of controlling representatives of the genus *Aonidiella* comprising the application of Spinosad to a herbicidally resistant transgenic crop, wherein the combination of the active principle expressed by the transgenic plant and the crop to be protected against the pest correspond to a line of the table C.

TABLE 211

A method of controlling representatives of the family Aphididae comprising the application of Spinosad to a herbicidally resistant transgenic crop, wherein the combination of the active principle expressed by the transgenic plant and the crop to be protected against the pest correspond to a line of the table C.

TABLE 212

A method of controlling representatives of the genus *Aphis* comprising the application of Spinosad to a herbicidally resistant transgenic crop, wherein the combination of the active principle expressed by the transgenic plant and the crop to be protected against the pest correspond to a line of the table C.

TABLE 213

A method of controlling *Bemisia tabaci* comprising the application of Spinosad to a herbicidally resistant transgenic crop, wherein the combination of the active principle expressed by the transgenic plant and the crop to be protected against the pest correspond to a line of the table C.

TABLE 214

A method of controlling representatives of the genus *Empoasca* comprising the application of Spinosad to a herbicidally resistant transgenic crop, wherein the combination of the active principle expressed by the transgenic plant and the crop to be protected against the pest correspond to a line of the table C.

TABLE 215

A method of controlling representatives of the genus *Mycus* comprising the application of Spinosad to a herbicidally resistant transgenic crop, wherein the combination of the active principle expressed by the transgenic plant and the crop to be protected against the pest correspond to a line of the table C.

TABLE 216

A method of controlling representatives of the genus *Nephotettix* comprising the application of Spinosad to a herbicidally resistant transgenic crop, wherein the combination of the active principle expressed by the transgenic plant and the crop to be protected against the pest correspond to a line of the table C.

TABLE 217

A method of controlling representatives of the genus *Nilaparvata* comprising the application of Spinosad to a herbicidally resistant transgenic crop, wherein the combination of the active principle expressed by the transgenic plant and the crop to be protected against the pest correspond to a line of the table C.

TABLE 218

A method of controlling representatives of the genus *Pseudococcus* comprising the application of Spinosad to a herbicidally resistant transgenic crop, wherein the combination of the active principle expressed by the transgenic plant and the crop to be protected against the pest correspond to a line of the table C.

TABLE 219

A method of controlling representatives of the genus *Psylla* comprising the application of Spinosad to a herbicidally resistant transgenic crop, wherein the combination of the active principle expressed by the transgenic plant and the crop to be protected against the pest correspond to a line of the table C.

TABLE 220

A method of controlling representatives of the genus *Quadraspidiotus* comprising the application of Spinosad to a herbicidally resistant transgenic crop, wherein the combination of the active principle expressed by the transgenic plant and the crop to be protected against the pest correspond to a line of the table C.

TABLE 221

A method of controlling representatives of the genus *Schizaphis* comprising the application of Spinosad to a herbicidally resistant transgenic crop, wherein the combination of the active principle expressed by the transgenic plant and the crop to be protected against the pest correspond to a line of the table C.

TABLE 222

A method of controlling representatives of the genus *Trialeurodes* comprising the application of Spinosad to a herbicidally resistant transgenic crop, wherein the combination of the active principle expressed by the transgenic plant and the crop to be protected against the pest correspond to a line of the table C.

TABLE 223

A method of controlling representatives of the genus *Lyriomyza* comprising the application of Spinosad to a herbicidally resistant transgenic crop, wherein the combination of the active principle expressed by the transgenic plant and the crop to be protected against the pest correspond to a line of the table C.

TABLE 224

A method of controlling representatives of the genus *Oscinella* comprising the application of Spinosad to a herbicidally resistant transgenic crop, wherein the combination of the active principle expressed by the transgenic plant and the crop to be protected against the pest correspond to a line of the table C.

TABLE 225

A method of controlling representatives of the genus *Phorbia* comprising the application of Spinosad to a herbicidally resistant transgenic crop, wherein the combination of the active principle expressed by the transgenic plant and the crop to be protected against the pest correspond to a line of the table C.

TABLE 226

A method of controlling representatives of the genus *Frankliniella* comprising the application of Spinosad to a herbicidally resistant transgenic crop, wherein the combination of the active principle expressed by the transgenic plant and the crop to be protected against the pest correspond to a line of the table C.

TABLE 227

A method of controlling representatives of the genus *Thrips* comprising the application of Spinosad to a herbicidally resistant transgenic crop, wherein the combination of the active principle expressed by the transgenic plant and the crop to be protected against the pest correspond to a line of the table C.

TABLE 228

A method of controlling *Scirtothrips aurantii* comprising the application of Spinosad to a herbicidally resistant transgenic crop, wherein the combination of the active principle expressed by the transgenic plant and the crop to be protected against the pest correspond to a line of the table C.

TABLE 229

A method of controlling representatives of the genus *Aceria* comprising the application of Spinosad to a herbicidally resistant transgenic crop, wherein the combination of the active principle expressed by the transgenic plant and the crop to be protected against the pest correspond to a line of the table C.

TABLE 230

A method of controlling representatives of the genus *Aculus* comprising the application of Spinosad to a herbicidally resistant transgenic crop, wherein the combination of the active principle expressed by the transgenic plant and the crop to be protected against the pest correspond to a line of the table C.

TABLE 231

A method of controlling representatives of the genus *Brevipalpus* comprising the application of Spinosad to a herbicidally resistant transgenic crop, wherein the combination of the active principle expressed by the transgenic plant and the crop to be protected against the pest correspond to a line of the table C.

TABLE 232

A method of controlling representatives of the genus *Panonychus* comprising the application of Spinosad to a herbicidally resistant transgenic crop, wherein the combination of the active principle expressed by the transgenic plant and the crop to be protected against the pest correspond to a line of the table C.

TABLE 233

A method of controlling representatives of the genus *Phyllocoptruta* comprising the application of Spinosad to a herbicidally resistant transgenic crop, wherein the combination of the active principle expressed by the transgenic plant and the crop to be protected against the pest correspond to a line of the table C.

TABLE 234

A method of controlling representatives of the genus *Tetranychus* comprising the application of Spinosad to a herbicidally resistant transgenic crop, wherein the combination of the active principle expressed by the transgenic plant and the crop to be protected against the pest correspond to a line of the table C.

TABLE 235

A method of controlling representatives of the genus *Heterodera* comprising the application of Spinosad to a herbicidally resistant transgenic crop, wherein the combination of the active principle expressed by the transgenic plant and the crop to be protected against the pest correspond to a line of the table C.

TABLE 236

A method of controlling representatives of the genus *Meloidogyne* comprising the application of Spinosad to a herbicidally resistant transgenic crop, wherein the combination of the active principle expressed by the transgenic plant and the crop to be protected against the pest correspond to a line of the table C.

TABLE 237

A method of controlling *Mamestra brassica* comprising the application of Spinosad to a herbicidally resistant transgenic crop, wherein the combination of the active principle expressed by the transgenic plant and the crop to be protected against the pest correspond to a line of the table C.

Example B1

Action Against *Anthonomus grandis* Adults,
*Spodoptera littoralis* or *Heliothis virescens*

Young transgenic cotton plants which express the δ-endotoxin CryIIIA are sprayed with an aqueous emulsion spray mixture comprising 100, 50, 10, 5, 1 ppm of emamectin-benzoate respectively. After the spray coating has dried on, the cotton plants are populated with 10 adult *Anthonomus grandis*, 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising emamectin-benzoate and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B2

Action Against *Anthonomus grandis* Adults,
*Spodoptera littoralis* or *Heliothis virescens*

Young transgenic cotton plants which express the δ-endotoxin CryIIIA are sprayed with an aqueous emulsion spray mixture comprising 100, 50, 10, 5, 1 ppm of abamectin respectively. After the spray coating has dried on, the cotton plants are populated with 10 adult *Anthonomus grandis*, 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising abamectin and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B3

Action Against *Anthonomus grandis* Adults,
*Spodoptera littoralis* or *Heliothis virescens*

Young transgenic cotton plants which express the δ-endotoxin CryIIIA are sprayed with an aqueous emulsion spray mixture comprising 100, 50, 10, 5, 1 ppm of spinosad respectively. After the spray coating has dried on, the cotton plants are populated with 10 adult *Anthonomus grandis*, 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising spinosad and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B4

Action Against *Anthonomus grandis* Adults,
*Spodoptera littoralis* or *Heliothis virescens*

Young transgenic cotton plants which express the δ-endotoxin CryIa(c) are sprayed with an aqueous emulsion spray mixture comprising 100, 50, 10, 5, 1 ppm of spinosad respectively. After the spray coating has dried on, the cotton plants are populated with 10 adult *Anthonomus grandis*, 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising spinosad and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B5

Action Against *Anthonomus grandis* Adults,
*Spodoptera littoralis* or *Heliothis virescens*

Young transgenic cotton plants which express the δ-endotoxin CryIa(c) are sprayed with an aqueous emulsion spray mixture comprising 100, 50, 10, 5, 1 ppm of abamectin respectively. After the spray coating has dried on, the cotton plants are populated with 10 adult *Anthonomus grandis*, 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising abamectin and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B6

Action Against *Anthonomus grandis* Adults,
*Spodoptera littoralis* or *Heliothis virescens*

Young transgenic cotton plants which express the δ-endotoxin CryIa(c) are sprayed with an aqueous emulsion spray mixture comprising 100, 50, 10, 5, 1 ppm of emamectin benzoate respectively. After the spray coating has dried on, the cotton plants are populated with 10 adult *Anthonomus grandis,* 10 *Spodoptera littoralis* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising emamectin benzoate and conventional CryIIIA-toxin at a concentration of in each case 100, 50, 10, 5, 1 ppm respectively.

In this test, the control of the tested insects in the transgenic plant is superior, while it is insufficient in the non-transgenic plant.

Example B7

Action Against *Ostrinia nubilalis, Spodoptera* spp. or *Heliothis* spp.

A plot (a) planted with maize cv. KnockOut® and an adjacent plot (b) of the same size which is planted with conventional maize, both showing natural infestation with *Ostrinia nubilalis, Spodoptera* spp. or *Heliothis,* are sprayed with an aqueous emulsion spray mixture comprising 200, 100, 50, 10, 5, 1 ppm of spinosad. Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia nubilalis, Spodoptera* spp. or *Heliothis* is observed on the plants of plot (a), while plot (b) shows a control level of not over 80%.

Example B8

Action Against *Ostrinia nubilalis, Spodoptera* sp or *Heliothis* sp

A plot (a) planted with maize cv. KnockOut® and an adjacent plot (b) of the same size which is planted with conventional maize, both showing natural infestation with *Ostrinia nubilalis, Spodoptera* sp or *Heliothis,* are sprayed with an aqueous emulsion spray mixture comprising 200, 100, 50, 10, 5, 1 ppm of abamectin. Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia nubilalis, Spodoptera* sp or *Heliothis* is observed on the plants of plot (a), while plot (b) shows a control level of not over 80%.

Example B9

Action Against *Ostrinia nubilalis, Spodoptera* sp or *Heliothis* sp

A plot (a) planted with maize cv. KnockOut® and an adjacent plot (b) of the same size which is planted with conventional maize, both showing natural infestation with *Ostrinia nubilalis, Spodoptera* sp or *Heliothis,* are sprayed with an aqueous emulsion spray mixture comprising 200, 100, 50, 10, 5, 1 ppm of emamectin benzoate. Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia nubilalis, Spodoptera* sp or *Heliothis* is observed on the plants of plot (a), while plot (b) shows a control level of not over 80%.

The invention further relates to (B) A method of protecting plant propagation material and plant organs formed at a later point in time from attack by pests, characterized in that a pesticide comprising, as pesticidally active compound, at least one macrolide compound, especially abamectin, emamectin or spinosad in free form or in agrochemically utilizable salt form as active ingredient and at least one auxiliary in close spatial proximity to, or spatially together with, planting or applying the propagation material is employed to the site of planting or sowing;

the corresponding use of these compounds, corresponding pesticides whose active ingredient is selected from amongst these compounds, a method of producing and using these compositions, and plant propagation material thus protected against attack by pests.

The macrolides used according to the invention are known to those skilled in the art. They are the classes of substances as mentioned under invention part (A). Abamectin and emamectin are preferred.

Agrochemically utilizable salts of the macrolides according to the invention are, for example, the same as under invention part (A).

In the case of abamectin, the free form is preferred in the frame of invention part (B). Especially preferred within the scope of the invention part (B) is a method in which emamectin is employed in free form or as agrochemically acceptable salt; especially as salt; in particular as the benzoate, substituted benzoate, benzenesulphonate, citrate, phosphate, tartrate or maleate; preferably as the benzoate or benzenesulphonate, especially preferably as the benzoate.

The scope of the subject-matter of the invention (B) extends in particular to representatives of the classes Insecta, Arachnida and Nematoda.

These are mainly insects of the order Lepidoptera, for example *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Astylus atromaculatus, Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Heteronychus arator, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp.,

*Sparganothis* spp., *Spodoptera* spp., *Synanthedon* spp., *Thaumetopoea* spp., *Tortrix* spp., *Trichoplusia ni* and *Yponomeuta* spp.;

of the order Coleoptera, for example *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

of the order Orthoptera, for example *Blatta* spp., *Blattella* spp., *Gryllotalpa* spp., *Leucophaea maderae, Locusta* spp., *Periplaneta* spp. and *Schistocerca* spp.;

of the order Psocoptera, for example *Liposcelis* spp.;

of the order Anoplura, for example *Haematopinus* spp., *Linognathus* spp., *Pediculus* spp., *Pemphigus* spp. und *Phylloxera* spp.;

of the order Mallophaga, for example *Damalinea* spp. and *Trichodectes* spp.;

of the order Thysanoptera, for example *Frankliniella* spp., *Hercinothrips* spp., *Taeniothrips* spp., *Thrips palmi, Thrips tabaci* and *Scirtothrips aurantii;* of the order Heteroptera, for example *Cimex* spp., *Distantiella theobroma, Dysdercus* spp., *Euchistus* spp. *Eurygaster* spp. *Leptocorisa* spp., *Nezara* spp., *Piesma* spp., *Rhodnius* spp., *Sahlbergella singularis, Scotinophara* spp. and *Triatoma* spp.;

of the order Homoptera, for example *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* of the order Hymenoptera, for example *Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

of the order Diptera, for example *Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

of the order Siphonaptera, for example *Ceratophyllus* spp. and *Xenopsylla cheopis;* or of the order Thysanura, for example *Lepisma saccharina.*

Amongst the class Arachnida, they are preferably representatives of the order Acarina, for example *Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.

Especially preferred is the control of insects of the orders Coleoptera and Lepidoptera;

in the order Colepotera especially the genera and species *Agriotes* spp., *Anthonomus* spp., *Atomaria linearis, Chaetocnema tibialis, Diabrotica* spp. and *Leptinotarsa decemlineata;* in the order Lepidoptera the genera and species *Adoxophyes* spp., *Agrotis* spp., *Alabama argillaceae, Anticarsia gemmatalis, Chilo* spp., *Cydia* spp., *Ephestia* spp., *Heliothis* spp., *Keiferia lycopersicella, Mamestra brassicae, Pectinophora gossypiella, Plutella xylostella, Sesamia* spp., *Spodoptera* spp., *Tortrix* spp., and *Trichoplusia.*

A further preferred subject according to the invention part (B) is the control of representatives of the class Nematoda, such as root knot nematodes, stem eelworms and foliar nematodes; especially *Heterodera* spp., for example *Heterodera schachtii, Heterodora avenae* and *Heterodora trifolii; Globodera* spp., for example *Globodera rostochiensis; Meloidogyne* spp., for example *Meloidogyne incoginita* and *Meloidogyne javanica; Radopholus* spp., for example *Radopholus similis; Pratylenchus,* for example *Pratylenchus neglectans* and *Pratylenchus penetrans; Tylenchulus,* for example *Tylenchulus semipenetrans; Longidorus, Trichodorus, Xiphinema, Ditylenchus, Aphelenchoides* and *Anguina,* in particular *Meloidogyne,* for example *Meloidogyne incognita,* and *Heterodera,* for example *Heterodera glycines.*

The macrolides used according to the invention (B) are preventatively and/or curatively valuable active ingredients in the fields of insect control, even at low application rates, while being well tolerated by warm-blooded species, fish, beneficials and plants. The active ingredients used according to the invention are effective against all or individual development stages of normally sensitive, but also resistant, pests. The action of the active ingredients used according to the invention may become apparent directly, i.e. in the form of destruction of the pests, which occurs immediately or only after some time has elapsed, for example during ecdysis, or indirectly, for example as a reduced oviposition and/or hatching rate, the good action corresponding to a destruction rate (mortality) of at least 50 to 60%.

With the aid of the active ingredients used in accordance with the invention part (B), it is possible to control, i.e. contain or destroy, pests which occur on plant propagation material, mainly on propagation material of useful plants and ornamentals in agriculture, in horticulture and in forests, and even plant organs which grow at a later point in time are still protected from these pests, that is to say the protection lasts, for example, until resistant mature plants have developed, and where the propagation material, or the plants developing therefrom, are protected not only from pests which attack the aerial plant organs, but also from soil-dwelling pests.

Suitable plant propagation material in the invention part (B), that is, for example, seedlings, rhizomes, nursery plants, cuttings or, in particular seed (seeds), such as fruit, tubers, kernels or bulbs, are, in particular, propagation material of cereals, such as wheat, barley, rye, oats, rice, maize or sorghum; beet, such as sugar or fodder beet; fruit, for example pome fruit, stone fruit and soft fruit, for example apples, pears, plums, peaches, almonds, cherries or berries, for example strawberries, raspberries and blackberries; legumes, such as beans, lentils, peas or soya beans, oil crops, such as oilseed rape, mustard, poppies, olives, sunflowers, coconut, castor-oil plants, cacao or peanuts; cucurbits, such as pumpkins, cucumbers or melons; fibre plants, such as cotton, flax, hemp or jute; citrus fruit, such as oranges, lemons, grapefruit or mandarins; vegetables, such as spinach, lettuce, asparagus, cabbage species, carrots, onions, tomatoes, potatoes or capsicums; Lauraceae, such as avocado, Cinnamonium or camphor; or tobacco, nuts, coffee, egg plants, sugar cane, tea, pepper, grapevines, hops, Musaceae, latex plants or ornamentals;

especially of cereals, rice, cotton, maize, soya beans, oilseed rape, vegetables, potatoes, sunflowers, sugar beet and sorghum.

The genetically modified propagation material is preferably propagation material, in particular seed, which contains one or more genes expressing a pesticidal resistance, in particular an insecticidal or acaricidal, but also a fungicidal or nematocidal, resistance, which make the plant resistant to herbicides, which lead to increased resistance to plant diseases or which introduce other agronomically advantageous properties into the plant. Such plants, or their propagation material, are in particular those which contain a gene derived from a *Bacillus thuringiensis* and which encode an insecticidally active protein or contain a gene. These are, especially, genetically modified plant propagation materials of potatoes, alfalfa, cereals, such as wheat, barley, rye, oats, rice, maize or sorghum; legumes, such as beans, lentils, peas or soya beans; beet such as sugar or fodder beet; oil crops, such as oilseed rape, mustard, poppies, olives, sunflowers, coconut, castor-oil plant, cacao or peanuts; cucurbits, such as pumpkins, cucumbers or melons; fibre plants, such as cotton, flax, hemp or jute; citrus fruit, such as oranges, lemons, grapefruit or mandarins; vegetables, such as spinach, lettuce, asparagus, cabbage species, carrots, onions or tomatoes.

Examples of the genetically modified plant propagation material mentioned are, for example, the commercially available products Maximizer® (KnockOut®), Yieldgard®, Roundup Ready Soybeans®, TC Blend® or NuCOTN 33®, all of which are known to those skilled in the art.

Other fields of application for the active ingredients used in accordance with the invention part (B) are, for example, the protection of stored products or stores or in the hygiene sector; in particular the protection of domestic animals or productive livestock from pests.

The invention of subject-matter (B) therefore also relates to corresponding pesticides for use, to be selected depending on the intended aims and the prevailing circumstances, such as emulsifiable concentrates, suspension concentrates, directly sprayable or dilutable solutions, spreadable pastes, dilute emulsions, sprayable powders, soluble powders, dispersible powders, wettable powders, dusts, granules or encapsulations in polymeric substances which comprise—at least—one of the active ingredients used in accordance with the invention, and to the use of these insecticidal compositions for use in a method. Preferred is a composition which comprises only one macrolide compound, especially emamectin or a salt thereof.

In these compositions, the active ingredient is employed in pure form, for example a solid active ingredient in a particular particle size or, preferably, together with—at least—one of the auxiliaries conventionally used in the art of formulation, such as extenders, for example solvents or solid carriers, or such as surface-active compounds (surfactants).

Suitable auxiliaries such as solvents, solid carriers, surface-active compounds, non-ionic surfactants, cationic surfactants and anionic surfactants in the compositions employed in accordance with the invention are, for example, those which have been described in EP-A-736 252.

Liquid formulations for the treatment of plant propagation material according to invention part (B), especially of seed, comprise, for example, surface-active substances (1–15% by weight), such as ethoxylated tristyrenephenols and their salts, alkyl polyglycol ether ethoxylates, polyoxypropylene/polyoxyethylene copolymers, the sodium salt of lignosulphonic acid, salts of polynaphthalenesulphonic acid and alkylbenzenesulphonic acid triethanolamine salt;

antifreeze agents (5–15%), such as, for example, DL-propane-1,2-diol or propane-1,2,3-triol;

colourants (1–10%), such as pigments or water-soluble dyes;

antifoams (0.05–1%), such as polydimethylsiloxane;

coatings (1–10%), such as polyethylene glycol, polyvinyl acetate, polyvinylpyrrolidone, polyacrylate;

preservatives (0.1–1%), such as 1,2-benzoisothiazol-3-one;

thickeners (0.1–1%), such as heteropolysaccharide; and solvents, such as water.

Solid formulations for the treatment of plant propagation material, especially of seed, comprise, for example:

surface-active substances (1–10%), such as alkyl polyglycol ether ethoxylate, polyoxypropylene/polyoxyethylene copolymers, the sodium salt of lignosulphonic acid, salts of polynaphthalenesulphonic acid;

colourants (1–10%), such as pigments or water-soluble dyes;

antifoams (0.05–1%), such as polydimethylsiloxane;

coatings (1–10%), such as polyethylene glycol or cellulose; and carriers (to 100% w/w), such as silica powder, talc powder, clays and the like.

As a rule, the compositions comprise 0.1 to 99%, in particular 0.1 to 95%, of active ingredient and 1 to 99.9%, in particular 5 to 99.9%, of—at least—one solid or liquid auxiliary, it being possible, as a rule, for 0 to 25%, in particular 0.1 to 20%, of the compositions to be surfactants (% is in each case percent by weight). While concentrated compositions are more preferred as commercially available goods, the end consumer will use, as a rule, dilute compositions having much lower concentrations of active ingredient.

Preferred compositions, such as emulsifiable concentrations, dusts, suspension concentrates, wettable powders and granules have, for example, those compositions which are mentioned in EP-A-736 252.

The compositions according to the invention part (B) can also comprise other solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, and also fertilizers or other active ingredients for achieving specific effects, for example bactericides, nematicides, molluscides or selective herbicides.

The action of the compositions according to the invention part (B) can be broadened considerably by adding other, for example insecticidally, acaricidally and/or fungicidally active, ingredients and adapted to prevailing circumstances. Suitable additions of insecticidally and acaricidally active ingredients are, for example, representatives of the following classes of active ingredients: organophosphorus compounds, nitrophenols and derivatives, formamidines, triazine derivatives, nitroenamine derivatives, nitro- and cyanoguanidine derivatives, ureas, benzoylureas, carbamates, pyrethroids, chlorinated hydrocarbons and *Bacillus thuringiensis* products. Especially preferred components in mixtures are NI-25, TI-304, TI-435, MTI-446, fipronil, lufenuron, pyripfoxyfen, thiacloprid, fluxofenime; imidacloprid, thiamethoxam, fenoxycarb, diafenthiuron, pymetrozine, diazinon, disulphoton; profenofos, furathiocarb, cyromazin, cypermethrin, tau-fluvalinate, tefluthrin or *Bacillus thuringiensis* products, very especially NI-25, TI-304, TI-435, MTI-446, fipronil, thiacloprid, imidacloprid, thiamethoxam and tefluthrin.

Examples of suitable additions of fungicidally active ingredients are the following compounds: azoxystrobin; bitertanol; carboxin; $Cu_2O$; cymoxanil; cyproconazole; cyprodinil; dichlofluamid; difenoconazole; diniconazole; epoxiconazole; fenpiclonil; fludioxonil; fluquiconazole; flusilazole; flutriafol; furalaxyl; guazatin; hexaconazole; hymexazol; imazalil; imibenconazole; ipconazole; kresoxim-methyl; mancozeb; metalaxyl; R-metalaxyl; metconazole; oxadixyl, pefurazoate; penconazole; pencycuron; prochloraz; propiconazole; pyroquilone; SSF-109; spiroxamin; tebuconazole; teflutrin; thiabendazole; tolifluamide; triazoxide; triadimefon; triadimenol; triflumizole; triticonazole and uniconazole.

The compositions to be used according to the invention part (B) are prepared in a known manner, for example in the absence of auxiliaries by grinding and/or screening, for example to a particular particle size, or by compressing a solid active ingredient, and in the presence of at least one auxiliary, for example by intimately mixing and/or grinding the active ingredient with the auxiliary/auxiliaries. These methods for preparing the compositions according to the invention and the use of macrolides for preparing these compositions are also subjects of the invention.

The application methods according to the invention part (B) for the protection of plant propagation material, which, in accordance with the invention, is any plant material capable of developing complete plants after planting or sowing to the site of planting or sowing, for example seedlings, rhizomes, nursery plants, cuttings or, in particular, seed (seeds), such as fruits, tubers, kernels or bulbs, against attack by pests are characterized in that, for example, suitable compositions are applied in such a manner that they are applied in close spatial proximity to, or spatially together with, planting or sowing the propagation material to the site of planting or sowing. Application of these compositions in close spatial proximity to planting or sowing the propagation material to the site of planting or sowing takes place in accordance with the invention, preferably prior to planting or sowing the propagation material, by applying the compositions by soil application directly to the site where the propagation material has been planted or sown, for example preferably prior to sowing into the seed furrow or to a closely delimited area around the site of planting or sowing the propagation material. Application of such compositions, which takes place spatially together with planting or applying the propagation material to the site of planting or sowing is to be understood as meaning that propagation material which has been pretreated with these compositions is planted or sown at the site of planting or sowing, it being possible, depending on the intended aims and prevailing circumstances, for the pretreatment of the propagation material to be effected for example by spraying, atomizing, dusting or scattering the compositions over the propagation material or brushing or pouring the compositions over the propagation material or, in the event of seed, in particular also by dressing the seed. When carrying out seed dressing, which is preferred according to the invention, i.e. dry seed, wet seed-dressing, liquid seed-dressing or slurry dressing, a suitable pesticide is added to the seed prior to sowing in a seed-dressing apparatus and the composition is distributed uniformly over the seed, for example by stirring the contents of the seed-dressing apparatus and/or by rotating and/or shaking the entire seed-dressing apparatus. Particular embodiments of such a seed-dressing treatment comprise, for example, immersing the seed in a liquid composition, coating the seed with a solid composition (seed coating) or by achieving penetration of the active ingredient into the seed by adding the composition to the water used for pre-soaking the seed (seed soaking). Typical application rates for the compositions used in the seed-dressing treatment according to the invention are, for example, between 0.1 and 100 g of active ingredient per 100 kg of seed, in particular between 1 and 60 g/100 kg of seed, preferably between 4 and 40 g/100 kg of seed.

The seed-dressing treatment according to invention part (B) comprises, in particular, that due to the low toxicity of the active ingredient used, good tolerance by birds of the dressed seed is observed, for example, in the case of birds which, being seed-eaters in the open countryside, tend to take seed from freshly seeded fields, such as buntings, blackbirds, thrushes, ducks, pheasants, finches, geese, linnets, chickens, crows, skylarks, tits, seagulls, ravens, partridges, wood pigeons, goldfinches, pigeons or siskins. The seed-dressing treatment according to the invention also extends to the dressing of stored seed.

The commercial plant propagation material which has been pretreated according to invention part (B) is another subject of the invention.

Examples of formulations of macrolide compounds which can be used in the method according to the invention (B), that is to say solutions, granules, dusts, sprayable powders, emulsion concentrates, coated granules and suspension concentrates, are of the type as has been described in, for example, EP-A-580 553, Examples F1 to F10.

Example F1

General Procedure for Liquid Seed Dressing

The required amount of liquid formulation is placed into an Erlenmeyer flask. The flask is shaken to distribute the liquid on the entire bottom of the vessel. The required amount of seed is introduced into the flask immediately thereafter. The flask is shaken vigorously by hand for approximately one minute so that all the seed is covered with liquid. The contents of the flask are turned out onto a drying rack and dried in an oven.

Example F2

General Procedure for Dry Seed Dressing

Various wide-necked flasks are each filled with the same number of seed kernels, and each flask is charged with such an amount of wettable powder that the desired amount of active ingredient per seed kernel (for example 0.03, 0.1 or 0.3 mg per kernel) is obtained. The flasks are placed on a roller and rotated for three minutes at 80 rotations/minute.

The seed kernels which are attached to the walls of the flasks are then disengaged by shaking by hand, and the flasks are rotated in the opposite direction for three minutes.

BIOLOGICAL EXAMPLES
(%=Percent by Weight, Unless Otherwise Specified)

Example B4

Seed-dressing Action Against First-instar Larvae of *Spodoptera littoralis* on Maize Leaves Maize seeds which have been dressed as described in procedure F1 are sown. 12, 19, 26, 33, 40 and 47 days after sowing, sections 5 to 8 cm in length of the top-most leaves of the plants are placed in glass beakers and infested with a predetermined quantity of a suspension of freshly hatched L1 larvae of *Spodoptera littoralis*. The beakers are closed with a lid and kept at 25° C., a relative atmospheric humidity of 60% and a day-light cycle of 16 hours. Evaluation takes place three to five days after infestation. The percentage reduction in population (% action) is determined by comparing the number of surviving larvae on the plants grown from dressed seeds and from untreated seeds.

Example B5

Seed-dressing Action Against Adult *Diabrotica balteata* on Sugar Beet Leaves

Seeds of sugar beet which have been dressed as described in procedure F1 are sown. 33, 40, 47, 54 and 61 days after sowing, the leaves of in each case three to 5 plants are placed in a glass beaker and infested with a predetermined number of young adult *Diabrotica balteata*. The beakers are closed with a lid and kept at 25° C., a relative atmospheric humidity of 60% and 16 hours of daylight. Evaluation takes place three to five days after infestation. The percentage reduction in population (% action) is determined by comparing the number of surviving *Diabrotica* adults on the plants grown from dressed seeds and from untreated seeds.

Example B6

Seed-dressing Action Against Third-Instar Larvae of *Diabrotica balteata* on Maize Roots Maize seeds which have been treated as described in procedure F1 are sown. 14, 21 and 28 days after sowing, in each case five third-instar larvae of *Diabrotica balteata* are placed on the bottom of each plant pot. Evaluation takes place 6 days after infestation. The data registered are the number of surviving instars (larvae and pupae) in the stem of the plants, on the soil surface and in the soil. The percentage reduction in population (% action) is determined by comparing the number of surviving larvae and pupae on the plants grown from dressed seeds and from untreated seeds and their environment.

Example B7

Seed-dressing Action Against *Aphis fabae*

A glass flask or a plastic container is filled with 100 g of bean seeds and such an amount of a formulation of the active ingredient that a ratio of 0.1, 1 or 10 g of active ingredient per kg of seed is achieved. The active ingredient is distributed uniformly on the seed surface by rotating and/or shaking the container. The seeds which have been dressed in this way are sown in flowerpots (3 seeds per pot). The plantlets are grown in a greenhouse at 25 to 30° C. until they have reached the 2-leaf stage and then populated with *Aphis fabae*. 6 days after population, the test is evaluated. The percentage reduction in population (% action) is determined by comparing the number of surviving individuals on the plants grown from dressed seeds and from untreated seeds.

In this test, a good action is shown by abamectin, emamectin and spinosad.

Example B8

Seed-dressing Action Against *Myzus persicae*

A glass flask or a plastic container is filled with 100 g of sugar beet seeds and such an amount of a pasty formulation of the active ingredient, prepared with a sprayable powder and a little water, that a ratio of 0.1, 1 or 10 g of active ingredient per kg of seed is achieved. The closed seed-dressing container is agitated on a roller until the paste is distributed uniformly on the seed surface. The seeds which have been dressed (coated) in this way are dried and sown into loess soil in plastic pots. The seedlings are grown in a greenhouse at 24 to 26° C., a relative atmospheric humidity of 50 to 60% and a daily illumination time of 14 hours. 4 weeks after germination, the plants, which are 10 cm high, are populated with a mixed population of *Myzus persicae*. Evaluation takes place 2 and 7 days after the plants have been populated. The percentage reduction in population (% action) is determined by comparing the number of surviving individuals on the plants grown from dressed seeds and from untreated seeds.

In this test, a good action is shown by abamectin, emamectin and spinosad.

The invention further relates to (C) A method of controlling wood pests and molluscs, characterized in that a pesticidally active amount of a pesticide comprising, as pesticidally active compound, at least one macrolide, preferably abamectin, emamectin or spinosad, in free form or agrochemically utilizable salt form, as active ingredient and at least one auxiliary is applied to the pests or their environment;

to the corresponding use of these compounds, to corresponding pesticides whose active ingredient is selected from amongst these compounds, to a process for the preparation of and to the use of these compositions, and to plant propagation material thus protected from attack by pests.

The macrolides used in accordance with the invention are the same as mentioned under the aspect (A) of the invention. Also the salt are as mentioned under invention part (A). In the case of abamectin, the free form is preferred in accordance with the invention. Especially preferred for the purposes of the present invention is a composition which comprises emamectin in free form or as an agrochemically tolerated salt as the only pesticidally active component; especially as the salt; more especially as the benzoate, substituted benzoate, benzenesulphonate, citrate, phosphate, tartrate or maleate; preferably as the benzoate or benzenesulphonate, especially preferably as the benzoate.

A larger number of different classes of active ingredient are mentioned in the literature as arthropodecidally acting active ingredients for controlling gastropods and termites. Surprisingly, it has now been found that the compounds known under the collective term macrolides, too, exhibit an important molluscicidal and termiticidal activity, specifically against gastropods, such as slugs and snails, and against wood pests, in particular representatives of the order of Isoptera.

The molluscs include, for example, *Ampullariidae; Arion* (*A. ater, A. circumscriptus, A. hortensis, A. rufus*); *Bradybaenidae* (*Bradybaena fruticum*); *Cepaea* (*C. hortensis, C. Nemoralis*); *Cochlodina; Deroceras* (*D. agrestis, D. empiricorum, D. laeve, D. reticulatum*); *Discus* (*D. rotundatus*); *Euomphalia; Galba* (*G. trunculata*); *Helicella* (*H. itala, H. obvia*); *Helicidae* (*Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The termites include, in particular, the families Hodotermitidae, Kalotermitidae, Rhinotermitidae and Termitidae. Other pests which damage wood by feeding on wood, using it as a substrate or reproducing on wood, are to be understood as meaning, for example, wood-boring insects such as representatives of the family Lyctidae, the family Apidae, for example *Xylocopa virginica,* and of the family Anobiidae, such as *Anobium punctatum.*

Slugs and snails as pests in horticulture and agriculture are a massively increasing problem. They can cause severe plant damage by feeding, and can also bring about undesirable soiling by slug and snail mucus and faeces. Novel changes in the management of crops have led to an increased number in varieties of plant species which are sensitive to slugs and snails, and the obligation to dispense with burning stubble fields—which is based on an ecological approach—and to plough in the straw instead suggests that the existing mollusc problems, especially slug problems, will be made worse.

Termites are capable of inflicting substantial damage to buildings in particular at geographical latitudes of between 42° N and 42° S. In principle, two types of termites can be distinguished:

Termites which live in the subsoil—the most widely distributed type—require warm air and a moist environment. In order always to have available the necessary moisture, these termites must have direct access to the moist soil. Damage caused by subterranean termites is virtually always associated with damage to wood.

Termites which use dry wood as their substrate represent—even though less frequently—a large problem since they do not require contact with the moist soil. They penetrate into buildings underneath roof shingles, through gaps and through ventilation holes. Others are brought into households with items of furniture which are already infested. Pretreatment of the wood is considered the most efficient method of controlling such termites. The damages of termites living on dry wood are caused more slowly than damages of termites living in a moist environment, therefore, damage caused by termites of the first-mentioned type is found predominantly in old buildings.

Damage caused by termites living subterraneously in a humid environment can be prevented by the application of insecticidally active substances to the termites or their environment. Such compounds are conventionally employed mainly for application to the soil around the buildings.

Gastropodicides which are currently commercially available comprise metaldehyde and carbamates such as, for example, methiocarb. Carbamates are highly effective as molluscicides, but exhibit the serious disadvantage of being highly toxic to mammals such as, for example, cats, dogs and hedgehogs, and other organisms such as, for example, earthworms, which should be left unharmed. While the metaldehyde molluscicides exhibit a lower toxicity, they are not lethal to molluscs but have an anaestheticizing or dehydrating effect, thus immobilizing the pests. There is therefore a demand for a useful molluscicide which is highly effective against, for example, slugs and snails, but has no, or a very low, toxic effect on beneficials such as, for example, earthworms, and mammals. This object is achieved with the macrolides of the present invention.

Also, the currently available compositions for controlling termites are not satisfactory in all respects since generally relatively large zones around building constructions, or these buildings themselves, must be treated with large amounts of insecticide. This can lead to secondary problems, in particular in the case of persistent pesticides, especially in houses. Here too, there is therefore a further demand for improved solutions, in particular by applying active ingredients which can be employed in particularly low quantities and which have low volatility.

The invention part (C) therefore also relates to pesticides such as emulsifiable concentrates, suspension concentrates, directly sprayable or dilutable solutions, spreadable pastes, dilute emulsions, sprayable powders, soluble powders, dispersible powders, wettable powders, dusts, granules, pellets or encapsulations in polymeric substances, all of which are to be chosen to suit the intended aims and the prevailing circumstances and which comprise—at least—one of the active ingredients according to the invention.

The active ingredient is employed in these compositions in pure form, for example a solid active ingredient in a particular particle size, or, preferably, together with—at least—one of the auxiliaries or carriers conventionally used in formulation technology.

Examples of formulation auxiliaries are solid carriers, solvents, stabilizers, slow-release auxiliaries, colorants and, if appropriate, surface-active substances (surfactants). Suitable carriers and auxiliaries are all substances conventionally used in crop protection products, in particular in gastropodicides. Suitable auxiliaries such as solvents, solid carriers, surface-active compounds, non-ionic surfactants, cationic surfactants, anionic surfactants and other auxiliaries in the compositions employed in accordance with the invention are, for example, those which have been described in EP-A-736'252.

Other suitable substances which can be used as carriers for molluscicides are phagostimulants, that is to say the attractants and/or food (that is to say substances which can be utilized physiologically by slugs and snails) usually contained in slug and snail bait formulations. Mixtures of phagostimulants with other suitable organic and/or inorganic carriers may also be used.

Suitable phagostimulants for molluscicides are preferably: ground cereals, such as, for example, wheat flour, barley flour, rye flour, and also rice starch, crushed soya beans, fish meal, molasses, crushed rapeseed and the like. It is possible to employ either only one phagostimulant or else a mixture of phagostimulants.

To make the bait more palatable for the molluscs, one or more of the following substances can be used as additive for slug and snail baits:

a) a vitamin B, in particular B1, B2, nicotinic acid or nicotinamide;

b) vitamin E;

c) animal or vegetable proteinaceous material, for example albumins and their hydrolytic degradation products, in particular those obtained by enzymatic hydrolysis by, for example, pepsin, such as metaproteins, proteoses, peptones, polypeptides, peptides, diketopiperazines and amino acids;

d) one or more amino acids or salts or amides thereof, which may also be synthetic products;

e) a nucleic acid or a hydrolytic degradation product thereof, such as a nucleotide, a nucleoside, adenine, guanine, cytosine, uracile or thymine;

f) urea, carbamic acid;

g) an ammonium salt, for example ammonium acetate;

h) an amino sugar, for example, glucosamine or galactosamine;

i) compounds of sodium, potassium, calcium or magnesium, or traces of compounds of manganese, copper, iron, cobalt, zinc, aluminium, boron or molybdenum, in particular chelates of these, such as Versene®;

j) phosphoric acid, or glyceryl or sugar phosphates;

k) water.

Stabilizers may be all known food stabilizers which have a fungistatic, fungicidal, bacteriostatic and/or bactericidal action, such as sodium benzoate, methyl p-hydroxybenzoate, cetyltrimethylammonium bromide, citric acid, tartaric acid, sorbic acid, phenols, alkylphenols or chlorinated phenols.

Slow-release auxiliaries which may be employed include, in addition to the substances mentioned as solid carriers, resins such as urea/formaldehyde resins, soya-bean meal, waxes, stearates and oils such as castor oil.

Substances which can be employed as auxiliaries for molluscicides according to part (C) of the invention are, for example, binders such as methylcellosolve, polyvinylpyrrolidone, polyvinyl alcohol, polyacrylates, polymethacrylates, natural waxes, chemically modified waxes and synthetic waxes, sugars, starch, alginates, agar, lignosulphonates and gum arabic, humectants such as polyalcohols, for example sugars or glycerol, preservatives, colorants, snail and slug attractants, repellents for warm-blooded species and/or other formulation auxiliaries. Combinations with known molluscicidally active ingredients, for example metaldehyde or mercaptodimethur, are also possible.

The formulation steps can be complemented by kneading, granulating (granules) and, if appropriate, compressing (pills, tablets, pellets).

The molluscicidal compositions which preferably comprise, other carriers and/or auxiliaries in addition to the active ingredient are preferably present in the ready-to-use form as sprayable powders, tracking powders, as granules (the active ingredient being present as a mixture with the carrier material), or as pellets. Especially preferred formulations are tracking powders, granules or pellets.

Formulations which are specifically suitable for controlling molluscs according to part (C) of the invention are granules or pellets which comprise, as a rule, 0 to 90%, preferably 0 to 70%, of carrier material, 0.1 to 10%, preferably 1 to 5%, of active ingredient, 10 to 95%, preferably 25 to 90%, of phagostimulant, 0.5 to 25%, preferably 5 to 20%, of binder and, if appropriate, 0 to 15% of other auxiliaries (% is in each case percent by weight).

The amount to be applied in each case as gastropodicide is not critical, due to the lack of, or low, toxicity to warm-blooded species and depends on the prevailing circumstances, such as severity of infestation, climatic conditions and the plants to be protected. The application rate of bait types according to the invention can be varied within a substantial range. In general, between 3 and 15 kg of snail and slug bait are used per hectare, preferably between 5 and 10 kg per hectare. Expediently, the gastropodicides are distributed as uniformly as possible between the crop plants by spraying an aqueous suspension or by spreading the powders, granules or pellets on the soil. If the plant canopy is not dense, it may also be expedient to establish "trapping strips" around the plants to be protected.

Since the gastropodicides according to the invention are outstandingly well tolerated by plants, no limitations apply to the plants to be protected. Thus, all ornamentals and crop plants in agriculture, forests and horticulture (also in greenhouses) in all growth stages can be protected from slug and snail damage.

The formulation and the use of the slug and snail baits according to the invention and of the compositions for controlling wood pests can be seen from the examples which follow.

The compositions to be used according to the invention part (C) for controlling gastropods and wood pests are prepared in the known manner, in the absence of auxiliaries for example by grinding and/or straining, for example to obtain a particular particle size, or by compressing a solid active ingredient, and in the presence of at least one auxiliary for example by intimately mixing and/or grinding the active ingredient with the auxiliary/auxiliaries. These processes for the preparation of the compositions according to the invention and the use of the macrolides for the preparation of these compositions are also the subject of the invention.

As a rule, the compositions in the frame of part (C) of the invention comprise 0.1 to 99%, in particular 0.1 to 95%, of active ingredient and 1 to 99.9%, in particular 5 to 99.9%, of—at least—one solid or liquid auxiliary, it being possible, as a rule, for surfactants to account for 0 to 25%, in particular 0.1 to 20%, of the compositions (% is in each case percent by weight). While concentrated compositions are more preferred as commercially available goods, the consumer uses, as a rule, dilute compositions which have much lower concentrations of active ingredient.

The activity of the compositions according to the invention can be widened considerably by adding other, for example insecticidally, acaricidally and/or fungicidally active ingredients and adapted to the prevailing circumstances. Examples of suitable added active ingredients are the same as mentioned under part (B) of the invention.

In an especially preferred embodiment of the invention, the macrolide compound is used for controlling the termites and other wood-destroying pests in the soil, thus achieving an indirect protection of timber constructions. An amount of the macrolide sufficient to control the pests is applied to the soil, preferably at an application rate of 1 g to 2000 g per hectare, especially 2 to 200 g, in particular 5 to 100 g.

Worker termites must work on the pesticide-treated soil to gain access to the wood. Inevitably, they will take up some of the pesticide and carry it back to the termite colony and thus spread the active ingredient in the termite colony.

The active ingredient(s) can also be applied in the form of baits, for example in the form of tablets which comprise the active ingredient, such as are described in U.S. Pat. No. 5,096,710. Especially preferably, the macrolide is applied to materials which are used by the termites as food and building materials for the termite colony. Examples of such materials are board, paper, wood dust, cellulose powder or cotton. Useful concentrations on these materials are 0.01 to 10,000 ppm. Such baits are especially efficient even when pheromones are additionally employed and wood is used which has already been attacked by fungi. Such uses are discussed, for example, in in U.S. Pat. No. 5,151,443.

The macrolides according to the invention part (C) are preventatively and/or curatively valuable active ingredients with a very favourable biocidal spectrum in the field of mollusc and wood-pest control, even at low use concentrations, and are well tolerated by warm-blooded species, fish and plants. The active ingredients according to the invention are active against all or individual developmental stages of normally sensitive, but also resistant, molluscs and wood pests, especially termites. The molluscicidal action of the active ingredients according to the invention may manifest itself directly, i.e. in destruction of the pests, either immediately or only after some time has elapsed, or indirectly, for example in a reduced oviposition and/or hatching rate, the good action corresponding to a destruction rate (mortality) of at least 50 to 60%.

Using the active ingredients according to the invention part (C), it is possible to control, i.e. contain or destroy, mollusc damage in particular on plants, mainly on useful plants and ornamentals in agriculture, in horticulture and in forests, or pests of the above-mentioned type which occur on organs of such plants, such as fruits, flowers, foliage, stalks, tubers or roots and in some cases even plant organs which grow at a later point in time are still protected from these pests.

Suitable target crops for mollusc control are, in particular, cereals, such as wheat, barley, rye, oats, rice, maize or sorghum; beet, such as sugar or fodder beet; fruit, for example pome fruit, stone fruit and soft fruit, such as apples, pears, plums, peaches, almonds, cherries or berries, for example strawberries, raspberries or blackberries; legumes such as beans, lentils, peas or soya beans; oil crops such as oil seed rape, mustard, poppies, olives, sunflowers, coconuts, castor, cacao or peanuts; the marrow family, such as pumpkins, cucumbers or melons; fibre plants such as cotton, flax, hemp or jute; citrus fruits such as oranges, lemons, grapefruits or tangerines; vegetables such as spinach, lettuce, asparagus, cabbage species, carrots, onions, tomatoes, potatoes, or capsicums; the laurel family such as avocado, Cinnamonium or camphor; and tobacco, nuts, coffee, egg plants, sugar cane, tea, pepper, grapevines, hops, the banana family, latex plants and ornamentals.

Other fields of application for the active ingredients according to the invention part (C) are the protection of stored products and stores and of materials from molluscs and wood pests.

The compositions according to the invention part (C) are also suitable for the protection of plant propagation material, for example seed, such as fruits, tubers or kernels, or plant propagules, from gastropods and termites, especially gastropods. The propagation material can be treated with the composition prior to planting, for example seed prior to sowing. Alternatively, the active ingredients according to the invention can be applied to seed kernels (coating) either by soaking the kernels in a liquid composition or by coating them with a solid composition. Alternatively, the composition can be applied to the site of planting when the propagation material is being planted, for example into the seed furrow during sowing. These treatment methods for plant propagation material and the plant propagation material treated thus are further subjects of the invention.

The examples which follow are intended to illustrate part (C) of the invention. They do not impose any limitation thereto.

FORMULATION EXAMPLES

Example F3

Preparation of Slug Pellets 40 kg of crushed rapeseed (ratio of extracted/non-extracted crushed rapeseed=65:35), 2.6 kg of a finely ground premix comprising 2.1 kg of macrolide and 500 g of highly-disperse silica, 4.7 kg of cold crosslinked cornstarch, 540 g of urea/formaldehyde resin, 100 g of isopropanol, 3 kg of sugar beet molasses and 140 g of blue colorant (1,4-di (isobutylamino)anthraquinone) are introduced in succession into a mixer and mixed intimately. This is followed by compression moulding. The product is left to cool and dry, and fines are removed using a 0.5 mm screen. This gives a ready-to-use slug and snail bait formulation.

Instead of the abovementioned compression moulding method, another, customary compacting method may also be used for preparing the slug and snail bait formulation.

USE EXAMPLES

Example A1

Test for Determining the Efficacy of Slug and Snail Pellets Against *Deroceras reticulatum*

The efficacy of slug and snail pellets against small slug species, for example *Deroceras* species, is tested in polycarbonate boxes with a 17 cm×22 cm base. The bottom of the box is covered with several layers of cellulose paper which is moistened sufficiently. The slug and snail pellets are scattered uniformly over one half of the test area at an application rate of 20 particles; the other half remains untreated. To avoid forced behaviour, the slugs are additionally given untreated supplementary feed: two potato halves arranged in diagonally opposite corners of the box. 10 adult reticulated field slugs (*Derocers reticulatum*) are introduced to the untreated area of each box. Each test is replicated three times. Temperature and atmospheric humidity are kept virtually constant during the entire test period: 19° and 90 to 95% relative atmospheric humidity. The state of the slugs is checked and scored daily on seven consecutive days. When assessing the efficacy, the mortality rate and the number of animals which show symptoms of damage are taken into consideration.

In this test, the macrolides according to the invention are very effective.

Example A2

Test for Determining the Efficacy of Slug and Snail Pellets Against *Arion rufus*

The efficacy of slug and snail pellets against larger slug species is tested in plastic test boxes equipped with a wire mesh. Each box has a base of 0.25 m². The bottom of the box is covered by a 2 to 3 cm deep layer of potting compost. The potting compost is moistened sufficiently before the beginning of the experiment. Slug and snail pellets are scattered uniformly over the left half of the experimental area at an application rate of 3.1 g; the right half remains untreated. To avoid forced behaviour, the slugs are additionally given untreated supplementary feed: two potato halves arranged in diagonally opposite corners of the box. 10 adult red slugs (*Arion rugus*) are introduced to the untreated area of each box. Each test is replicated four times. Temperature and atmospheric humidity are kept virtually constant during the entire test period: 19° and 90 to 95% relative atmospheric humidity. The state of the slugs is checked and scored daily on seven consecutive days. When assessing the efficacy, the mortality rate and the number of animals which show symptoms of damage are taken into consideration.

In this test, the macrolides according to the invention are very effective.

Example A3

**Test for Determining Systemic Efficacy Against *Deroceras reticulatum*** a) Lettuce Plants

A test solution is prepared by dissolving a macrolide sample in 1 ml of acetone and making up the solution with water to 50 ml. The roots, previously cleaned with fresh water, of young lettuce plants 6 cm in height are immersed for at least two days in this solution. For each test, individual leaves are excised from these lettuce plants and placed on a paper filter in a 9 cm Petri dish. 1 ml of water is pipetted onto each paper filter to keep the leaves moist during the experiment. Then, two medium-sized slugs are introduced into each Petri dish and the amount of consumed leaves and the mortality is determined over a period of two days.

In this test, the macrolides according to the invention show a good action.

b) Seed

Batches of 10 slugs are introduced into 5 sealed boxes containing compost and having a base of 35 cm×20 cm. In each case 100 treated winter wheat kernels are scattered uniformly into four boxes. In the fifth box, 50 treated winter wheat kernels are distributed over one side of the box and 50 untreated winter wheat kernels over the other side of the box to test the repellent action.

In this test, the macrolides according to the invention are very effective.

Example A4

Action Against Termites

Wood baits are treated with different amounts of macrolide, and their effect on hatching rate and survival of termites is tested. Solutions with concentrations of 0 ppm, 0.1 ppm, 100 ppm and 1000 ppm of the test substance in acetone are used. Water is used in the control study. The baits consist of pine wood which have been kept in a natural environment for four months.

The termites are collected from infested pieces of wood in the open. To carry out the wood bait study, the wood is kept for 48 hours in an oven at 80° C. The dried wood is then weighed, and the pieces are placed for 18 hours in solutions of the active ingredient at the desired concentration. The pieces of wood are then removed from the solutions, dried in the air and reweighed. To determine the action of the baits against termites, the pieces of wood thus treated are placed on a thin layer of untreated soil in Petri dishes.

The termites (50 workers and 2 soldiers) are introduced into each Petri dish. The dishes are inspected three times per week, over a period of 8 weeks. Insect development, abnormalities and mortalities are recorded. After 8 weeks, the logs are rinsed with water and dried again in an oven for 48 hours at 80° C. Again, the weight of each piece of wood is subsequently determined. The weight differential corresponds to the amount of the wood consumed by the termites.

In this test, the macrolides according to the invention are very effective.

What is claimed is:

1. A method of controlling pests selected from representatives of the class Nematoda in crops plants, which comprises treating the seed of the plants prior to planting or sowing with an effective amount of a pesticidal composition comprising abamectin or salt thereof and at least one auxiliary to control said pests.

2. The method according to claim 1, wherein abamectin is employed in free form.

3. A method of protecting seed and plant organs which grow at a later point in time against representative of the class Nematoda, which comprises treating said seed prior to planting or sowing with an effective amount of a pesticide composition comprising abamectin and at least one auxiliary wherein said treatment protects said seed and plant organs against said nematodes.

4. A method of protecting seed and plant organs which grow at a later point in time against representatives of the class Nematoda, which comprises treating said seed prior to planting or sowing with an effective amount of a pesticide composition comprising abamectin and at least one auxiliary wherein said treatment protects said seed and plant organs against said nematodes wherein said pesticide composition is a suspension concentrate.

5. The method of according to claim 1, wherein said crop plant in selected from cereals, rice, cotton, maize, soya beans, oilseed rape, vegetables, potatoes, sunflowers, sugar beet and sorghum.

6. A method of controlling pests selected from representatives of the class Nematodain crop plants, which comprises treating the seed of the plants prior to planting or sowing with an effective amount of pesticidal composition comprising abemectin or salts thereof and at least one auxiliary to control said pests wherein said pesticidal composition is a suspension concentrate.

7. The method according to claim 1, wherein said pesticidal composition further comprises a compound selected from NI-25, TI-304, TI-435, MTI-446, fipronil, thiacloprid, imidacloprid, thiamethoxam, spinosad and tefluthrin.

8. The method according to claim 1, wherein said pesticides composition further comprises a compound selected from azoxystrobin; bitertanol; carboxin; $Cu_2O$; cymoxanil; cyproconazole; cyprodinil; dichlofluamid; difenoconazole; diniconazole; epoxiconazole; fenpiclonil; fludioxonil; fluquiconazole; flusilazole; flutriafol; furalaxyl; guazatin; hexaconazole; hymexazol; imazilil; imibenconazole; ipconazole; kresoxim-methyl; mancozeb; metalaxyl; R-metalaxyl; metconazole; oxadixyl, pefurazoate; penconazole; pencycuron; prochloraz; propiconazole; pyroquilone; SSF-109; spiroxamin; tebuconazole; thiabendazole; tolifluamid; triazoxide; triadimefon; triadimenol; triflumizole; tritiConazole and uniconazole.

9. The method according to claim 6, wherein said auxiliary is a surfactant present in an amount of from 1–15% by weight of the composition.

10. The method according to claim 8, wherein the seed of the plant selected from cereals, rice, cotton, maize, soya beans, oilseed rape, vegetables, potatoes, sunflowers, sugar beet and sorghum is treated.

11. The method according to claim 8, wherein said pesticide composition further comprises a compound selected from NI-25, TI-304, TI-435, MTI-446, fipronil, thiacloprid, imidacloprid, thiamethoxam, spinosad and tefluthrin.

12. The method according to claim 8, wherein said pesticide composition further comprises a compound selected from azoxystrobin betertanol; carboxin; $Cu_2O$; cyproconazole; cyprodinil; dichloflumid; difenoconazole; diniconazole; epoxiconazole; fenpiclonil; fludioxonil; fluquiconazole; flusilazole; flutriafol; furalaxyl; guazatin; hexaconazole; hymexazol; imazilil; imibenconazole; ipconazole; kresoxina-methyl; mancozeb; metalaxyl; R-metalzxyl; metconazole; oxadixyl perfurazcate; penconazole; pencycuron; prochloraz; propiconazole; pyroquilone;

SSF-109; spiroxamin; tebuconazole; thiabendazole; tolifluamide; triazoxide; triadimefon; triadimenol; triflumizole; triticonazole and uniconazole.

13. The method according to claim 9, wherein said auxiliary is a surfactant present in an amount of from 1–15% by weight of composition.

14. The method according to claim 1, wherein said pesticidal composition further comprises a compound selected from NI-25, TI-304, TI-435, MTI-446, fipronil, thiacloprid, imidacloprid, thiamethoxam and tefluthrin.

15. The method according to claim 8, wherein said pesticide composition further comprises a compound selected from NI-25, TI-304, TI-435, MTI-446, fipronil, thiacloprid, imidacloprid, thiamethoxam and teflutrin.

* * * * *

UNITED STATES PATENT AND TRADEMARK OFFICE
CERTIFICATE OF CORRECTION

PATENT NO. : 6,875,727 B2
DATED : April 5, 2005
INVENTOR(S) : Hofer et al.

It is certified that error appears in the above-identified patent and that said Letters Patent is hereby corrected as shown below:

Title page,
Item [75], Inventors, delete text beginning "Dieter Hofer" to and ending with "Max Angst, Magden (CH)." Insert in its place the following:
-- Dieter Hofer, Liestal (CH); Marius Sutter, Binningen (CH); Franz Brandl, Schopfheim (DE). --
Before Item [51], Int. Cl.$^7$, insert the following:
-- [30] Foreign Application Priority Data
Switzerland 2960/97 12/23/1997
Switzerland 2961/97 12/23/1997
Switzerland 79/98 01/16/1998
Switzerland 84/98 01/16/1998
Switzerland 86/98 01/16/1998
Switzerland 418/98 02/22/1998 --

Column 123,
Line 63, delete "crops" and insert in its place -- crop --;

Column 124,
Line 4, delete "representative" and insert in its place -- representatives --;
Line 16, delete "nematodes wherein" and insert in its place -- nematodes and wherein --;
Line 18, delete "method of according" and insert in its place -- method according --;
Line 19, delete "plant in selected" and insert in its place -- plant is selected --;
Line 25, delete "of pesticidal" and insert in its place -- of a pesticidal --;
Lines 33-34, delete "pesticides" and insert in its place -- pesticidal --;
Lines 43-44, delete "tolifluamid" and insert in its place -- tolifluamide --;
Line 60, delete "azoxystrobin betertanol;" and insert in its place -- azoxystrobin; bitertanol; --;
Line 61, before "cyproconazole;" insert -- cymoxanil; --;
Line 61, delete "dichloflumid;" and insert in its place -- dichlofluamid; --;

UNITED STATES PATENT AND TRADEMARK OFFICE
CERTIFICATE OF CORRECTION

PATENT NO. : 6,875,727 B2
DATED : April 5, 2005
INVENTOR(S) : Hofer et al.

It is certified that error appears in the above-identified patent and that said Letters Patent is hereby corrected as shown below:

<u>Column 124 (cont'd),</u>
Line 65, delete "kresoxina-methyl" and insert -- kresoxim-methyl --.

Signed and Sealed this

Second Day of August, 2005

JON W. DUDAS
*Director of the United States Patent and Trademark Office*